US008372813B2

(12) United States Patent
Aggen et al.

(10) Patent No.: US 8,372,813 B2
(45) Date of Patent: Feb. 12, 2013

(54) ANTIBACTERIAL AMINOGLYCOSIDE ANALOGS

(75) Inventors: James Bradley Aggen, Burlingame, CA (US); Martin Sheringham Linsell, San Mateo, CA (US); Adam Aaron Goldblum, Berkeley, CA (US); Darin James Hildebrandt, Mountain View, CA (US); Timothy Robert Kane, Moss Beach, CA (US); Paola Dozzo, San Francisco, CA (US); Micah James Gliedt, Sunnyvale, CA (US); Heinz Ernst Moser, San Mateo, CA (US)

(73) Assignee: Achaogen, Inc., South San Francisco, CA (US)

( * ) Notice: Subject to any disclaimer, the term of this patent is extended or adjusted under 35 U.S.C. 154(b) by 63 days.

(21) Appl. No.: 13/082,143

(22) Filed: Apr. 7, 2011

(65) Prior Publication Data
US 2012/0172332 A1    Jul. 5, 2012

Related U.S. Application Data

(63) Continuation of application No. PCT/US2009/060211, filed on Oct. 9, 2009.

(60) Provisional application No. 61/104,023, filed on Oct. 9, 2008.

(51) Int. Cl.
A01N 43/04   (2006.01)
A61K 31/70   (2006.01)
C07H 15/22   (2006.01)

(52) U.S. Cl. ........ 514/38; 514/27; 514/35; 514/36; 514/39; 514/40; 536/4.1; 536/13.2; 536/13.3

(58) Field of Classification Search .......... None
See application file for complete search history.

(56) References Cited

U.S. PATENT DOCUMENTS

| | | | |
|---|---|---|---|
| 3,808,198 A | 4/1974 | Naito et al. | |
| 3,860,574 A | 1/1975 | Naito et al. | |
| 3,896,106 A | 7/1975 | Naito et al. | |
| 3,897,412 A | 7/1975 | Naito et al. | |
| 3,956,274 A | 5/1976 | Umezawa et al. | |
| 4,021,601 A | 5/1977 | Arcamone et al. | |
| 4,066,753 A | 1/1978 | Hanessian | |
| 4,078,138 A | 3/1978 | Akita et al. | |
| 4,170,642 A | 10/1979 | Umezawa et al. | |
| 4,247,687 A | 1/1981 | Hanessian | |
| 4,337,248 A | 6/1982 | Battistini et al. | |
| 4,347,354 A | 8/1982 | Cron et al. | |
| 4,424,343 A | 1/1984 | Cron et al. | |
| 4,617,293 A | 10/1986 | Wahlig et al. | |
| 4,937,257 A | 6/1990 | Gericke et al. | |
| 5,470,836 A | 11/1995 | Donno et al. | |
| 5,534,408 A | 7/1996 | Green et al. | |
| 5,763,587 A | 6/1998 | Mangia | |
| 5,935,776 A | 8/1999 | Green et al. | |
| 5,942,547 A | 8/1999 | Gustafson et al. | |
| 6,140,361 A | 10/2000 | Gustafson et al. | |
| 6,541,456 B1 | 4/2003 | Swayze et al. | |
| 6,759,523 B2 | 7/2004 | Swayze et al. | |
| 6,967,242 B2 | 11/2005 | Swayze et al. | |
| 7,893,039 B2 | 2/2011 | Swayze et al. | |
| 8,114,856 B2 | 2/2012 | Swayze et al. | |
| 2004/0229265 A1 | 11/2004 | Lapidot et al. | |
| 2005/0004052 A1 | 1/2005 | Baasov et al. | |
| 2005/0148522 A1 | 7/2005 | Baasov et al. | |
| 2008/0045468 A1 | 2/2008 | Hanessian et al. | |
| 2008/0214845 A1 | 9/2008 | Migawa et al. | |
| 2008/0293649 A1 | 11/2008 | Swayze et al. | |
| 2008/0300199 A1* | 12/2008 | Linsell et al. | .......... 514/38 |
| 2010/0099661 A1 | 4/2010 | Aggen et al. | |
| 2011/0166334 A1 | 7/2011 | Swayze et al. | |

(Continued)

FOREIGN PATENT DOCUMENTS

| | | |
|---|---|---|
| CA | 1 271 744 | 7/1990 |
| DE | 25 15 629 A1 | 10/1975 |

(Continued)

OTHER PUBLICATIONS

Alper et al., "Metal Catalyzed Diazo Transfer for the Synthesis of Azides From Amines," *Tetrahedron Letters* 37(34):6029-6032, 1996.

(Continued)

*Primary Examiner* — Traviss C McIntosh, III

(57) ABSTRACT

Compounds having antibacterial activity are disclosed. The compounds have the following structure (I):

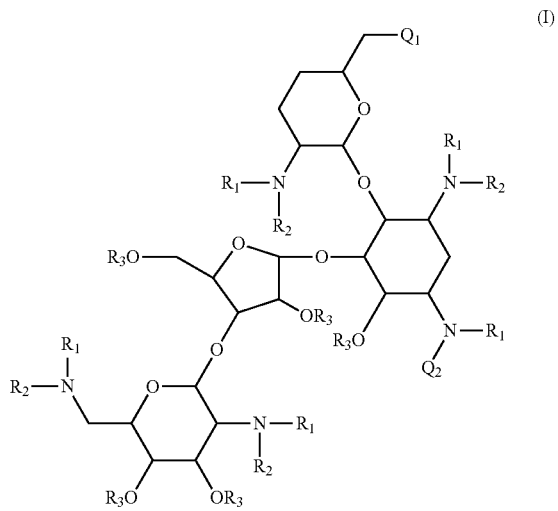

including stereoisomers, pharmaceutically acceptable salts and prodrugs thereof, wherein $Q_1$, $Q_2$, $R_1$, $R_2$ and $R_3$ are as defined herein. Methods associated with preparation and use of such compounds, as well as pharmaceutical compositions comprising such compounds, are also disclosed.

27 Claims, No Drawings

U.S. PATENT DOCUMENTS

| | | | |
|---|---|---|---|
| 2011/0245476 A1 | 10/2011 | Migawa et al. |
| 2011/0275586 A1 | 11/2011 | Aggen et al. |
| 2011/0288041 A1 | 11/2011 | Aggen et al. |
| 2012/0122809 A1 | 5/2012 | Goldblum et al. |
| 2012/0135945 A1 | 5/2012 | Dozzo et al. |
| 2012/0135946 A1 | 5/2012 | Goldblum et al. |
| 2012/0135948 A1 | 5/2012 | Goldblum et al. |
| 2012/0165282 A1 | 6/2012 | Dozzo et al. |
| 2012/0184501 A1 | 7/2012 | Dozzo et al. |
| 2012/0196791 A1 | 8/2012 | Armstrong et al. |
| 2012/0208781 A1 | 8/2012 | Bruss et al. |
| 2012/0214759 A1 | 8/2012 | Bruss et al. |
| 2012/0214760 A1 | 8/2012 | Bruss et al. |

FOREIGN PATENT DOCUMENTS

| | | |
|---|---|---|
| DE | 29 36 120 A1 | 3/1980 |
| DE | 30 44 970 A1 | 9/1981 |
| DE | 34 05 326 A1 | 8/1985 |
| EP | 0 021 150 A1 | 1/1981 |
| FR | 1.361.393 | 4/1964 |
| FR | 2.183.236 | 12/1973 |
| GB | 1 400 676 | 7/1975 |
| GB | 1 456 674 | 11/1976 |
| GB | 1 488 420 | 10/1977 |
| GB | 2 068 366 A | 8/1981 |
| GB | 1 600 457 | 10/1981 |
| JP | 49-92044 | 9/1974 |
| JP | 49-101355 | 9/1974 |
| JP | 52-100464 | 8/1977 |
| JP | 55-15445 A | 2/1980 |
| JP | 56-110697 | 9/1981 |
| WO | WO 82/00464 | 2/1982 |
| WO | WO 92/02530 | 2/1992 |
| WO | WO 94/09792 | 5/1994 |
| WO | WO 00/39139 | 7/2000 |
| WO | WO 01/54691 A1 | 8/2001 |
| WO | WO 02/053188 A1 | 7/2002 |
| WO | WO 03/059246 A2 | 7/2003 |
| WO | WO 03/101405 A2 | 12/2003 |
| WO | WO 03/105774 A2 | 12/2003 |
| WO | WO 2005/041984 A1 | 5/2005 |
| WO | WO 2006/052930 A1 | 5/2006 |
| WO | WO 2007/028012 A2 | 3/2007 |
| WO | WO 2007/064954 A2 | 6/2007 |
| WO | WO 2007/088999 A1 | 8/2007 |
| WO | WO 2008/006583 A1 | 1/2008 |
| WO | WO 2008/092690 A1 | 8/2008 |
| WO | WO 2008/124821 A1 | 10/2008 |
| WO | WO 2009/067692 A1 | 5/2009 |
| WO | WO 2010/030690 A1 | 3/2010 |
| WO | WO 2010/030704 A2 | 3/2010 |
| WO | WO 2010/042850 A1 | 4/2010 |
| WO | WO 2010/042851 A1 | 4/2010 |
| WO | WO 2010/132757 A2 | 11/2010 |
| WO | WO 2010/132759 A1 | 11/2010 |
| WO | WO 2010/132760 A1 | 11/2010 |
| WO | WO 2010/132765 A2 | 11/2010 |
| WO | WO 2010/132768 A1 | 11/2010 |
| WO | WO 2010/132770 A1 | 11/2010 |
| WO | WO 2010/132777 A2 | 11/2010 |
| WO | WO 2010/132839 A2 | 11/2010 |
| WO | WO 2010/147836 A1 | 12/2010 |
| WO | WO 2011/044498 A1 | 4/2011 |
| WO | WO 2011/044501 A2 | 4/2011 |
| WO | WO 2011/044502 A1 | 4/2011 |
| WO | WO 2011/044503 A1 | 4/2011 |
| WO | WO 2011/044538 A1 | 4/2011 |
| WO | WO 2012/067978 A1 | 5/2012 |

OTHER PUBLICATIONS

Alper et al., "Probing the Specificity of Aminoglycoside—Ribosomal RNA Interactions with Designed Synthetic Analogs," *J. Am. Chem. Soc.* 120(9):1965-1978, 1998.

Battistini et al., "Semisynthetic Aminoglycoside Antibiotics. IV 3',4'-Dideoxyparomomycin and Analogues," *The Journal of Antibiotics* 35(1):98-101, Jan. 1982.

The Merck Index, twelfth edition. Budavari (ed.), Whitehouse Station: Merck & Co., Inc., Compound 1559, 1996.

Cavender et al., "Trifluoromethanesulfonyl Azide. Its Reaction with Alkyl Amines to Form Alkyl Azides," *J. Org. Chem.* 37(22):3567-3569, 1972.

Chen et al., "Structure-toxicity relationship of aminoglycosides: Correlation of 2'-amine basicity with acute toxicity in pseudo-disaccharide scaffolds," *Bioorganic & Medicinal Chemistry* 16:8940-8951, 2008.

Chow et al., "A Structural Basis for RNA-Ligand Interactions," *Chem. Rev.* 97(5):1489-1513, Jul./Aug. 1997.

Ding et al., "Efficient synthesis of neomycin B related aminoglycosides," *Tetrahedron Letters* 41:4049-4052, 2000.

Dozzo et al., "New aminoglycoside antibiotics," *Expert Opin. Ther. Patents* 20(10):1-21, 2010.

François et al., "Antibacterial Aminoglycosides with a Modified Mode of Binding to the Ribosomal-RNA Decoding Site," *Angew. Chem. Int. Ed.* 43:6735-6738, 2004.

Georgiadas et al., "Synthesis of Amino Acid Derivatives of Neamine and 2-Deoxystreptamine to Be Used as Mutasynthons," *J. Carbohydrate Chemistry* 10(5):739-748, 1991.

Greenberg et al., "Design and Synthesis of New Aminoglycoside Antibiotics Containing Neamine as an Optimal Core Structure: Correlation of Antibiotic Activity with in Vitro Inhibition of Translation," *J. Am. Chem. Soc.* 121(28):6527-6541, 1999.

Greene, "Protective Groups in Organic Synthesis," John Wiley & Sons, Inc., New York, p. 29-39, 1981.

Hanessian et al., "Aminoglycoside antibiotics: Chemical conversion of neomycin B, paromomycin, and lividomycin B into bioactive pseudosaccharides," *Canadian Journal of Chemistry* 56(11):1482-1491, Jun. 1, 1978.

Hanessian et al., "Aminoglycoside Antibiotics 4'-Deoxyneomycin and 4'-Deoxyparomamine," *The Journal of Antibiotics* 33(6):675-678, Jun. 1980.

Hanessian et al., "Probing the functional requirements of the L-haba side-chain of amikacin-synthesis, 16S A-site or rRNA binding, and antibacterial activity," *Tetrahedron* 59: 995-1007, 2003.

Hanessian et al., "Probing the ribosomal RNA A-site with functionally diverse analogues of paromomycin—synthesis of ring I mimetics," *Tetrahedron* 63:827-846, 2007.

Hermansky, "Neomycin N-methanesulfonate," Database CAPLUS on STN, Accession No. 60:11121, 1962, 2 pages.

Hoshi et al., "Amikacin Analogs with a Fluorinated Amino Acid Side Chain," *The Journal of Antibiotics* 43(7):858-872, Jul. 1990.

Kane et al., "Basicity of the Amino Groups of the Aminoglycoside Amikacin Using Capillary Electrophoresis and Coupled CE-MS-MS Techniques," *Analytical Chemistry* 73(16):4028-4036, Aug. 15, 2001.

Kondo et al., "Crystal Structure of the Bacterial Ribosomal Decoding Site Complexed with a Synthetic Doubly Functionalized Paromomycin Derivative: a New Specific Binding Mode to an A-Minor Motif Enhances in vitro Antibacterial Activity," *ChemMedChem* 2:1631-1638, 2007.

Kumar et al., "Aminoglycoside Antibiotics. 4. Regiospecific Partial Synthesis of Ribostamycin and 4"-Thioribostamycin," *J. Org. Chem.* 46(21):4298-4300, 1981.

Lesniak et al., "An isocratic separation of underivatized gentamicin components, H NMR assignment and protonation pattern," *Carbohydrate Research* 338:2853-2862, 2003.

Li et al., "Investigation of the Regioselectivity for the Staudinger Reaction and Its Application for the Synthesis of Aminoglycosides with N-1 Modification," *J. Org. Chem.* 72(11):4055-4066, 2007.

Li et al., "Guanidine/Pd(OAc)$_2$-Catalyzed Room Temperature Suzuki Cross-Coupling Reaction in Aqueous Media under Aerobic Conditions," *J. Org. Chem.* 72(11):4067-4072, 2007.

Llewellyn et al., "Chemoenzymatic acylation of aminoglycoside antibiotics," *Chem. Commun.* 32:3786-3788, 2008.

Marrero-Ponce et al., "Non-stochastic and stochastic linear indices of the molecular pseudograph's atom-adjacency matrix: a novel approach for computational in silico screening and "rational" selection of new lead antibacterial agents," *J. Mol. Model.* 12: 255-271, 2006.

Marrero-Ponce et al., "Atom, atom-type, and total nonstochastic and stochastic quadratic fingerprints: a promising approach for modeling of antibacterial activity," *Bioorganic & Medicinal Chemistry* 13:2881-2899, 2005.

Moazed et al., "Interaction of antibiotics with functional sites in 16S ribosomal RNA," *Nature* 327:389-394, Jun. 4, 1987.

Narita et al., "Synthesis and Activity of Butirosin Derivatives with 5"-Amidino and 5"-Guanidino Substituents," *The Journal of Antibiotics* 44(1):86-92, Jan. 1991.

O'Shea et al., "Physicochemical Properties of Antibacterial Compounds: Implications for Drug Discovery," *Journal of Medicinal Chemistry* 51(10):2871-2878, May 22, 2008.

Pénasse et al., "Sur quelques dérivés mono N-alcoylés de la néomycine et de la paromomycine," *Bulletin de la Société chimique de France* 7:2391-2394, Jul. 1969.

Scholl et al., "Synthesis and Activity of a New Generation of Ruthenium-Based Olefin Metathesis Catalysts Coordinated with 1,3-Dimesityl-4,5-dihydroimidazol-2-ylidene Ligands," *Organic Letters* 1(6):953-956, 1999.

Shier et al., "Chemistry and Biochemistry of the Neomycins. XVI Synthesis and Bioactivity of Hexa-N-Benzylneomycins," *The Journal of Antibiotics* 26(10):547-550, Oct. 1973.

Sunada et al., "Enzymatic 1-N-Acetylation of Paromomycin by an Actinomycete Strain #8 with Multiple Aminoglycoside Resistance and Paromomycin Sensitivity," *The Journal of Antibiotics* 52(9):809-814, Sep. 1999.

Takahashi et al., "Syntheses of 1-Epikanamycin A and Its 1-N-[(S)-4-Amino-2-hydroxybutyryl] Derivative," *Bull. Chem. Soc. Jpn.* 56(6):1807-1811, Jun. 1983.

Takahashi et al., "Study on fluorination-toxicity relationships. Syntheses of 1-N-[(2R,3R)- and (2R,3S)-4-amino-3-fluoro-2-hydroxybutanoyl] derivatives of kanamycins," *Carbohydrate Research* 249:57-76, 1993.

Takahashi et al., "Synthesis of 1-N-[(2S,4S)- and (2S,4R)-5-amino-4-fluoro-2-hydroxypentanoyl]dibekacins (study on structure-toxicity relationships)," *Carbohydrate Research* 306:349-360, 1998.

Takamoto et al., "Aminoglycoside Antibiotics: Chemical Transformation of Paromomycin Into a Bioactive Pseudotrisaccharide," *Tetrahedron Letters* 46:4009-4012, 1974.

Takeda et al., "Mutational Biosynthesis of Butirosin Analogs II. 3',4'-Dideoxy-6'-N-Methylbutirosins, New Semisynthetic Aminoglycosides," *The Journal of Antibiotics* 31(10):1031-1038, Oct. 1978.

Takeda et al., "Mutational Biosynthesis of Butirosin Analogs III. 6'-N-Methylbutirosins and 3',4'-Dideoxy-6'-C-Methylbutirosins, New Semisynthetic Aminoglycosides," *The Journal of Antibiotics* 31(10):1039-1045, Oct. 1978.

Tamura et al., "The Synthesis of Destomycin C, a Typical Pseudo-Trisaccharide of Destomycin-Group Antibiotics," *Carbohydrate Research* 174:181-199, 1988.

Taniyama et al., "Antibiotics Aminosidin. II. Some Amino Derivatives of Aminosidin and Their Biological Activity," *Chem. Pharm. Bull.* 21(3):609-615, Mar. 1973.

Tok et al., "Binding of Aminoglycoside Antibiotics with Modified A-site 16S rRNA Construct Containing Non-Nucleotide Linkers," *Bioorganic & Medicinal Chemistry Letters* 12:365-370, 2002.

Umezawa et al., "Synthesis and Antibacterial Activity of 6'-N-Alkyl Derivatives of 1-N-[(S)-4-Amino-2-Hydroxybutyryl]-Kanamycin," *The Journal of Antibiotics* 28(6):483-485, Jun. 1975.

Van Straten et al., "An Expeditious Route to the Synthesis of Adenophostin A," *Tetrahedron* 53(18):6509-6522, 1997.

Wallis et al., "The Binding of Antibiotics to RNA," *Prog. Biophys. molec. Biol.* 67(2/3):141-154, 1997.

Watanabe et al., "Syntheses of 6'-Amino-6'-Deoxylividomycin B and 6'-Deoxy-6'-Methylamino- and 6'-Deoxy-6'-(2-Hydroxyethylamino)-Lividomycin B," *The Journal of Antibiotics* 26(12):802-804, Dec. 1973.

Watanabe et al., "Synthesis of 6'-Amino-1-N-[(S)-4-Amino-2-Hydroxybutyryl]-6'-Deoxylividomycin A," *Bulletin of the Chemical Society of Japan* 48(8):2303-2305, Aug. 1975.

Watanabe et al., "Synthesis of 1-N-[(S)-4-Amino-2-hydroxybutyryl]lividomycin A," *Bulletin of the Chemical Society of Japan* 48(7):2124-2126, Jul. 1975.

Watanabe et al., "Synthesis of 1-N-((s)-4-Amino-2-Hydroxybutyryl) Lividomycin A," *The Journal of Antibiotics* 26(5):310-312, May 1973.

Yamasaki et al., "Synthesis and Biological Activity of 1-N-[4-(Substituted)Amidino and Guanidino-2-Hydroxybutyryl]Kanamycins A and B," *The Journal of Antibiotics* 44(6):646-658, Jun. 1991.

Zaloom et al., "Preparation of Azido Derivatives from Amino Acids and Peptides by Diazo Transfer," *J. Org. Chem* 46(25):5173-5176, 1981.

International Search Report for PCT International Application No. PCT/US2005/040364, mailed Mar. 29, 2006, 4 pages.

International Search Report for PCT International Application No. PCT/US2006/034216, mailed May 3, 2007, 5 pages.

International Search Report for PCT International Application No. PCT/US2006/046122, mailed Jun. 21, 2007, 7 pages.

International Search Report for PCT International Application No. PCT/US2008/059904, mailed Jun. 19, 2008, 4 pages.

International Search Report for PCT International Application No. PCT/US2009/056391, mailed Feb. 15, 2010, 7 pages.

International Search Report for PCT International Application No. PCT/US2009/056407, mailed Mar. 30, 2010, 4 pages.

International Search Report for PCT International Application No. PCT/US2009/060211, mailed Dec. 29, 2009, 3 pages.

International Search Report for PCT International Application No. PCT/US2009/060212, mailed Dec. 9, 2009, 2 pages.

International Search Report for PCT International Application No. PCT/US2010/052045, mailed Feb. 17, 2011, 4 pages.

International Search Report for PCT International Application No. PCT/US2010/052109, mailed Feb. 23, 2011, 4 pages.

International Search Report for PCT International Application No. PCT/US2010/052040, mailed Feb. 23, 2011, 3 pages.

International Search Report for PCT International Application No. PCT/US2010/052044, mailed Feb. 23, 2011, 4 pages.

International Search Report for PCT International Application No. PCT/US2010/052043, mailed May 2, 2011, 5 pages.

International Search Report for PCT International Application No. PCT/US2011/060513, mailed Mar. 27, 2011, 4 pages.

Invitation to Pay Additional Fees for PCT International Application No. PCT/US2010/052043, mailed Feb. 24, 2011, 8 pages.

International Preliminary Report on Patentability for PCT/US2005/040364, mailed May 8, 2007, 9 pages.

International Preliminary Report on Patentability for PCT/US2006/034216, mailed Mar. 4, 2008, 8 pages.

International Preliminary Report on Patentability for PCT/US2009/056391, mailed Mar. 15, 2011, 9 pages.

International Preliminary Report on Patentability for PCT/US2006/046122, mailed Jun. 4, 2008, 11 pages.

International Preliminary Report on Patentability for PCT/US2008/059904, mailed Oct. 13, 2009, 7 pages.

International Preliminary Report on Patentability for PCT/US2009/056407, mailed Mar. 15, 2011, 5 pages.

International Preliminary Report on Patentability for PCT/US2009/060212, mailed Apr. 12, 2011, 6 pages.

International Preliminary Report on Patentability for PCT/US2009/060211, mailed Apr. 12, 2011, 7 pages.

International Preliminary Report on Patentability for PCT/US2010/052040, mailed Apr. 19, 2012, 7 pages.

International Preliminary Report on Patentability for PCT/US2010/052043, mailed Apr. 19, 2012, 12 pages.

International Preliminary Report on Patentability for PCT/US2010/052045, mailed Apr. 19, 2012, 7 pages.

International Preliminary Report on Patentability for PCT/US2010/052044, mailed Apr. 19, 2012, 8 pages.

Written Opinion for PCT/US2005/040364, mailed Mar. 29, 2006, 8 pages.

Written Opinion for PCT/US2006/034216, mailed May 3, 2007, 7 pages.

Written Opinion for PCT/US2006/046122, mailed Jun. 21, 2007, 10 pages.

Written Opinion for PCT/US2008/059904, mailed Jun. 19, 2008, 7 pages.

Written Opinion for PCT/US2009/056391, mailed Feb. 15, 2010, 8 pages.
Written Opinion for PCT/US2009/056407, mailed Mar. 30, 2010, 4 pages.
Written Opinion for PCT/US2009/060211, mailed Dec. 29, 2009, 6 pages.
Written Opinion for PCT/US2009/060212, mailed Dec. 9, 2009, 5 pages.
Written Opinion for PCT/US2010/052045, mailed Feb. 17, 2011, 5 pages.
Written Opinion for PCT/US2010/052109, mailed Feb. 23, 2011, 6 pages.
Written Opinion for PCT/US2010/052040, mailed Feb. 23, 2011, 5 pages.
Written Opinion for PCT/US2010/052043, mailed May 2, 2011, 10 pages.
Written Opinion for PCT/US2010/052044, mailed Feb. 23, 2011, 8 pages.
Written Opinion for PCT/US2011/060513, mailed Mar. 27, 2011, 7 pages.
Non-Final Office Action for U.S. Appl. No. 12/040,615, mailed Jan. 27, 2009, 6 pages.
Non-Final Office Action for U.S. Appl. No. 12/040,615, mailed Jun. 25, 2009, 16 pages.
Notice of Abandonment for U.S. Appl. No. 12/040,615, mailed Feb. 3, 2010, 3 pages.
Non-Final Office Action for U.S. Appl. No. 13/044,226, mailed May 15, 2012, 5 pages.
Non-Final Office Action for U.S. Appl. No. 09/452,606, mailed Jul. 13, 2001, 13 pages.
Office Communication for U.S. Appl. No. 09/452,606, mailed Dec. 21, 2001, 4 pages.
Final Office Action for U.S. Appl. No. 09/452,606, mailed May 7, 2002, 7 pages.
Office Communication for U.S. Appl. No. 09/452,606, mailed Feb. 5, 2003, 3 pages.
Advisory Action for U.S. Appl. No. 09/452,606, mailed Aug. 5, 2002, 3 pages.
Notice of Allowance and Fee(s) Due for U.S. Appl. No. 09/452,606, mailed Oct. 21, 2002, 3 pages.
Issue Notification for U.S. Appl. No. 09/452,606, mailed Mar. 12, 2003, 1 page.
Non-Final Office Action for U.S. Appl. No. 09/727,315, mailed Sep. 23, 2002, 7 pages.
Non-Final Office Action for U.S. Appl. No. 09/727,315, mailed Jan. 14, 2003, 10 pages.
Final Office Action for U.S. Appl. No. 09/727,315, mailed Apr. 28, 2003, 7 pages.
Notice of Allowance and Fee(s) Due for U.S. Appl. No. 09/727,315, mailed Aug. 25, 2003, 7 pages.
Notice of Allowance and Fee(s) Due for U.S. Appl. No. 09/727,315, mailed Jan. 28, 2004, 3 pages.
Issue Notification for U.S. Appl. No. 09/727,315, mailed Jun. 17, 2004, 1 page.
Non-Final Office Action for U.S. Appl. No. 10/299,220, mailed Nov. 3, 2003, 11 pages.
Notice of Non-Compliant Amendment (37 CFR 1.121) for U.S. Appl. No. 10/299,220, mailed Feb. 10, 2004, 2 pages.
Final Office Action for U.S. Appl. No. 10/299,220, mailed May 13, 2004, 10 pages including Appendices A-C.
Advisory Action for U.S. Appl. No. 10/299,220, mailed Aug. 6, 2004, 3 pages.
Notice of Allowance and Fee(s) Due for U.S. Appl. No. 10/299,220, mailed Oct. 13, 2004, 5 pages.
Response to Rule 312 Communication for U.S. Appl. No. 10/299,220, mailed Ocober 13, 2005, 2 pages.
Issue Notification for U.S. Appl. No. 10/299,220, mailed Nov. 2, 2005, 1 page.
Non-Final Office Action for U.S. Appl. No. 12/130,048, mailed May 27, 2010, 9 pages.
Notice of Allowance and Fee(s) Due for U.S. Appl. No. 12/130,048, mailed Dec. 14, 2010, 4 pages.
Issue Notification for U.S. Appl. No. 12/130,048, mailed Feb. 2, 2011, 1 page.
Non-Final Office Action for U.S. Appl. No. 12/100,981, mailed Nov. 27, 2009, 10 pages.
Non-Final Office Action for U.S. Appl. No. 12/100,981, mailed Feb. 26, 2010, 7 pages.
Final Office Action for U.S. Appl. No. 12/100,981, mailed Oct. 4, 2010, 8 pages.
Non-Final Office Action for U.S. Appl. No. 12/100,981, mailed Nov. 29, 2011, 7 pages.
Final Office Action for U.S. Appl. No. 12/100,981, mailed Jul. 6, 2012, 8 pages.
Non-Final Office Action for U.S. Appl. No. 13/044,234, mailed Apr. 27, 2012, 8 pages.
Banker, G.S., et al., "Modern Pharmceutics, Third Edition, Revised and Expanded," Marcel Dekker, Inc., New York, 1996, p. 596.
Wolff, Manfred E., "Burger's Medicinal Chemistry and Drug Discovery, Fifth Edition, vol. 1: Principles and Practice," John Wiley & Sons, Inc., 1995, pp. 975-977.
Torn et al., Synthesis of 5"-Deoxy-5"-fluorolividomycin B, Bull. Chem. Soc. Jpn. 56, 56(5):1522-1526, 1983.
Notice of Allowance and Fee(s) Due for U.S. Appl. No. 13/082,141, mailed Aug. 6, 2012 (9 pages).
Office Communication enclosing corrected Notice of Allowability for U.S. Appl. No. 13/082,141, mailed Sep. 5, 2012 (3 pages).
Notice of Allowance and Fee(s) Due for U.S. Appl. No. 13/295,219, mailed Jul. 30, 2012, 8 pages.
Non-final Office Action for U.S. Appl. No. 13/441,696, mailed Sep. 13, 2012, 10 pages.

* cited by examiner

ANTIBACTERIAL AMINOGLYCOSIDE ANALOGS

CROSS-REFERENCE TO RELATED APPLICATIONS

This application is a continuation of International PCT Patent Application No. PCT/US2009/060211, which was filed on Oct. 9, 2009, now pending, which claims the benefit under 35 U.S.C. §119(e) of U.S. Provisional Patent Application No. 61/104,023, filed Oct. 9, 2008, which applications are incorporated herein by reference in their entireties.

STATEMENT OF GOVERNMENT INTEREST

This invention was made with government support under Contract No. HHSN272200800043C, awarded by the National Institutes of Health. The government has certain rights in this invention.

BACKGROUND

1. Field

The present invention is directed to novel aminoglycoside compounds, and methods for their preparation and use as therapeutic or prophylactic agents.

2. Description of the Related Art

A particular interest in modern drug discovery is the development of novel low molecular weight drugs that work by binding to RNA. RNA, which serves as a messenger between DNA and proteins, was thought to be an entirely flexible molecule without significant structural complexity. Recent studies have revealed a surprising intricacy in RNA structure. RNA has a structural complexity rivaling proteins, rather than simple motifs like DNA. Genome sequencing reveals both the sequences of the proteins and the mRNAs that encode them. Since proteins are synthesized using an RNA template, such proteins can be inhibited by preventing their production in the first place by interfering with the translation of the mRNA. Since both proteins and the RNAs are potential drug targeting sites, the number of targets revealed from genome sequencing efforts is effectively doubled. These observations unlock a new world of opportunities for the pharmaceutical industry to target RNA with small molecules.

Classical drug discovery has focused on proteins as targets for intervention. Proteins can be extremely difficult to isolate and purify in the appropriate form for use in assays for drug screening. Many proteins require post-translational modifications that occur only in specific cell types under specific conditions. Proteins fold into globular domains with hydrophobic cores and hydrophilic and charged groups on the surface. Multiple subunits frequently form complexes, which may be required for a valid drug screen. Membrane proteins usually need to be embedded in a membrane to retain their proper shape. The smallest practical unit of a protein that can be used in drug screening is a globular domain. The notion of removing a single alpha helix or turn of a beta sheet and using it in a drug screen is not practical, since only the intact protein may have the appropriate 3-dimensional shape for drug binding. Preparation of biologically active proteins for screening is a major limitation in classical high throughput screening. Quite often the limiting reagent in high throughput screening efforts is a biologically active form of a protein which can also be quite expensive.

For screening to discover compounds that bind RNA targets, the classic approaches used for proteins can be superceded with new approaches. All RNAs are essentially equivalent in their solubility, ease of synthesis or use in assays. The physical properties of RNAs are independent of the protein they encode. They may be readily prepared in large quantity through either chemical or enzymatic synthesis and are not extensively modified in vivo. With RNA, the smallest practical unit for drug binding is the functional subdomain. A functional subdomain in RNA is a fragment that, when removed from the larger RNA and studied in isolation, retains its biologically relevant shape and protein or RNA-binding properties. The size and composition of RNA functional subdomains make them accessible by enzymatic or chemical synthesis. The structural biology community has developed significant experience in identification of functional RNA subdomains in order to facilitate structural studies by techniques such as NMR spectroscopy. For example, small analogs of the decoding region of 16S rRNA (the A-site) have been identified as containing only the essential region, and have been shown to bind antibiotics in the same fashion as the intact ribosome.

The binding sites on RNA are hydrophilic and relatively open as compared to proteins. The potential for small molecule recognition based on shape is enhanced by the deformability of RNA. The binding of molecules to specific RNA targets can be determined by global conformation and the distribution of charged, aromatic, and hydrogen bonding groups off of a relatively rigid scaffold. Properly placed positive charges are believed to be important, since long-range electrostatic interactions can be used to steer molecules into a binding pocket with the proper orientation. In structures where nucleobases are exposed, stacking interactions with aromatic functional groups may contribute to the binding interaction. The major groove of RNA provides many sites for specific hydrogen bonding with a ligand. These include the aromatic N7 nitrogen atoms of adenosine and guanosine, the O4 and O6 oxygen atoms of uridine and guanosine, and the amines of adenosine and cytidine. The rich structural and sequence diversity of RNA suggests to us that ligands can be created with high affinity and specificity for their target.

Although our understanding of RNA structure and folding, as well as the modes in which RNA is recognized by other ligands, is far from being comprehensive, significant progress has been made in the last decade (see, e.g., Chow, C. S.; Bogdan, F. M., Chem. Rev., 1997, 97, 1489 and Wallis, M. G.; Schroeder, R., Prog. Biophys. Molec. Biol. 1997, 67, 141). Despite the central role RNA plays in the replication of bacteria, drugs that target these pivotal RNA sites of these pathogens are scarce. The increasing problem of bacterial resistance to antibiotics makes the search for novel RNA binders of crucial importance.

Certain small molecules can bind and block essential functions of RNA. Examples of such molecules include the aminoglycoside antibiotics and drugs such as erythromycin which binds to bacterial rRNA and releases peptidyl-tRNA and mRNA. Aminoglycoside antibiotics have long been known to bind RNA. They exert their antibacterial effects by binding to specific target sites in the bacterial ribosome. For the structurally related antibiotics neamine, ribostamycin, neomycin B, and paromomycin, the binding site has been localized to the A-site of the prokaryotic 16S ribosomal decoding region RNA (see Moazed, D.; Noller, H. F., Nature, 1987, 327, 389). Binding of aminoglycosides to this RNA target interferes with the fidelity of mRNA translation and results in miscoding and truncation, leading ultimately to bacterial cell death (see Alper, P. B.; Hendrix, M.; Sears, P.; Wong, C., J. Am. Chem. Soc., 1998, 120, 1965).

There is a need in the art for new chemical entities that work against bacteria with broad-spectrum activity. Perhaps the biggest challenge in discovering RNA-binding antibacterial drugs is identifying vital structures common to bacteria that can be disabled by small molecule drug binding. A challenge in targeting RNA with small molecules is to develop a chemical strategy which recognizes specific shapes of RNA. There are three sets of data that provide hints on how to do this: natural protein interactions with RNA, natural product antibiotics that bind RNA, and man-made RNAs (aptamers)

that bind proteins and other molecules. Each data set, however, provides different insights to the problem.

Several classes of drugs obtained from natural sources have been shown to work by binding to RNA or RNA/protein complexes. These include three different structural classes of antibiotics: thiostreptone, the aminoglycoside family and the macrolide family of antibiotics. These examples provide powerful clues to how small molecules and targets might be selected. Nature has selected RNA targets in the ribosome, one of the most ancient and conserved targets in bacteria. Since antibacterial drugs are desired to be potent and have broad-spectrum activity, these ancient processes, fundamental to all bacterial life, represent attractive targets. The closer we get to ancient conserved functions the more likely we are to find broadly conserved RNA shapes. It is important to also consider the shape of the equivalent structure in humans, since bacteria were unlikely to have considered the therapeutic index of their RNAs while evolving them.

A large number of natural antibiotics exist, these include the aminoglycosides, such as, kirromycin, neomycin, paromomycin, thiostrepton, and many others. They are very potent, bactericidal compounds that bind RNA of the small ribosomal subunit. The bactericidal action is mediated by binding to the bacterial RNA in a fashion that leads to misreading of the genetic code. Misreading of the code during translation of integral membrane proteins is thought to produce abnormal proteins that compromise the barrier properties of the bacterial membrane.

Antibiotics are chemical substances produced by various species of microorganisms (bacteria, fungi, actinomycetes) that suppress the growth of other microorganisms and may eventually destroy them. However, common usage often extends the term antibiotics to include synthetic antibacterial agents, such as the sulfonamides, and quinolines, that are not products of microbes. The number of antibiotics that have been identified now extends into the hundreds, and many of these have been developed to the stage where they are of value in the therapy of infectious diseases. Antibiotics differ markedly in physical, chemical, and pharmacological properties, antibacterial spectra, and mechanisms of action. In recent years, knowledge of molecular mechanisms of bacterial, fungal, and viral replication has greatly facilitated rational development of compounds that can interfere with the life cycles of these microorganisms.

At least 30% of all hospitalized patients now receive one or more courses of therapy with antibiotics, and millions of potentially fatal infections have been cured. At the same time, these pharmaceutical agents have become among the most misused of those available to the practicing physician. One result of widespread use of antimicrobial agents has been the emergence of antibiotic-resistant pathogens, which in turn has created an ever-increasing need for new drugs. Many of these agents have also contributed significantly to the rising costs of medical care.

When the antimicrobial activity of a new agent is first tested, a pattern of sensitivity and resistance is usually defined. Unfortunately, this spectrum of activity can subsequently change to a remarkable degree, because microorganisms have evolved the array of ingenious alterations discussed above that allow them to survive in the presence of antibiotics. The mechanism of drug resistance varies from microorganism to microorganism and from drug to drug.

The development of resistance to antibiotics usually involves a stable genetic change, inheritable from generation to generation. Any of the mechanisms that result in alteration of bacterial genetic composition can operate. While mutation is frequently the cause, resistance to antimicrobial agents may be acquired through transfer of genetic material from one bacterium to another by transduction, transformation or conjugation.

For the foregoing reasons, while progress has been made in this field, there is a need for new chemical entities that possess antibacterial activity. Further, in order to accelerate the drug discovery process, new methods for synthesizing aminoglycoside antibiotics are needed to provide an array of compounds that are potentially new drugs for the treatment of bacterial infections. The present invention fulfills these needs and provides further related advantages.

BRIEF SUMMARY

In brief, the present invention is directed to novel aminoglycoside compounds, having antibacterial activity, including stereoisomers, pharmaceutically acceptable salts and prodrugs thereof, and the use of such compounds in the treatment of bacterial infections.

In one embodiment, compounds having the following structure (I) are provided:

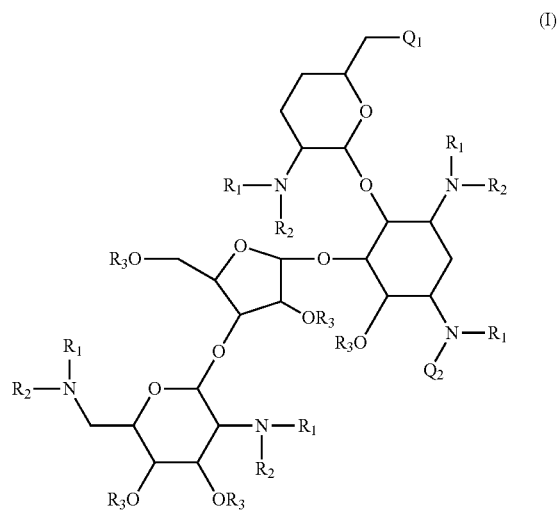

or a stereoisomer, prodrug or pharmaceutically acceptable salt thereof, wherein:

$Q_1$ is —$NR_1R_{11}$ or —$NR_{11}R_{12}$;

$Q_2$ is optionally substituted alkyl,

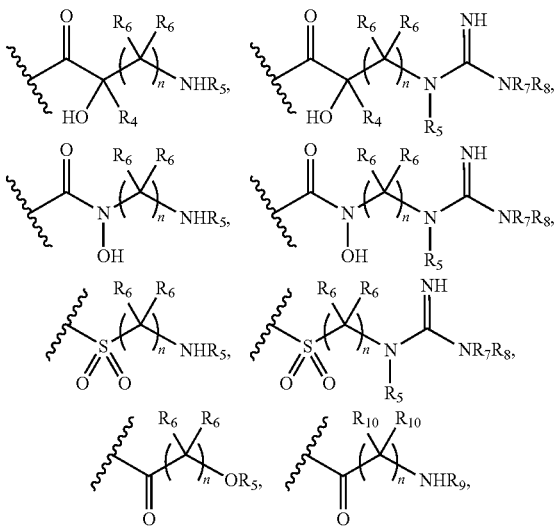

-continued

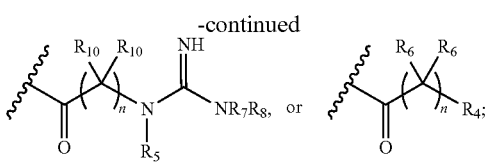

each $R_1$ and $R_2$ is, independently, hydrogen or an amino protecting group;

each $R_3$ is, independently, hydrogen or a hydroxyl protecting group;

each $R_4$, $R_5$, $R_7$ and $R_8$ is, independently, hydrogen or $C_1$-$C_6$ alkyl optionally substituted with one or more halogen, hydroxyl or amino;

each $R_6$ is, independently, hydrogen, halogen, hydroxyl, amino or $C_1$-$C_6$ alkyl;

or $R_4$ and $R_5$ together with the atoms to which they are attached can form a heterocyclic ring having from 4 to 6 ring atoms, or $R_5$ and one $R_6$ together with the atoms to which they are attached can form a heterocyclic ring having from 3 to 6 ring atoms, or $R_4$ and one $R_6$ together with the atoms to which they are attached can form a carbocyclic ring having from 3 to 6 ring atoms, or $R_7$ and $R_8$ together with the atom to which they are attached can form a heterocyclic ring having from 3 to 6 ring atoms;

each $R_9$ is, independently, hydrogen, hydroxyl, amino or $C_1$-$C_6$ alkyl optionally substituted with one or more halogen, hydroxyl or amino;

each $R_{10}$ is, independently, hydrogen, halogen, hydroxyl, amino or $C_1$-$C_6$ alkyl;

or $R_9$ and one $R_{10}$ together with the atoms to which they are attached can form a heterocyclic ring having from 3 to 6 ring atoms;

each $R_{11}$ and $R_{12}$ is, independently, $C_1$-$C_6$ alkyl or substituted $C_1$-$C_6$ alkyl; and n is an integer from 0 to 4.

In another embodiment, a pharmaceutical composition is provided comprising a compound having structure (I), or a stereoisomer, pharmaceutically acceptable salt or prodrug thereof, and a pharmaceutically acceptable carrier, diluent or excipient.

In another embodiment, a method of using a compound having structure (I) in therapy is provided. In particular, the present invention provides a method of treating a bacterial infection in a mammal comprising administering to the mammal an effective amount of a compound having structure (I), or a stereoisomer, pharmaceutically acceptable salt or prodrug thereof.

These and other aspects of the invention will be apparent upon reference to the following detailed description.

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ radical.

"Cyano" refers to the —CN radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl(iso-propyl), n-butyl, n-pentyl, 1,1-dimethylethyl(t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_bR_d$ where $R_d$ is an alkylene chain as defined above and $R_g$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl(benzothiophenyl), benzotriazolyl, benzo[4,6]imidazo pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gC(=NR_g)NR_gR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The term "protecting group," as used herein, refers to a labile chemical moiety which is known in the art to protect reactive groups including without limitation, hydroxyl and amino groups, against undesired reactions during synthetic procedures. Hydroxyl and amino groups which protected with a protecting group are referred to herein as "protected hydroxyl groups" and "protected amino groups", respectively. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999). Groups can be selectively incorporated into aminoglycosides of the invention as precursors. For example an amino group can be placed into a compound of the invention as an azido group that can be chemically converted to the amino group at a desired point in the synthesis. Generally, groups are protected or present as a precursor that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72. Examples of "hydroxyl protecting groups" include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Examples of "amino protecting groups" include, but are not limited to, carbamate-protecting groups, such as 2-trimethylsilylethoxycarbonyl (Teoc), 1-methyl-1-(4-biphenyl)-pethoxy-carbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide-protecting groups, such as 2-nitrobenzenesulfonyl; and imine and cyclic imide protecting groups, such as phthalimido and dithiasuccinoyl.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}$H, $^{3}$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection.

Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to effect treatment, as defined below, of a bacterial infection in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids.

The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

As noted above, in one embodiment of the present invention, compounds having antibacterial activity are provided, the compounds having the following structure (I):

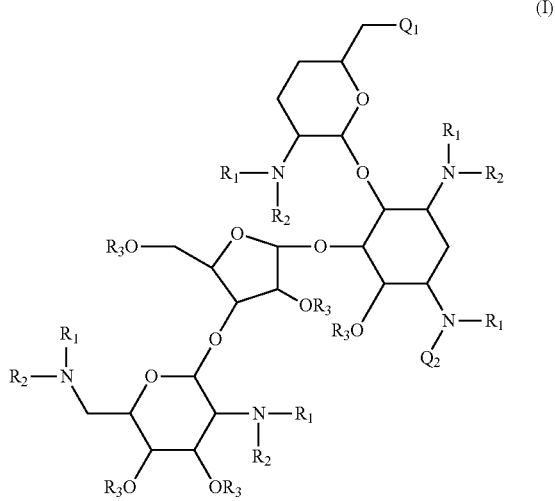

or a stereoisomer, prodrug or pharmaceutically acceptable salt thereof, wherein:

$Q_1$ is —$NR_1R_{11}$ or —$NR_{11}R_{12}$;

$Q_2$ is optionally substituted alkyl,

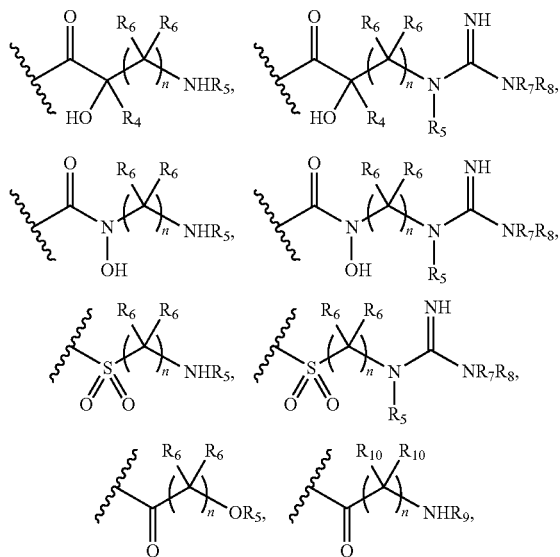

-continued

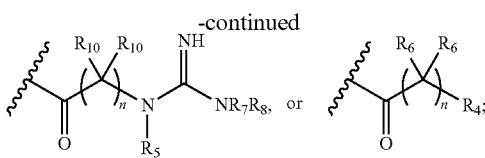

each $R_1$ and $R_2$ is, independently, hydrogen or an amino protecting group;

each $R_3$ is, independently, hydrogen or a hydroxyl protecting group;

each $R_4$, $R_5$, $R_7$ and $R_8$ is, independently, hydrogen or $C_1$-$C_6$ alkyl optionally substituted with one or more halogen, hydroxyl or amino;

each $R_6$ is, independently, hydrogen, halogen, hydroxyl, amino or $C_1$-$C_6$ alkyl;

or $R_4$ and $R_5$ together with the atoms to which they are attached can form a heterocyclic ring having from 4 to 6 ring atoms, or $R_5$ and one $R_6$ together with the atoms to which they are attached can form a heterocyclic ring having from 3 to 6 ring atoms, or $R_4$ and one $R_6$ together with the atoms to which they are attached can form a carbocyclic ring having from 3 to 6 ring atoms, or $R_7$ and $R_8$ together with the atom to which they are attached can form a heterocyclic ring having from 3 to 6 ring atoms;

each $R_9$ is, independently, hydrogen, hydroxyl, amino or $C_1$-$C_6$ alkyl optionally substituted with one or more halogen, hydroxyl or amino;

each $R_{10}$ is, independently, hydrogen, halogen, hydroxyl, amino or $C_1$-$C_6$ alkyl; or $R_9$ and one $R_{10}$ together with the atoms to which they are attached can form a heterocyclic ring having from 3 to 6 ring atoms;

each $R_{11}$ and $R_{12}$ is, independently, $C_1$-$C_6$ alkyl or substituted $C_1$-$C_6$ alkyl; and n is an integer from 0 to 4.

In further embodiments, $Q_2$ is

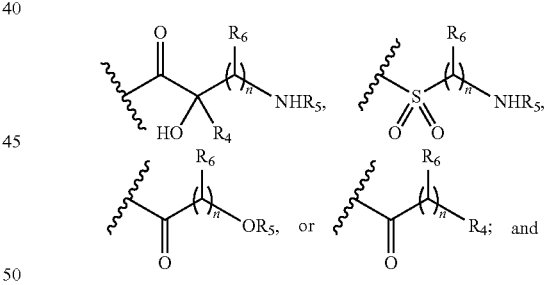

each $R_4$, $R_5$ and $R_6$ is, independently, hydrogen or $C_1$-$C_6$ alkyl, or $R_4$ and $R_5$ together with the atoms to which they are attached can form a heterocyclic ring having from 4 to 6 ring atoms, or $R_5$ and $R_6$ together with the atoms to which they are attached can form a heterocyclic ring having from 4 to 6 ring atoms, or $R_4$ and $R_6$ together with the atoms to which they are attached can form a carbocyclic ring having from 4 to 6 ring atoms.

In further embodiments, each $R_1$, $R_2$ and $R_3$ are H.

In further embodiments, $Q_1$ is —$NHR_{11}$. In further embodiments, $R_{11}$ is $C_1$-$C_6$ alkyl, such as, for example, methyl or ethyl. In other further embodiments, $R_{11}$ is substituted $C_1$-$C_6$ alkyl, such as, for example, —$(CH_2)_mOH$, wherein m is an integer from 1 to 6 (e.g., —$(CH_2)_3OH$ or —$(CH_2)_2OH$).

In other further embodiments, $Q_1$ is —$NR_{11}R_{12}$.

In further embodiments, $Q_2$ is:

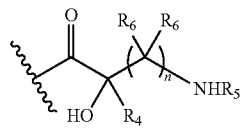

wherein: $R_4$ is hydrogen; $R_5$ is hydrogen; and n is an integer from 1 to 4. In further embodiments, each $R_6$ is hydrogen. For example, in more specific embodiments of the foregoing, $Q_2$ is:

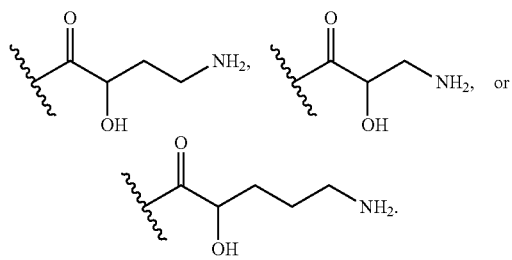

In other further embodiments, at least one $R_6$ is halogen.

In other further embodiments, $Q_2$ is:

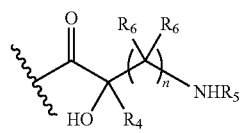

wherein: $R_4$ is hydrogen; $R_5$ and one $R_6$ together with the atoms to which they are attached form a heterocyclic ring having from 3 to 6 ring atoms; and n is an integer from 1 to 4. For example, in more specific embodiments of the foregoing, $Q_2$ is:

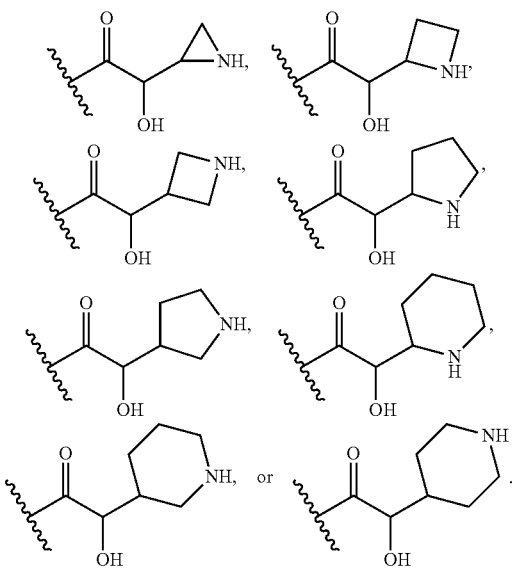

In other further embodiments, at least one $R_6$ is halogen.

In other further embodiments, $Q_2$ is:

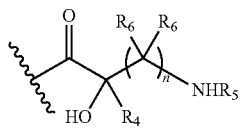

wherein: $R_4$ and $R_5$ together with the atoms to which they are attached form a heterocyclic ring having from 4 to 6 ring atoms; and n is an integer from 1 to 4. In further embodiments, each $R_6$ is hydrogen. For example, in more specific embodiments of the foregoing, $Q_2$ is:

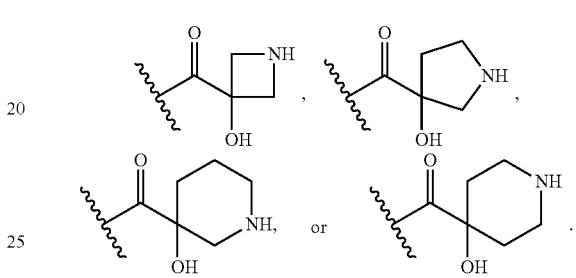

In other further embodiments, at least one $R_6$ is halogen.

In other further embodiments, $Q_2$ is:

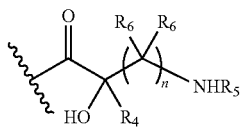

wherein: $R_5$ is hydrogen; $R_4$ and one $R_6$ together with the atoms to which they are attached form a carbocyclic ring having from 3 to 6 ring atoms; and n is an integer from 1 to 4. For example, in more specific embodiments of the foregoing, $Q_2$ is:

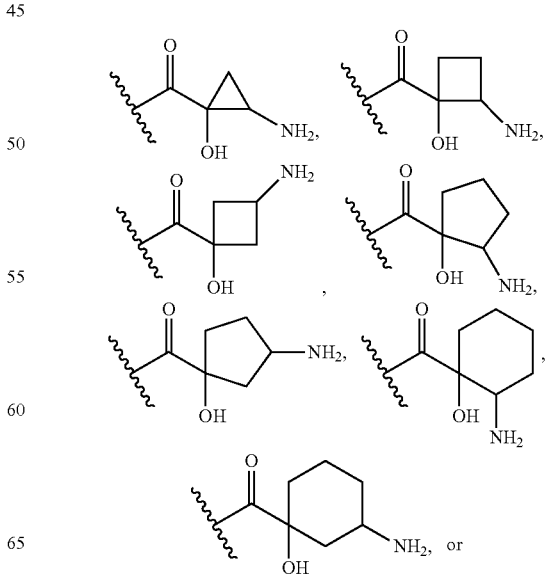

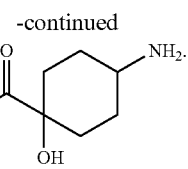

In other further embodiments, at least one $R_6$ is halogen.

In other further embodiments, $Q_2$ is:

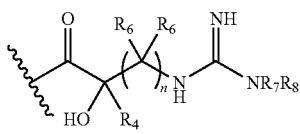

wherein: $R_4$ is hydrogen; $R_7$ is hydrogen; $R_8$ is hydrogen; and n is an integer from 1 to 4. In further embodiments, each $R_6$ is hydrogen. For example, in more specific embodiments of the foregoing, $Q_2$ is:

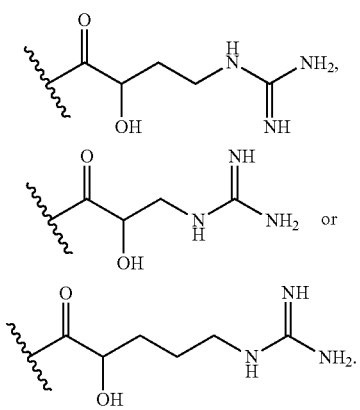

In other further embodiments, at least one $R_6$ is halogen.

In other further embodiments, $Q_2$ is:

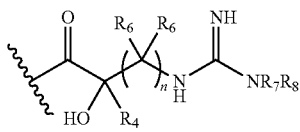

wherein: $R_4$ and one $R_6$ together with the atoms to which they are attached form a carbocyclic ring having from 3 to 6 ring atoms; $R_7$ is hydrogen; $R_8$ is hydrogen; and n is an integer from 1 to 4. For example, in more specific embodiments of the foregoing, $Q_2$ is:

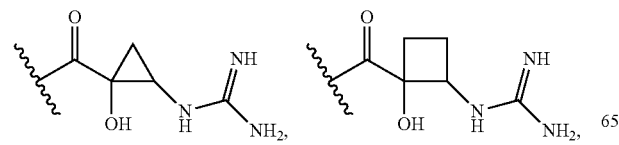

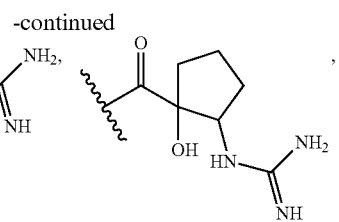

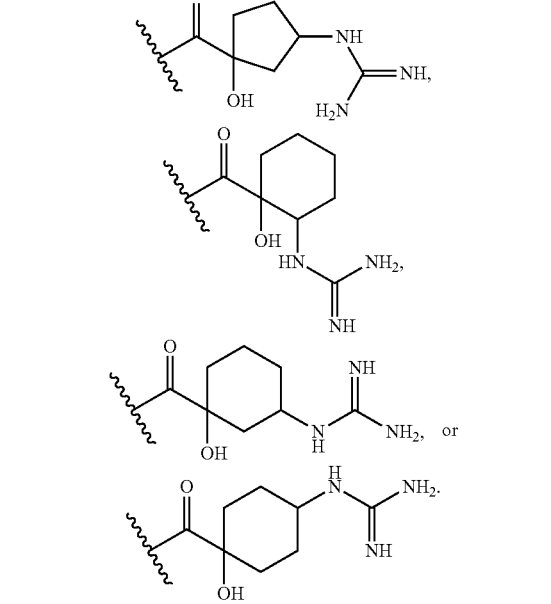

In other further embodiments, $Q_2$ is:

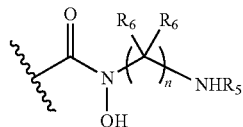

wherein $R_5$ is hydrogen. In further embodiments, each $R_6$ is hydrogen. For example, in more specific embodiments of the foregoing, $Q_2$ is:

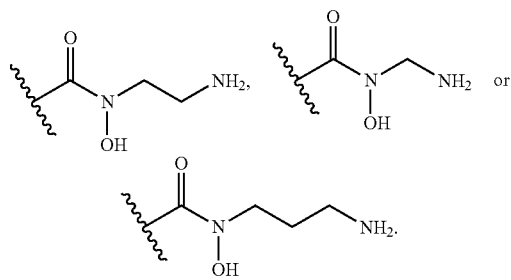

In other further embodiments, at least one $R_6$ is halogen.
In other further embodiments, $Q_2$ is:

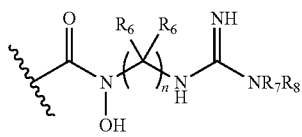

wherein: $R_7$ is hydrogen; and $R_8$ is hydrogen. In further embodiments, each $R_6$ is hydrogen. For example, in more specific embodiments of the foregoing, $Q_2$ is:

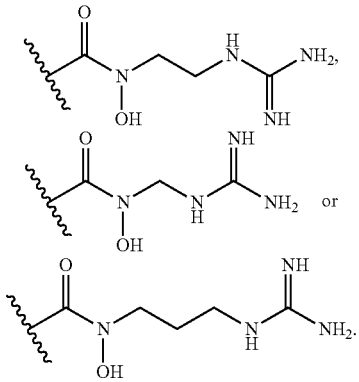

In other further embodiments, at least one $R_6$ is halogen.
In other further embodiments, $Q_2$ is:

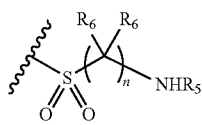

wherein $R_5$ is hydrogen. In further embodiments, each $R_6$ is hydrogen. In other further embodiments, at least one $R_6$ is halogen.
In other further embodiments, $Q_2$ is:

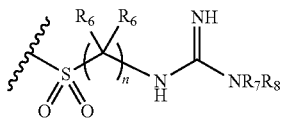

wherein: $R_7$ is hydrogen; and $R_8$ is hydrogen. In further embodiments, each $R_6$ is hydrogen. In other further embodiments, at least one $R_6$ is halogen.
In other further embodiments, $Q_2$ is:

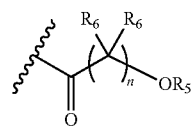

wherein $R_5$ is hydrogen. In further embodiments, each $R_6$ is hydrogen. In other further embodiments, at least one $R_6$ is halogen.
In other further embodiments, $Q_2$ is:

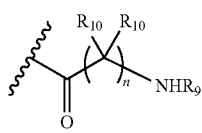

wherein $R_9$ is hydrogen. In further embodiments, each $R_{10}$ is hydrogen. In other further embodiments, at least one $R_{10}$ is halogen.

In other further embodiments, $Q_2$ is:

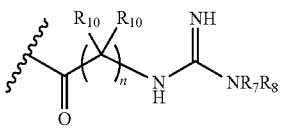

wherein: $R_7$ is hydrogen; and $R_8$ is hydrogen. In further embodiments, each $R_{10}$ is hydrogen. In other further embodiments, at least one $R_{10}$ is halogen.
In other further embodiments, $Q_2$ is:

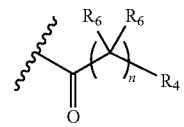

wherein $R_4$ is hydrogen. In further embodiments, each $R_6$ is hydrogen. In other further embodiments, at least one $R_6$ is halogen. In other further embodiments, $Q_2$ is —C(=O)H.

In other further embodiments, $Q_2$ is optionally substituted alkyl. For example, in more specific embodiments of the foregoing, $Q_2$ is unsubstituted or $Q_2$ is substituted with one or more halogen, hydroxyl or amino.

In further embodiments, the foregoing compounds of structure (I) have the following configuration:

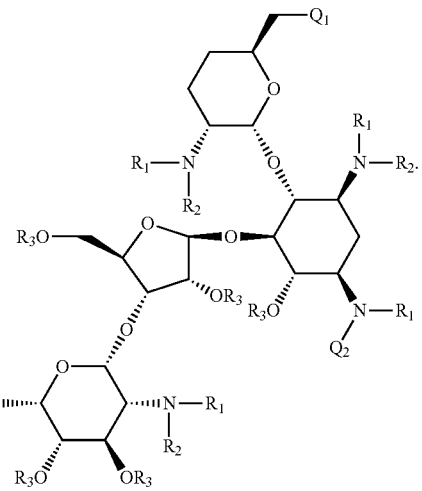

It is understood that any embodiment of the compounds of structure (I), as set forth above, and any specific substituent set forth herein for a $Q_1$, $Q_2$, $R_1$, $R_2$, $R_3$, $R_4$, $R_5$, $R_6$, $R_7$, $R_8$, $R_9$, $R_{10}$, $R_{11}$ and $R_{12}$ group in the compounds of structure (I), as set forth above, may be independently combined with other embodiments and/or substituents of compounds of structure (I) to form embodiments of the inventions not specifically set forth above. In addition, in the event that a list of substitutents is listed for any particular $Q_1$, $Q_2$, $R_1$, $R_2$, $R_3$, $R_4$, $R_5$, $R_6$, $R_7$, $R_8$, $R_9$, $R_{10}$, $R_{11}$ and $R_{12}$ group in a particular embodiment and/or claim, it is understood that each individual substituent may be deleted from the particular embodiment and/or claim and that the remaining list of substituents will be considered to be within the scope of the invention.

For the purposes of administration, the compounds of the present invention may be administered as a raw chemical or may be formulated as pharmaceutical compositions. Pharmaceutical compositions of the present invention comprise a compound of structure (I) and a pharmaceutically acceptable carrier, diluent or excipient. The compound of structure (I) is present in the composition in an amount which is effective to treat a particular disease or condition of interest—that is, in an amount sufficient to treat a bacterial infection, and preferably with acceptable toxicity to the patient. The antibacterial activity of compounds of structure (I) can be determined by one skilled in the art, for example, as described in the Examples below. Appropriate concentrations and dosages can be readily determined by one skilled in the art.

The compounds of the present invention possess antibacterial activity against a wide spectrum of gram positive and gram negative bacteria, as well as enterobacteria and anaerobes. Representative susceptible organisms generally include those gram positive and gram negative, aerobic and anaerobic organisms whose growth can be inhibited by the compounds of the invention such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella, Francisella, Anthracis, Yersinia, Corynebacterium, Moraxella, Enterococcus*, and other organisms.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

It is understood that in the present description, combinations of substituents and/or variables of the depicted formulae are permissible only if such contributions result in stable compounds.

It will also be appreciated by those skilled in the art that in the synthetic processes described herein the functional groups of intermediate compounds may need to be protected by suitable protecting groups. Such functional groups include hydroxy, amino, mercapto and carboxylic acid. As described above, suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like, and suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although a protected derivative of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The following Examples illustrate various methods of making compounds of this invention, i.e., compound of structure (I):

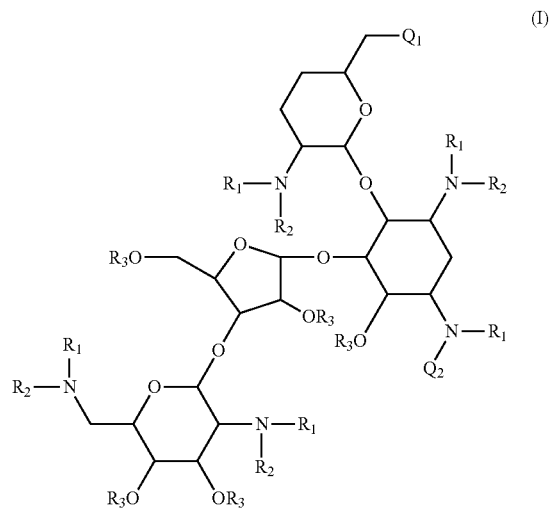

wherein $Q_1$, $Q_2$, $R_1$, $R_2$ and $R_3$ are as defined above. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

The following examples are provided for purposes of illustration, not limitation.
EXAMPLES
General Synthetic Scheme 5
N-6', N-1 Bis-substituted, 3',4'-Dideoxy Neomycin Analogs
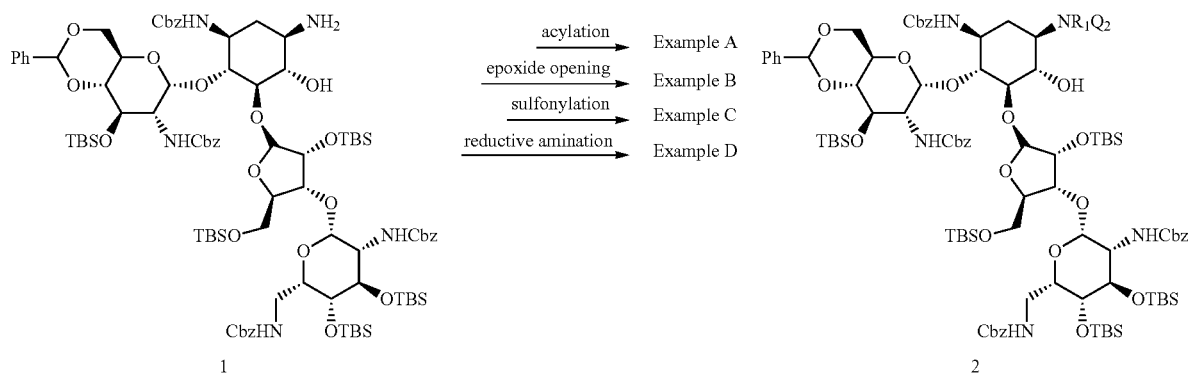
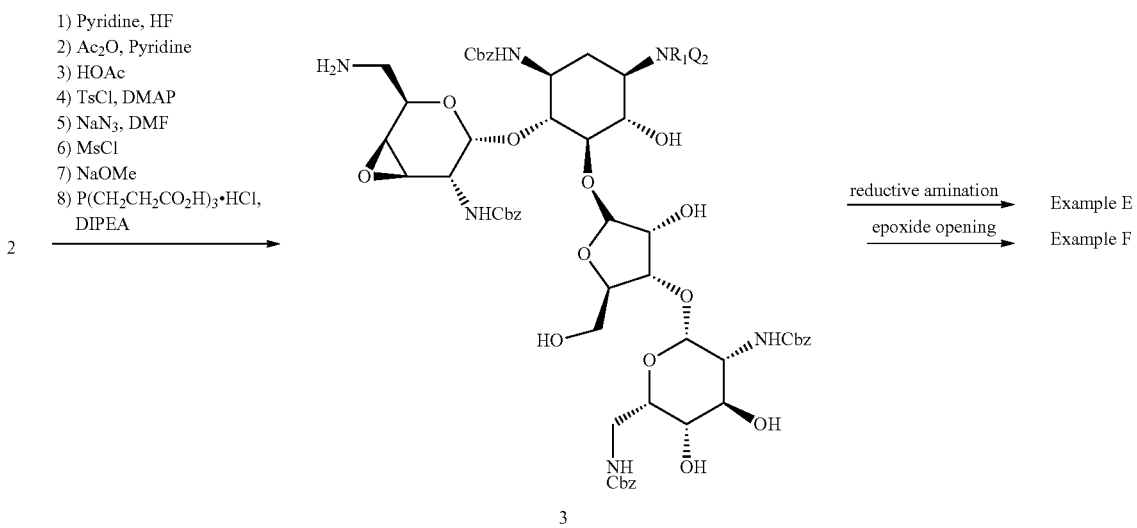
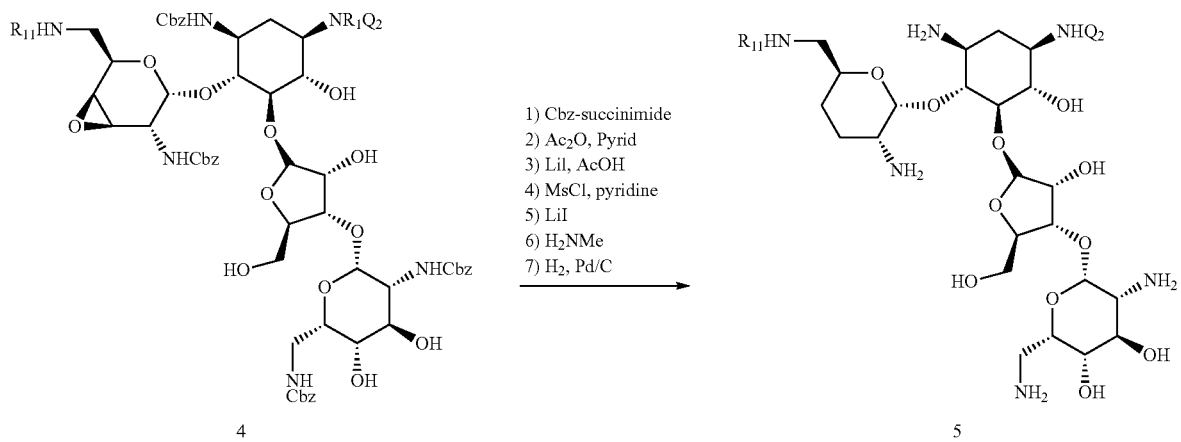

Example A
N-1 Acylation
Method A:
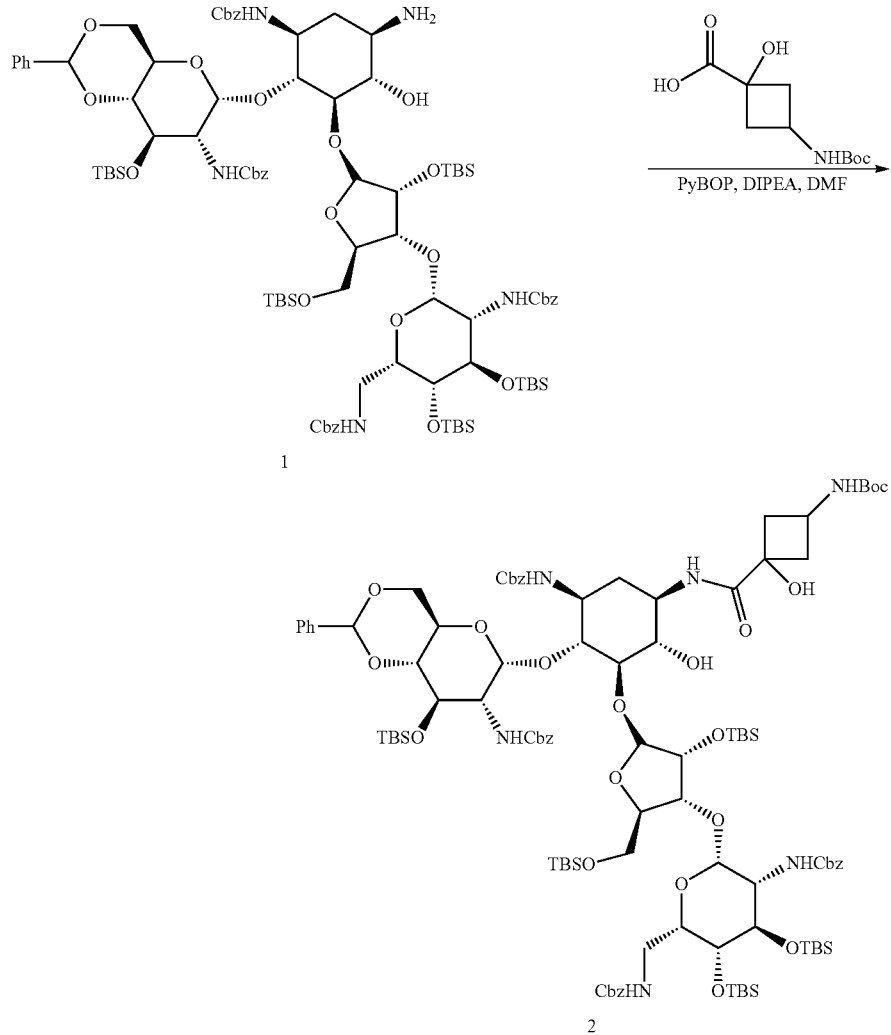
Method B:
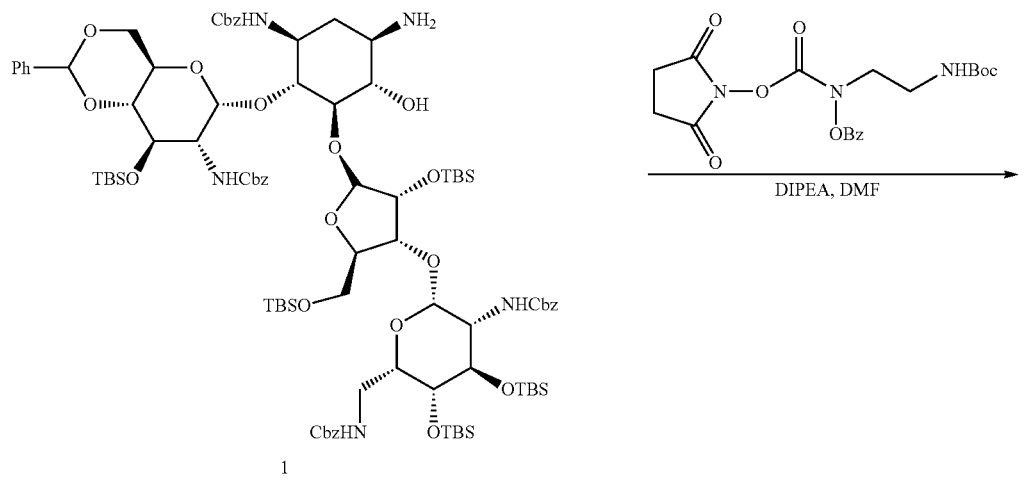

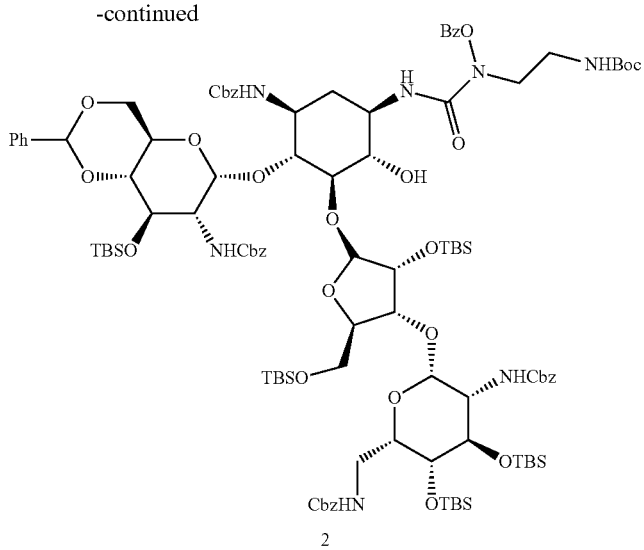
2
Example B
N-1 Epoxide Opening
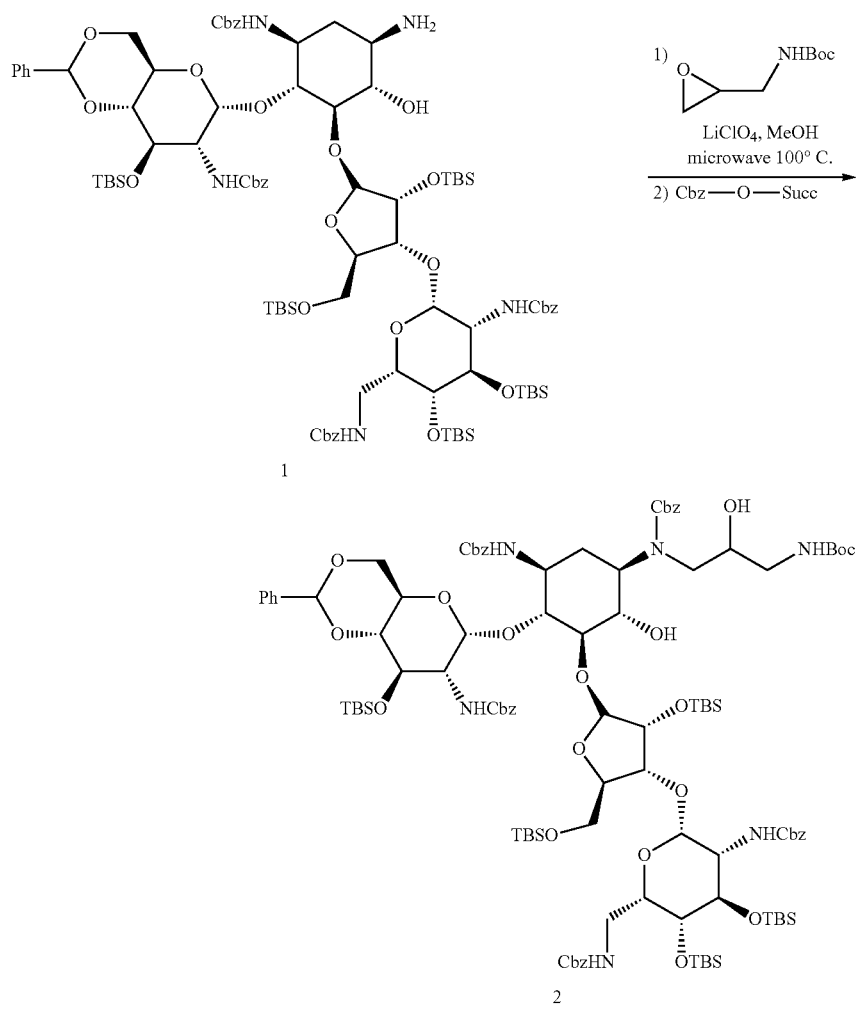

Example C
N-1 Sulfonylation
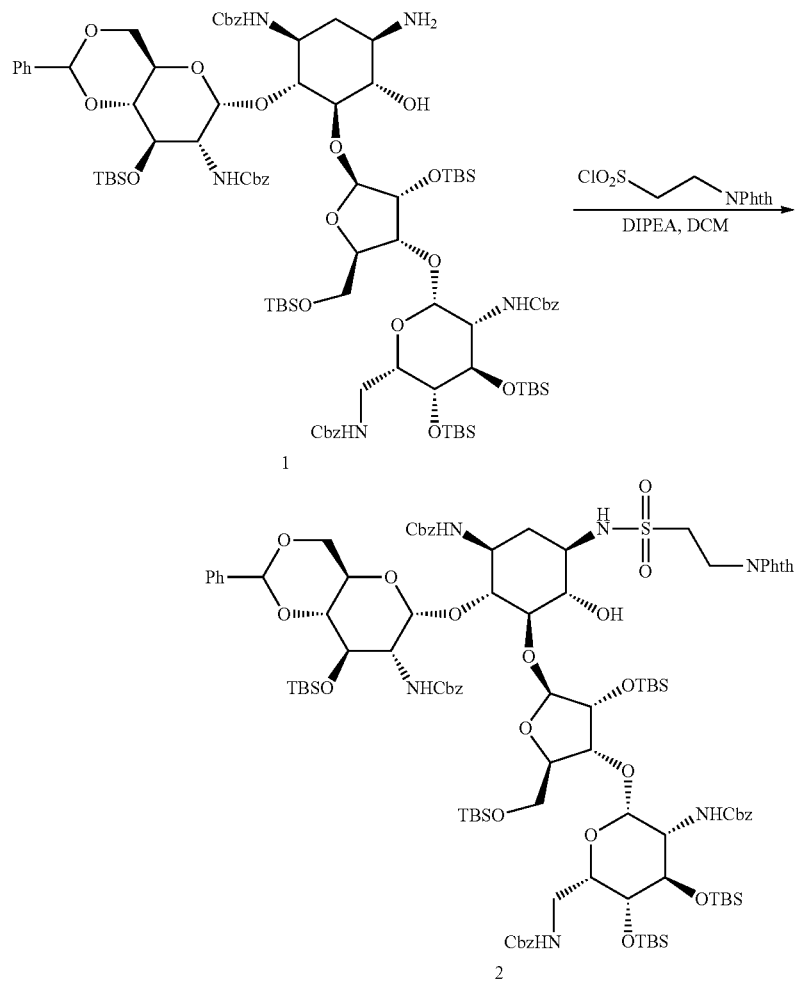
Example D
N-1 Reductive Amination
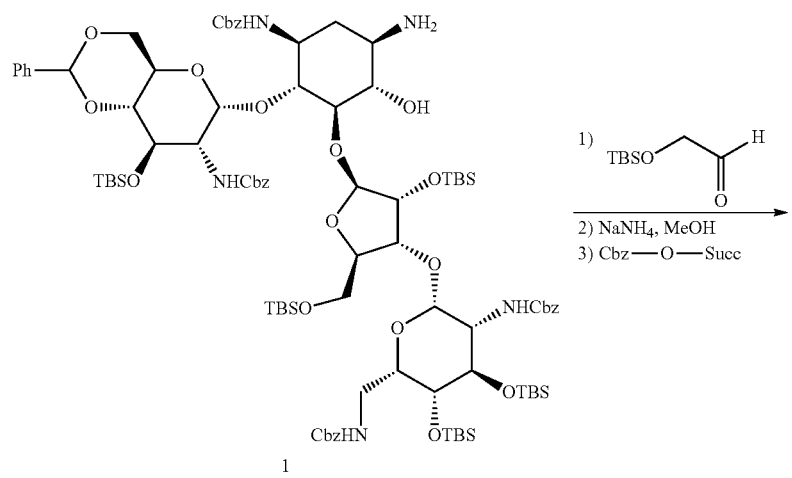

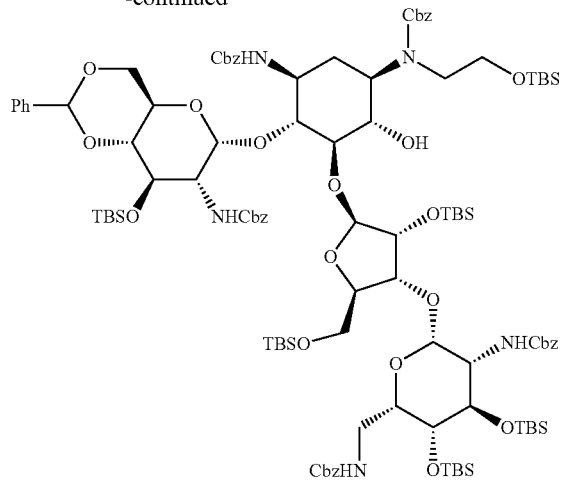
2
Example E
N-6' Reductive Amination
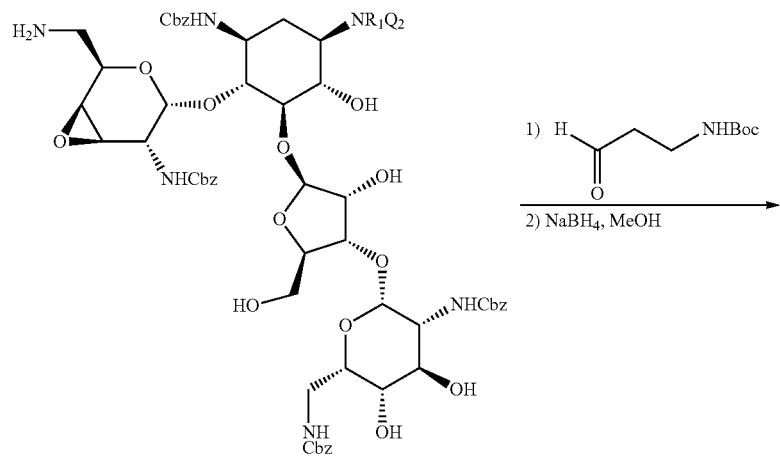
3
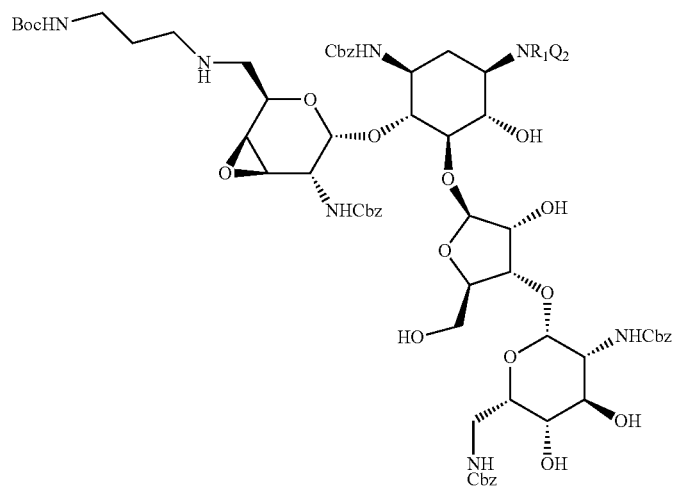
4

Example F
N-6' Epoxide Opening
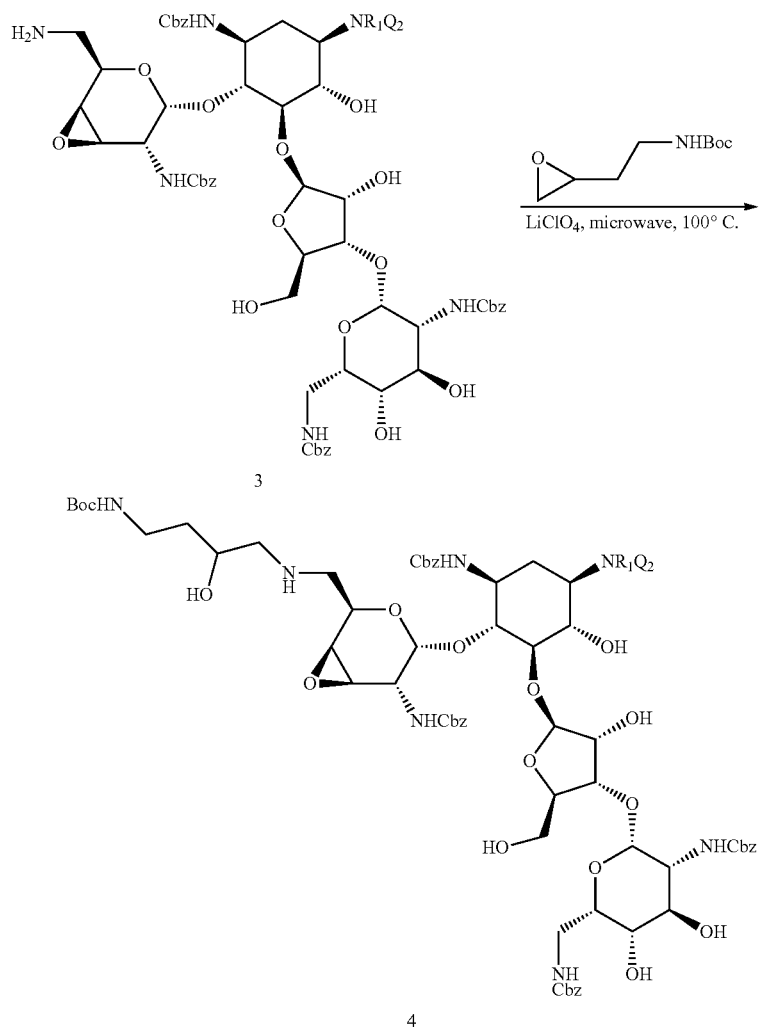
Example G
N-6' Amination
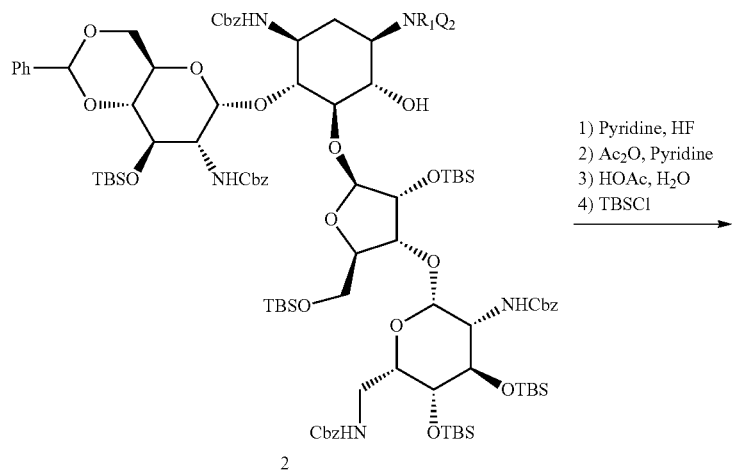

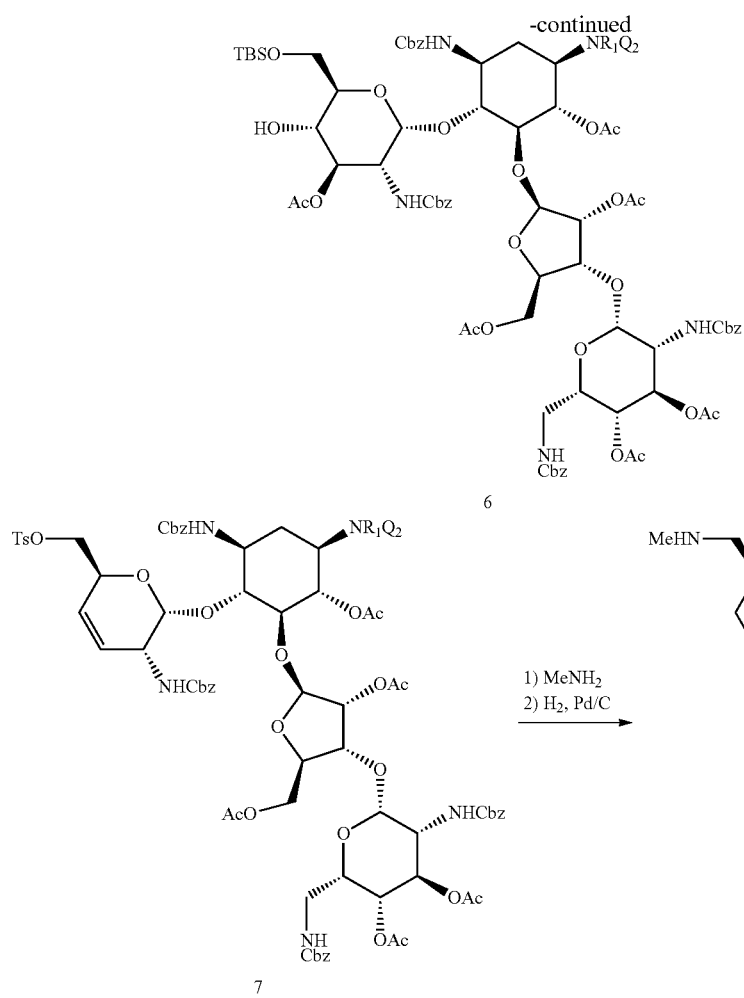
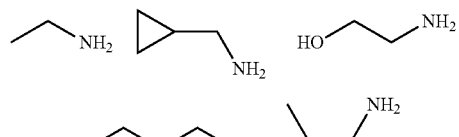
REPRESENTATIVE COUPLING REAGENTS
Representative N-1 Coupling Reagents
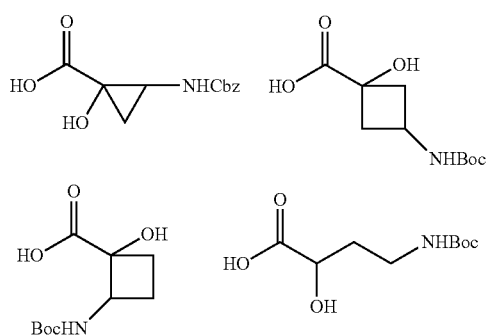

-continued
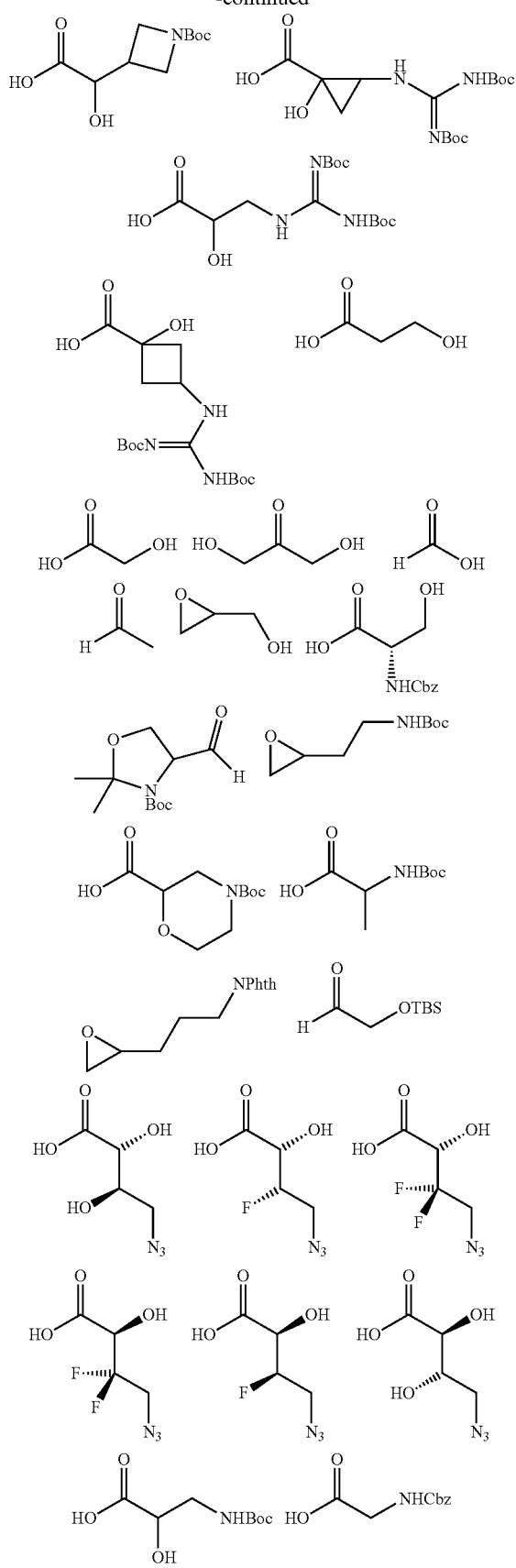
Representative N-6' Coupling Reagents
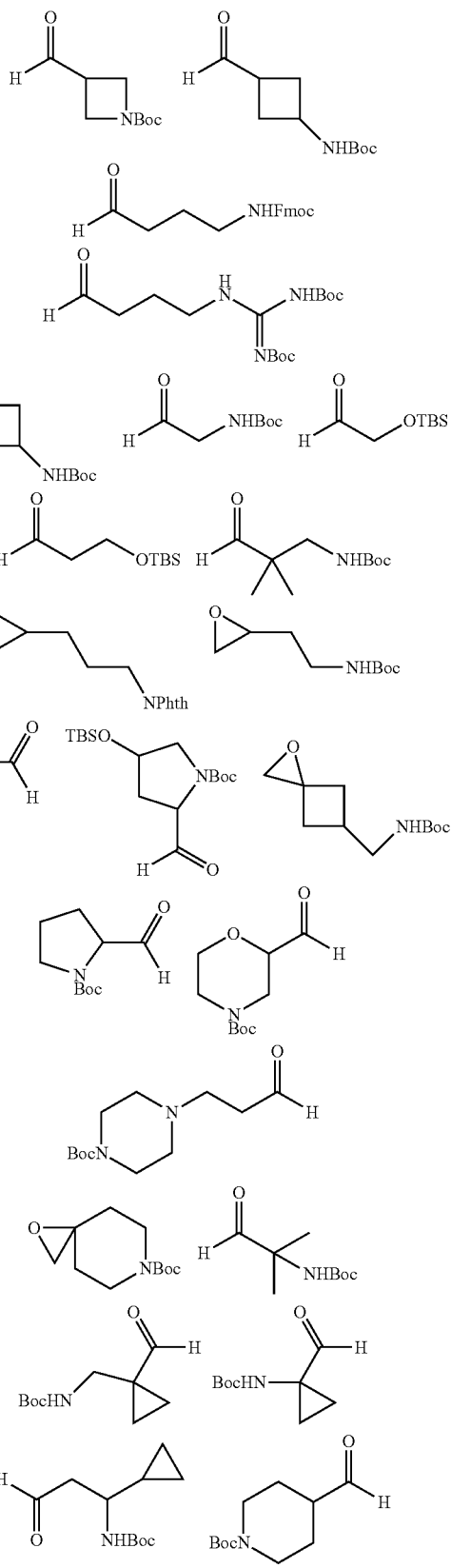

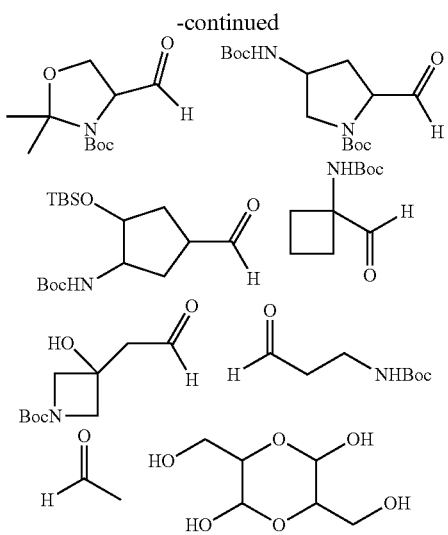

GENERAL SYNTHETIC PROCEDURES

Procedure 1: Reductive Amination

Method A: To a stirring solution of the aminoglycoside derivative (0.06 mmol) in MeOH (2 mL) was added the aldehyde (0.068 mmol), silica supported cyanoborohydride (0.1 g, 1.0 mmol/g), and the reaction mixture was heated by microwave irradiation to 100° C. (100 watts power) for 15 minutes. The reaction was checked by MS for completeness, and once complete all solvent was removed by rotary evaporation. The resulting residue was dissolved in EtOAc (20 ml), and washed with 5% NaHCO$_3$ (2×5 mL), followed by brine (5 mL). The organic phase was then dried over Na$_2$SO$_4$, filtered and the solvent was removed by rotary evaporation.

Method B: To a solution of aminoglycoside derivative (0.078 mmol) in DMF (1 ml) were added 3 Å molecular sieves (15-20), followed by the aldehyde (0.15 mmol) and the reaction was shaken for 2.5 hours. The reaction was checked by MS for completeness and, if needed, more aldehyde (0.5 eq) was added. The reaction mixture was then added dropwise to a stirring solution of NaBH$_4$ (0.78 mmol) in MeOH (2 mL) at 0° C., and the reaction was stirred for 1 hour. The reaction was diluted with H$_2$O (2 mL) and EtOAc (2 ml). The organic layer was separated and the aqueous layer was extracted with EtOAc (3×3 mL). The combined organic layers were dried over Na$_2$SO$_4$, filtered and concentrated to dryness.

Procedure 2: Boc Deprotection (tert-butyl dimethyl silyl Protecting Group is Removed Under These Conditions)

Important: Before Boc deprotection a sample must be dried well by pumping at high vacuum for 3 h.

Method A: To a stirring solution of the Boc protected aminoglycoside (0.054 mmol) in DCM or MeOH (1 mL) were added 3 Å molecular sieves (4-6), and trifluoroacetic acid (0.6 mL). The reaction was stirred at room temperature for 1 h, and checked for completeness by MS. Upon completion the reaction mixture was diluted with ether (15 mL) to induce precipitation. The vial was centrifuged and the supernatant was decanted. The precipitate was washed with ether (2×15 ml), decanted and dried under vacuum.

Procedure 3: PyBOP Coupling

To a stirring solution of aminoglycoside derivative (0.078 mmol) in DMF (1 mL) at −40° C. was added the acid (0.16 mmol), followed by PyBOP (0.16 mmol) and DIPEA (0.31 mmol) and the reaction was stirred. The reaction mixture was diluted with EtOAc (3 mL) and H$_2$O (3 mL), and the aqueous layer was separated and extracted with EtOAc (3×3 mL). The combined organic layers were dried over Na$_2$SO$_4$ and concentrated to dryness.

Procedure 4: Epoxide Opening

To a stirring solution of the aminoglycoside derivative (0.06 mmol) in MeOH (2 mL) was added the epoxide (0.07 mmol), LiClO$_4$ (0.15 mmol), and the reaction mixture was heated by microwave irradiation to 100° C. for 90 minutes. The reaction progress was monitored by MS. Upon completion, the solvent was removed by rotary evaporation. The resulting residue was dissolved in EtOAc (20 mL), washed with H$_2$O (2×5 mL) and brine (5 mL), dried over Na$_2$SO$_4$, filtered and concentrated to dryness.

Procedure 5: Phthalimido Deprotection

To a stirring solution of the phthalimido protected aminoglycoside (0.064 mmol) in EtOH (3 mL) was added hydrazine (0.32 mmol), and the reaction mixture was heated to reflux for 2 h. The reaction progress was monitored by MS. Upon cooling to room temperature, the cyclic by-product precipitated and was removed by filtration. The filtrate was concentrated to dryness to yield a residue, which was dissolved in EtOAc (20 mL), washed with 5% NaHCO$_3$ (2×5 mL) and brine (5 mL), dried over Na$_2$SO$_4$, filtered and concentrated to dryness.

Procedure 6: Sulfonylation

To a stirring solution of the aminoglycoside (0.067 mmol) in DCM (3 mL) was added DIPEA (0.128 mol) and the sulfonyl chloride (0.07 mmol). The reaction mixture was stirred at room temperature and its progress was monitored by MS. Once complete, the solvent was removed by rotary evaporation and the residue was dissolved in ethyl acetate (20 mL), washed with 5% NaHCO$_3$ (2×5 mL) and brine (5 mL), dried over Na$_2$SO$_4$, filtered and concentrated to dryness.

Procedure 7: N-Boc Protection

To a stirring solution of the amine (4.64 mmol) in THF (10 mL) was added 1N NaOH (10 mL), followed by Boc-anhydride (5.57 mmol) and the reaction progress was checked by MS. Once complete, the THF was removed by rotary evaporation and water (40 mL) was added. The aqueous phase was separated and extracted with Et$_2$O (2×30 ml). The aqueous phase was acidified to pH 3 by the addition of dilute H$_3$PO$_4$ and was then extracted with EtOAc (2×60 ml). The combined organic layers were washed with H$_2$O (2×30 mL) and brine (30 mL), dried over Na$_2$SO$_4$, filtered and concentrated to dryness.

Procedure 8: Syntheses of Epoxides

To a stirring solution of the alkene (5.16 mmol) in chloroform (20 mL) at 0° C. was added m-chloroperbenzoic acid (8.0 mmol) and the reaction mixture was stirred for 30 minutes at 0° C. and was then allowed to warm to room temperature. The reaction progress was monitored by MS and TLC, and additional portions of m-CPBA were added as needed. Upon completion, the reaction mixture was diluted with chloroform (50 mL) and washed with 10% aq. Na$_2$SO$_3$ (2×30 mL), 10% aq. NaHCO$_3$ (2×50 mL) and brine (50 mL). The organic layer was dried over Na$_2$SO$_4$, filtered and concentrated to yield a crude product, which was purified by flash choromatography (silica gel/hexanes:ethyl acetate 0-25%).

Procedure 9: General Procedure for Synthesis of α-hydroxy carboxylic acids

Step #1. O-(Trimethylsilyl)cyanohydrines: A 50-mL flask equipped with a magnetic stirring bar and drying tube was charged with the ketone or aldehyde (0.010 mmol), followed by THF (50 mL), trimethylsilyl cyanide (1.39 g, 14 mmol), and zinc iodide (0.090 g, 0.28 mmol), and the reaction mixture was stirred at room temperature for 24 hr. Solvent evaporation gave a residue, which was dissolved in EtOAc (60 mL), washed with 5% aq. NaHCO$_3$ (2×30 mL), H$_2$O (30 mL), and brine (30 mL), dried over Na$_2$SO$_4$, filtered and concentrated to dryness to yield a crude, which was carried through to the next step without further purification.

Step #2. Acid hydrolysis to α-hydroxy carboxylic acid: AcOH (25 ml) and conc. HCl (25 ml) were added to the unpurified material from step #1 and the reaction mixture was refluxed for 2-3 hr. The reaction mixture was then concentrated to dryness to give a white solid, which was carried through to the next step without further purification.

Step #3. Boc protection: To a stirring solution of solid from step #2 in 2 M NaOH (20 mL) and i-PrOH (20 mL) at 0° C. was added Boc$_2$O (6.6 g, 3 mmol) in small portions, and the reaction mixture was allowed to warm to room temperature over 4 h. i-PrOH was then evaporated, and H$_2$O (50 mL) was added, and the aqueous phase was separated and extracted with Et$_2$O (2×30 ml). The aqueous layer was acidified to pH 3 by addition of dilute H$_3$PO$_4$ and was extracted with EtOAc (2×60 ml). The combined organic layers were washed with H$_2$O (2×30 mL) and brine (30 mL), dried over Na$_2$SO$_4$, filtered and concentrated to yield the desired N-Boc-α-hydroxy carboxylic acids in 56-72% yield.

Procedure 10: Protection of Amine by Fmoc Group

To a stirring solution of the amine (0.049 mol) in DCM (100 mL), was added DIPEA (16 mL, 0.099 mol) and the reaction mixture was cooled to 0° C. Fmoc-Cl (12.8 g, 0.049 mol) was then added portion-wise over several minutes, and the reaction was allowed to warm to room temperature for 2 hr. The organic layer was washed with water (2×50 mL) and brine (50 mL), dried over Na$_2$SO$_4$, filtered and concentrated to dryness to yield the Fmoc protected amine (90-95% yield).

Procedure 11: Synthesis of Aldehydes via TEMPO/Bleach Oxidation

To a vigorously stirring solution of the alcohol (1.54 mmol) in DCM (4 mL) was added TEMPO (0.007 g, 0.045 mmol, 0.03 mol %) and a 2M aqueous KBr solution (75 mL, 0.15 mmol, 10 mol %) and the reaction mixture was cooled to −10° C. In a separate flask NaHCO$_3$ (0.5 g, 9.5 mmol) was dissolved in bleach (25 mL, Chlorox 6.0% NaOCl) to yield a 0.78 M buffered NaOCl solution. This freshly prepared 0.78 M NaOCl solution (2.3 mL, 1.8 mmol, 117 mol %) was added to the reaction mixture over 5 min and the reaction was stirred for an additional 30 min at 0° C. The organic phase was separated and the aqueous layer was extracted with dichloromethane (2×4 mL). The combined organic layers were washed with 10% aq. Na$_2$S$_2$O$_3$ (4 mL), sat. aq. NaHCO$_3$ (2×4 mL), brine (5 mL), dried over Na$_2$SO$_4$ and concentrated to dryness.

Procedure 12: Synthesis of Alcohols Via Borane Reduction

To a stirring solution of the acid (1.5 mmol) in THF (5 mL) at −10° C. was slowly added 1.0 M BH$_3$-THF (2.98 mL, 2.98 mmol). The reaction mixture was stirred vigorously for an additional 3 min at −10° C., and was then allowed to warm to room temperature overnight. The reaction was quenched by the dropwise addition of a solution of HOAc/H$_2$O (1:1 v/v, 2.0 mL). The THF was removed by rotary evaporation and sat. aq. NaHCO$_3$ (15 mL) was added. The aqueous layer was extracted with DCM (3×5 mL) and the combined organic layers were washed with sat. aq. NaHCO$_3$ (2×5 mL), brine (10 mL), dried over Na$_2$SO$_4$, filtered and concentrated to dryness.

Procedure 13: Ozonolysis and Pinnick Oxidation

The substrate olefin (0.5 to 0.75 mmol) was dissolved in DCM (30 mL) and the reaction was cooled to −78° C. Ozone was bubbled through until a blue color persisted (3 to 5 min), and the reaction was stirred for 1 hr. Argon was then bubbled through to remove excess ozone for 10 minutes. The reaction was further quenched by the addition of dimethyl sulfide (10 equiv.), and was stirred for 30 min with warming to rt. The solvent was reduced under vacuum to yield the crude aldehyde, which was dried under high-vacuum for 10 min, and used without further purification. To a stirring solution of the aldehyde in THF, tBuOH and H$_2$O (3:3:2, 10 mL), was added NaH$_2$PO$_4$ (4 equiv.) followed by 2-methyl-2-butene (10 equiv.) and sodium chlorite (2 equiv.), and the reaction was stirred for 4 hr. The reaction mixture was then added to sat. aq. NaCl (10 mL) and extracted with DCM (3×). The combined organic layers were dried over Na$_2$SO$_4$, filtered and reduced under vacuum to yield a crude, which was purified by flash chromatography (silica gel, 0→0.5 or 1% MeOH/DCM).

GENERAL PURIFICATION PROCEDURES

Method #1: Purification by Basic Condition

Mobile Phases:
  A—Water with 10 mM NH$_4$OH
  B—Acetonitrile with 10 mM NH$_4$OH Columns:
  A: Waters-XBridge Prep Shield RP18 Column
    19×250 mm, 5 µm
    Gradient: 20 min at 0%, then 0-20% in 200 min at a flow of 20 ml/min
  B: Waters-XBridge Prep Shield RP18 Column
    50×100 mm, 5 µm
    Gradient: 20 min at 0%, then 0-20% in 200 min at a flow of 20 ml/min Method #2: Purification by Acidic Condition Mobile Phases:
  A—Water with 0.1% TFA
  B—Acetonitrile with 0.1% TFA Columns:
  A: Phenomenex Luna C18
    21.4×250 mm, 10 µm
    Gradient: 0-100%, flow 25 ml/min
  B: Phenomenex Luna C18
    50×250 mm, 10 µm
    Gradient: 0-100%, flow 45 ml/min

REPRESENTATIVE INTERMEDIATES

N,N'-bis-Cbz-2(S)-hydroxy-4-guanidino-butyric acid

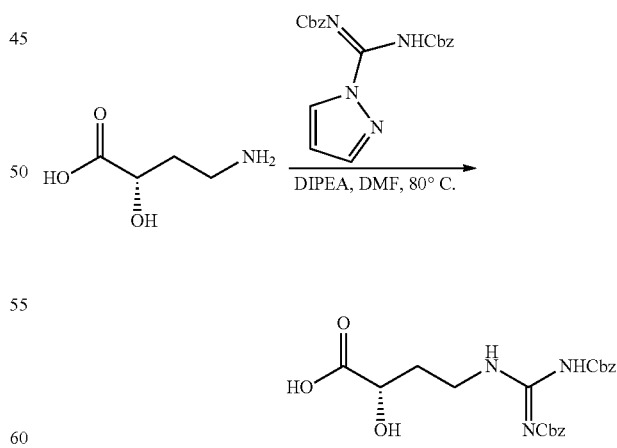

To a stirring solution of 2(S)-hydroxy-4-amino-butyric acid (0.059 g, 0.50 mmol) in DMF (2 ml) was added N,N'-bis(benzyloxycarbonyl)-1H-pyrazole-1-carboxamidine (0.26 g, 0.70 mmol) followed by DIPEA (0.87 mL, 4.99 mmol) and the reaction was heated to 80° C. and stirred overnight. The crude mixture was purified on a 2-inch reverse-phase HPLC column to yield N,N'-bis-Cbz-2(S)-hydroxy-4-guanidino-butyric acid: MS: m/z (M+H)+ calcd. 430.15, found 430.1.

Benzyl-2-(benzoyloxyamino)ethyl carbamate

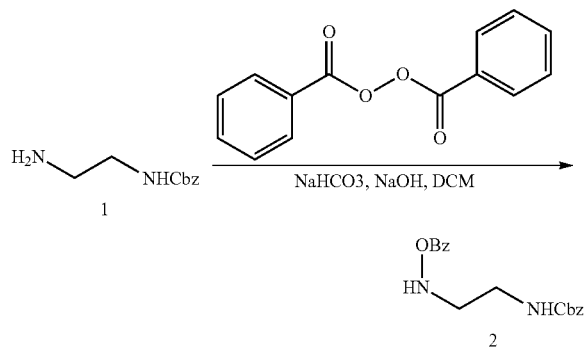

To a solution of benzyl-N-(2-aminoethyl)carbamate chloride salt (1, 540 mg, 2.34 mmol) in sat. aq. NaHCO$_3$ (45 mL) was added 1 M NaOH (15 mL) and the reaction was stirred vigorously. DCM (30 mL) was added, followed by benzoylperoxide (1.13 g, 4.68 mmol) and the reaction was stirred overnight. The organic layer was separated and washed with brine, dried over MgSO$_4$, filtered and concentrated to a crude, which was purified on a 1-inch reverse-phase HPLC column to yield benzyl-2-(benzoyloxyamino)ethyl carbamate (2, 252 mg, 0.80 mmol, 34.2%): MS: m/z (M+H)+ calc. 315.13, obs. 315.0.

Succinimidyl benzoyloxy(2-Cbz-aminoethyl)carbamate

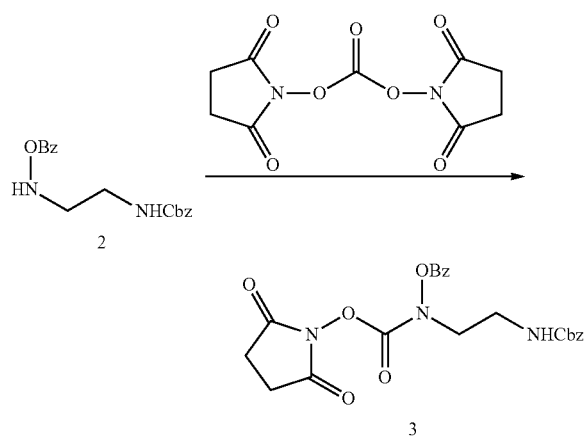

To a stirring solution of disuccinimidyl carbonate (525 mg, 2.05 mmol) in CH$_3$CN (16 mL) was added benzyl-2-(benzoyloxyamino)ethyl carbamate (2, 252 mg, 0.80 mmol) as a solution in CH$_3$CN (12 mL) over 4 hours, and the reaction was stirred overnight. Additional disuccinimidyl carbonate (251 mg, 0.98 mmol) was added and the reaction was heated at 60° C. overnight. Solvent removal gave a crude, which was purified on a 2-inch reverse-phase HPLC column to yield succinimidyl benzoyloxy(2-Cbz-aminoethyl)carbamate (3, 81 mg, 0.18 mmol, 22.5% yield).

N-Boc-3-amino-2(S)-hydroxy-propionic acid

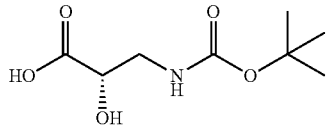

To a stirring solution of S-isoserine (4.0 g, 0.038 mol) in dioxane: H$_2$O (100 mL, 1:1 v/v) at 0° C. was added N-methylmorpholine (4.77 mL, 0.043 mol), followed by Boc$_2$O (11.28 mL, 0.049 mol) and the reaction was stirred overnight with gradual warming to room temperature. Glycine (1.0 g, 0.013 mol) was then added and the reaction was stirred for 20 min. The reaction was cooled to 0° C. and sat aq. NaHCO$_3$ (75 mL) was added. The aqueous layer was washed with ethyl acetate (2×60 mL) and then acidified to pH 1 with NaHSO$_4$. This solution was then extracted with ethyl acetate (3×70 mL) and these combined organic layers were dried over Na$_2$SO$_4$, filtered and concentrated to dryness to give the desired N-Boc-3-amino-2(S)-hydroxy-propanoic acid (6.30 g, 0.031 mmol, 81.5% yield): $^1$H NMR (400 MHz, CDCl$_3$) δ 7.45 (bs, 1 H), 5.28 (bs, 1 H), 4.26 (m, 1 H), 3.40-3.62 (m, 2 H), 2.09 (s, 1 H), 1.42 (s, 9 H); $^{13}$C NMR (100 MHz, CDCl$_3$) δ 174.72, 158.17, 82, 71.85, 44.28, 28.45.

N-Boc-4-amino-2(S)-hydroxy-butyric acid

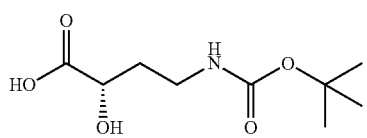

To a stirring solution of S-4-amino-2-hydroxy-butyric acid (51.98 g, 0.44 mol) in dioxane: H$_2$O (2 L, 1:1 v/v) was added K$_2$CO$_3$ (106 g, 0.91 mol) followed by a solution of Boc-anhydride (100 g, 0.46 mol) in dioxane (100 mL), and the reaction was stirred overnight. The reaction was washed with DCM (2×300 mL), and the aqueous layer was acidified to pH 2 with H$_3$PO$_4$. The aqueous layer was extracted with DCM (2×300 mL), and the combined organic layers were dried over MgSO$_4$, filtered and concentrated to dryness to yield the desired N-Boc-4-amino-2(S)-hydroxybutyric acid (48.2 g, 50% yield).

N-Boc-3-amino-propanal

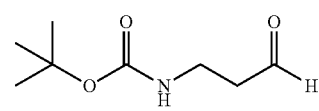

To a stirring solution of 3-(Boc-amino)-1-propanol (25 mL, 0.144 mol) in water saturated DCM (1.0 L) was added Dess-Martin reagent (99.2 g, 233.9 mmol) and the reaction mixture was stirred for 1 hour. The reaction was then diluted with ether (1.0 L), followed by a solution of Na$_2$S$_2$O$_3$ (250 g) in 80% NaHCO$_3$ (450 g in 1.0 L H$_2$O). The reaction was stirred vigorously for 30 minutes until two layers formed, the top layer was clear. The reaction was filtered to remove the precipitated solids and the aqueous layer was extracted with ether (1.0 L). The organic layer was washed with sat. NaHCO$_3$ (1.0 L), H$_2$O (1.0 L), and brine (1 L), dried over Na₂SO₄ and concentrated to a clear oil. The crude oil was dissolved in EtOAc:hexanes (1:1 v/v, 1.0 L) and filtered through a short silica gel column to yield the desired N-Boc-3-amino-propanal (21.7 g, 0.125 mol, 85.6% yield): ¹H NMR (400 MHz, CDCl₃) δ 9.77 (s, 1 H, CHO), 4.85 (bs, 1 H, NH), 3.36-3.42 (m, 2 H, CH₂), 2.67 (t, 2 H, CH₂), 1.39 (s, 9 H, (CH₃)₃).

N-Boc-1-oxa-6-azaspiro[2.5]octane

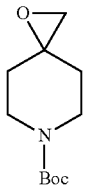

N-Boc-4-Methylene-piperidine (0.222 g, 1.12 mmol) was submitted to Procedure 8 to form the desired N-Boc-1-oxa-6-azaspiro[2.5]octane (0.215 g, 1.01 mmol, 90.2% yield): ¹H NMR (250 MHz, DMSO-d₆) δ 3.29-3.61 (m, 6 H), 1.56-1.70 (m, 2 H), 1.30-1.54 (m, 11 H).

2-(Pent-4-enyl)-isoindoline-1,3-dione

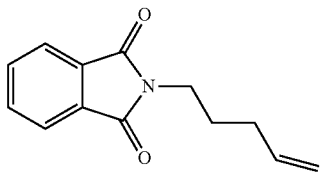 [SMILES: C=CCCCN1C(=O)c2ccccc2C1=O]

To a stirring solution of 5-bromo-pentene (6.0 g, 0.040 mol) in DMF (30 mL) was added K₂CO₃ (4.7 g, 0.034 mol) and potassium phthalimide (6.21 g, 0.033 mmol) and the reaction mixture was heated at 100° C. for 1 hr. The reaction mixture was cooled to room temperature, and water (50 mL) was added. The aqueous layer was then extracted with ethyl acetate (2×50 mL), and the combined organic layers were washed with 5% aq. NaHCO₃ (2×20 mL), brine (30 mL) and dried over Na₂SO₄. Filtration and solvent evaporation gave an oil, which was purified by flash chromatography (silica gel/hexanes:ethyl acetate 0-35%) to yield the desired 2-(pent-4-enyl)-isoindoline-1,3-dione as a solid (6.36 g, 0.029 mmol, 72.5% yield): MS m/e [M+H]⁺ calcd 216.1, found 216.1; NMR (250 MHz, DMSO-d₆) δ 7.79-7.95 (m, 4 H), 5.70-5.91 (m, 1 H), 4.90-5.11 (m, 2 H), 3.58 (t, 2 H), 1.98-2.10 (m, 2 H), 1.59-1.78 (m, 2 H).

2-(3-(Oxiran-2-yl)-propyl)-isoindoline-1,3-dione

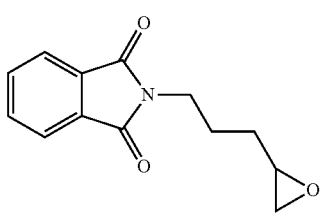 [SMILES: O=C1c2ccccc2C(=O)N1CCCC1CO1]

2-(Pent-4-enyl)-isoindoline-1,3-dione (6.36 g, 0.029 mmol) was submitted to Procedure 8 for epoxide formation to yield 2-(3-(oxiran-2-yl)-propyl-isoindoline-1,3-dione (5.8 g, 0.025 mmol, 86.2% yield): MS m/e [M+H]⁺ calcd 232.1, found 232.1; ¹H NMR (250 MHz, DMSO-d₆) δ 7.75-7.90 (m, 4 H, Ar), 3.52 (t, 2 H, CH₂), 2.87-2.96 (m, 1 H, CH), 2.70 (t, 1 H), 2.30-2.45 (m, 1 H), 1.36-1.80 (m, 4 H).

N-Boc-3-hydroxypyrrolidine-3-carboxylic acid

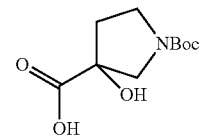

N-Boc-3-pyrrolidone (0.010 mmol) was submitted to Procedure 9 to yield the desired N-Boc-3-hydroxy-pyrrolidine-3-carboxylic acid.

N-Boc-1-amino-but-3-ene

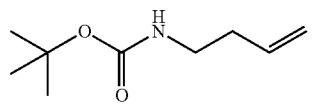

3-Buten-1-amine (4.93 g, 0.069 mol) was submitted to Procedure 7 for Boc protection to yield a crude, which was purified by flash chromatography (silica gel/hexanes:ethyl acetate 0-30%) to yield N-Boc-1-amino-but-3-ene (6.47 g, 0.038 mol, 55.1% yield).

N-Boc-2-(oxiran-2-yl)-ethyl carbamate

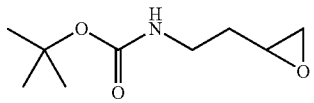

N-Boc-1-amino-but-3-ene (6.47 g, 0.038 mol) was submitted to Procedure 8 for epoxide formation to yield a crude, which was purified by flash chromatography (silica gel/hexanes:ethyl acetate 0-45%) to yield N-Boc-2-(oxiran-2-yl)-ethyl carbamate (6.0 g, 0.032 mol, 84.2% yield): ¹H NMR (250 MHz, DMSO-d₆) δ 2.98-3.09 (m, 2 H), 2.83-2.92 (m, 1 H), 2.65 (t, 1 H), 2.42 (dd, 1 H), 1.44-1.66 (m, 2 H), 1.36 (s, 9 H, (CH₃)₃).

N-Boc-3-hydroxy-azetidin-3-carboxylic acid

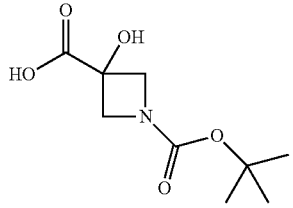

N-Boc-3-azetidinone (21.9 g, 0.128 mol) was submitted to Procedure 9 to yield the desired N-Boc-3-hydroxy-azetidin-3-carboxylic acid (18.7 g, 0.086 mol, 67.0% yield): MS m/e [M+H]⁺ calcd 218.1, found 218.2.

3-Methylene-1-methylamino-cyclobutane

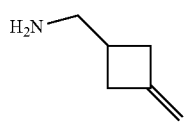

To a stirring solution of 3-methylene-1-cyano-cyclobutane (2.5 g, 0.026 mol) in THF (35 ml) at 0° C. was slowly added 2M LiAlH₄ (22 mL, 0.044 mmol) and the reaction was allowed to warm to room temperature. The reaction was then quenched by the addition of sat. aq. NH₄Cl (10 mL), and THF (10 mL). The organic layer was separated and concentrated to dryness to yield a residue, which was dissolved in ethyl acetate (100 mL). The organic layer was washed with 5% NaHCO₃ (2×20 mL), brine (20 mL), dried over Na₂SO₄, filtered and concentrated to yield the desired 3-methylene-1-methylamino-cyclobutane as an oil, which was carried through to the next step without further purification.

3-Methylene-1-N-Boc-methylamino-cyclobutane

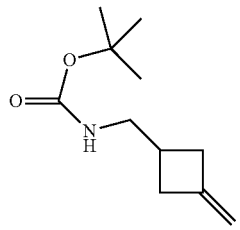

To a stirring solution of 3-methylene-1-methylamino-cyclobutane (2.52 g, 0.026 mol) in 1N NaOH (15 ml) and THF (15 mL), was added Boc₂O (6.7 g, 0.030 mol) and the reaction mixture was stirred overnight. THF was evaporated and the aqueous layer was extracted with ethyl acetate (2×40 mL). The combined organic layers were washed with 5% NaHCO₃ (2×20 mL) brine (20 mL), dried over Na₂SO₄, filtered and concentrated to dryness to yield a crude, which was purified by flash chromatography (silica gel/hexanes:ethyl acetate 0%-60%) to yield the desired 3-methylene-1-N-Boc-methylamino-cyclobutane (1.9 g, 0.0096 mol, 36.9% yield): ¹H NMR (250 MHz, DMSO-d₆) δ 6.88 (bs, 1 H), 4.72 (s, 2 H), 2.95-3.05 (m, 2 H), 2.56-2.71 (m, 2 H), 2.21-2.40 (m, 3 H), 1.20 (s, 9 H).

N-Boc-1-oxaspiro[2.3]hexan-5-yl-methanamine

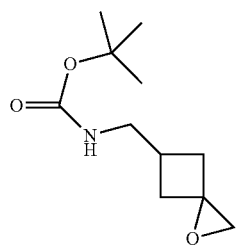

3-Methylene-1-N-Boc-methylamino-cyclobutane (1.9 g, 0.0096 mol) was submitted to Procedure 8 for epoxide formation to yield N-Boc-1-oxaspiro[2.3]hexan-5-yl-methanamine (1.34 g, 6.27 mol, 65.3% yield): ¹H NMR (250 MHz, DMSO-d₆) δ 2.99-3.10 (m, 2 H), 2.60-2.66 (m, 2 H), 1.99-2.47 (m, 5 H), 1.40 (s, 9 H).

N-Fmoc-4-amino-butyraldehyde diethyl acetal

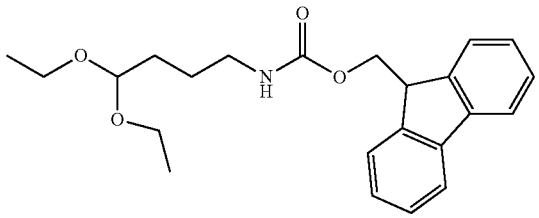 [SMILES: CCOC(CCCNC(=O)OCC1c2ccccc2-c2ccccc21)OCC]

4-Amino-butyraldehyde diethyl acetal (8.0 g, 0.050 mol) was Fmoc protected following Procedure 10 to give the desired N-Fmoc-4-amino-butyraldehyde diethyl acetal (22.08 g, MS m/e [M+Na]⁺ calcd 406.2, found 406.1), which was carried through to the next step without further purification.

N-Fmoc-4-amino-butyraldehyde

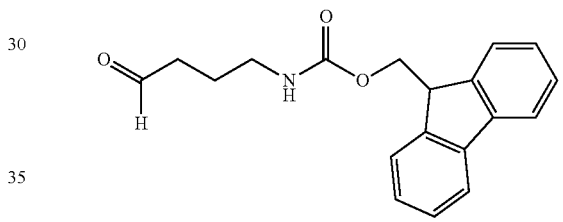

To a stirring solution of N-Fmoc-4-amino-butyraldehyde diethyl acetal (0.050 mmol) in 1,4-dioxane (100 mL) was added aq. HCl (100 ml, 1:1 v/v, H₂O:conc. HCl) and the reaction progress was monitored by MS. Upon completion, the organic solvent was removed by rotary evaporation, and the aqueous layer was extracted with ethyl acetate (2×200 mL). The combined organic layers were washed with 5% NaHCO₃ (2×75 mL), brine (75 mL), dried over Na₂SO₄, filtered and concentrated to dryness to yield the desired N-Fmoc-4-amino-butyraldehyde (15.35 g, 0.049 mol, 90.0% yield), which was carried through to the next step without further purification: MS m/e [M+Na]⁺ calcd 332.1, found 332.0.

3-Methylene-cyclobutane carboxylic acid

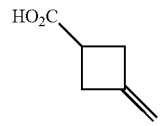

To a stirring solution of KOH (70.0 g, 1.25 mol) in EtOH/H₂O (500 mL, 1:1 v/v) was added 3-methylenecyclobutane carbonitrile (25.0 g, 0.26 mol) and the reaction mixture was refluxed for 6 h. The reaction progress was monitored by TLC and, upon completion, the mixture was cooled and acidified to pH 3-4 with HCl. The ethanol was evaporated, and the remaining aqueous layer was extracted with Et₂O (200 mL).

The organic layer was washed with water (2×20 mL), brine (30 ml), dried over Na$_2$SO$_4$, filtered and concentrated to dryness to yield 3-methylene-cyclobutane carboxylic acid, which was carried through to the next step without further purification: $^1$H NMR (250 MHz, CDCl$_3$) δ 10.75 (bs, 1 H), 4.80 (s, 2 H), 2.85-3.26 (m, 5 H).

N-Boc-3-Methylene-cyclobutanamine

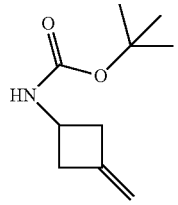

To a stirring solution of 3-methylene-cyclobutane carboxylic acid (1.0 g, 8.9 mmol) in THF (90 mL) was added NaN$_3$ (2.0 g, 31.1 mmol), followed by tetrabutyl ammonium bromide (0.48 g, 1.5 mmol) and Zn(OTf)$_2$ (0.1 g, 0.3 mmol), and the reaction mixture was heated to 40° C. Boc$_2$O (2.1 g, 9.8 mmol) was then added at once, and the reaction was heated at 45° C. overnight. The reaction was then cooled to 0° C. and was quenched with 10% aq. NaNO$_2$ (180 mL). The THF was evaporated and the aqueous layer was extracted with EtOAc (180 mL). The organic layer was washed with 5% aq. NaHCO$_3$ (2×20 mL), brine (30 ml), dried over Na$_2$SO$_4$, filtered and concentrated to dryness to yield a crude, which was purified by flash chromatography (silica gel/hexanes:ethyl acetate: 0-90%) to yield the desired N-Boc-3-methylene-cyclobutanamine (0.57 g, 3.1 mmol, 34.9% yield): $^1$H NMR (250 MHz, CDCl$_3$) δ 4.83 (s, 2 H), 4.79 (bs, 1 H), 4.05-4.23 (m, 1 H), 2.92-3.11 (m, 2 H), 2.50-2.65 (m, 2 H), 1.44 (s, 9 H).

N-Boc-1-oxaspiro[2.3]hexan-5-amine

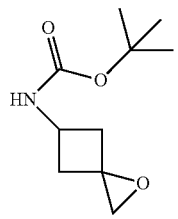

N-Boc-3-methylene-cyclobutanamine (1.65 g, 9.0 mmol) was submitted to Procedure 8 for epoxide formation to yield N-Boc-1-oxaspiro[2.3]hexan-5-amine (1.46 g, 7.33 mmol, 81.5% yield): $^1$H NMR (250 MHz, CDCl$_3$) δ 4.79 (bs, 1 H), 4.13-4.31 (m, 1 H), 2.66-2.83 (m, 4 H), 2.31-2.47 (m, 2 H), 1.45 (s, 9 H).

N-Boc-2,2-dimethyl-3-amino-propionaldehyde

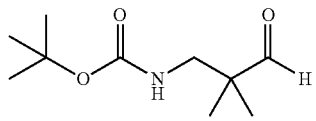

N-Boc-3-amino-2,2-dimethyl propanol (0.415 g, 2.04 mmol) was submitted to Procedure 11 to yield N-Boc-2,2-dimethyl-3-amino-propionaldehyde (0.39 g, 1.94 mmol, 95.1% yield): $^1$H NMR (250 MHz, CDCl3) δ 9.42 (s, 1 H), 4.80 (bs, 1 H), 3.11 (d, 2 H), 1.39 (s, 9 H), 1.06 (s, 6 H).

N-Boc-3-amino-3-cyclopropyl propionaldehyde

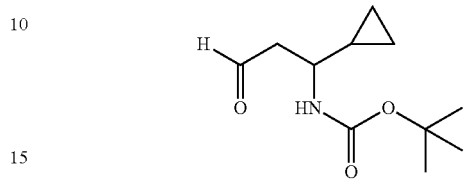

N-Boc-3-amino-3-cyclopropyl-propanol (0.130 g, 0.60 mmol) was submitted to Procedure 11 for oxidation to the corresponding N-Boc-3-amino-3-cyclopropyl propionaldehyde, which was carried through to the next step without further purification.

4(S)-tert-Butyldimethylsilyloxy-N-Boc-pyrrolidin-2(R)-carboxaldehyde

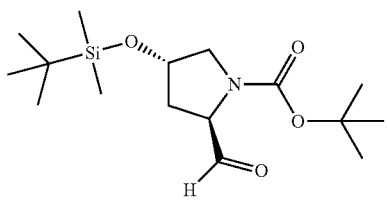 [SMILES: CC(C)(C)OC(=O)N1C[C@@H](O[Si](C)(C)C(C)(C)C)C[C@@H]1C=O]

4(S)-tert-Butyldimethylsilyloxy-N-Boc-pyrrolidin-2(R)-methanol (0.50 g, 1.50 mmol) was submitted to Procedure 11 for oxidation to the corresponding 4(S)-tert-butyldimethylsilyloxy-N-Boc-pyffolidin-2(R)-carboxaldehyde, which was carried through to the next step without further purification.

3-tert-Butyldimethylsilyloxy-propanal

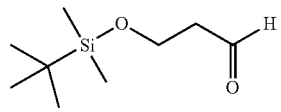

3-tert-Butyldimethylsilyloxy-propanol (0.50 g, 2.62 mmol) was submitted to Procedure 11 for oxidation to the corresponding 3-tert-butyldimethylsilyloxy-propanal, which was carried through to the next step without further purification.

2-Methyl-N-Boc-2-amino-propanal

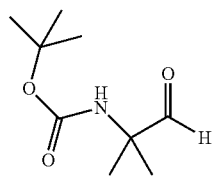

2-Methyl-N-Boc-2-amino-propanol (0.83 g, 4.38 mmol) was submitted to Procedure 11 for oxidation to the corresponding 2-methyl-N-Boc-2-amino-propanal (0.706 g, 3.77 mmol, 86.1% yield): $^1$H NMR (250 MHz, CDCl$_3$) δ 9.40 (s, 1 H), 1.57 (s, 1 H), 1.41 (s, 9 H), 1.30 (s, 6 H).

N-Boc-1-amino-cyclobutane carboxylic acid

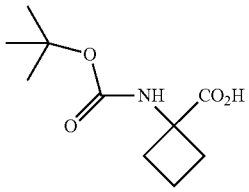

1-Amino-cyclobutane carboxylic acid ethyl ester (1.0 g, 6.28 mmol) was dissolved in 1N HCl (10 mL) and the reaction was heated to a reflux for 2 hours. The reaction mixture was then concentrated to dryness to yield a crude which was submitted to Procedure 7 for Boc protection to yield the desired N-Boc-1-Amino-cyclobutane carboxylic acid.

N-Boc-1-amino-cyclobutyl-methanol

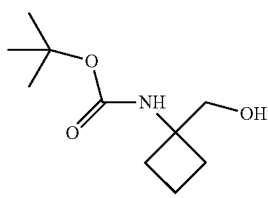

N-Boc-1-amino-cyclobutane carboxylic acid (6.28 mmol) was submitted to Procedure 12 for reduction to the corresponding N-Boc-1-Amino-cyclobutyl-methanol.

N-Boc-1-amino-cyclobutane carboxaldehyde

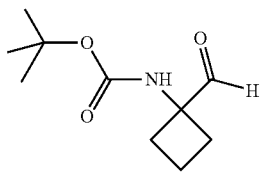

N-Boc-1-amino-cyclobutyl-methanol (0.25 g, 1.24 mmol) was submitted to Procedure 11 to yield the corresponding N-Boc-1-amino-cyclobutane carboxaldehyde (0.24 g, 1.20 mmol, 96.8% yield): $^1$H NMR (250 MHz, CDCl$_3$) δ 9.0 (s, 1 H), 4.91 (bs, 1 H), 3.74 (bs, 2 H), 1.71-2.20 (m, 4 H), 1.42 (s, 9 H).

N-Boc-3-amino-cyclobutanone

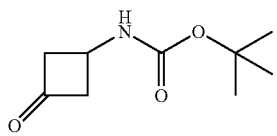

To a vigorously stirring solution of N-Boc-3-methylene-cyclobutanamine (9.8 g, 53.5 mmol) in DCM (160 mL) and H$_2$O (160 mL) was added K$_2$CO$_3$ (3 g, 21.7 mmol), followed by NaIO$_4$ (35 g, 163.5 mmol), tetrabutylammonium chloride (0.2 g, 0.72 mmol) and RuCl$_3$ (0.6 g, 7.6 mmol). During the course of the reaction, the organic solution turned dark brown, the catalyst turned black, while the upper aqueous layer turned white. The reaction was monitored by TLC, and upon completion, the reaction mixture was filtered through a pad of celite. The filtrates were transferred to a separatory funnel, and the aqueous layer was extracted with DCM (2×50 mL). The combined organic layers were washed with 5% NaHCO$_3$ (2×30 mL), brine (30 mL), dried over Na$_2$SO$_4$, filtered and evaporated to dryness to yield a crude, which was purified by flash chromatography (silica gel/hexanes:ethyl acetate 0-60%) to yield the desired N-Boc-3-amino-cyclobutanone (7.13 g, 38.53 mmol, 72% yield): NMR (250 MHz, CDCl$_3$) δ 4.88 (bs, 1 H), 4.13-4.29 (m, 1 H), 3.23-3.41 (m, 2 H), 2.9-3.05 (m, 2 H), 1.39 (s, 9 H).

N-Boc-1-hydroxy-3-amino-cyclobutyl-carboxylic acid

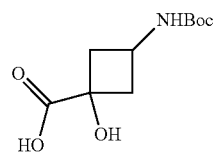 [SMILES: CC(C)(C)OC(=O)NC1CC(O)(C(=O)O)C1]

N-Boc-3-amino-cyclobutanone (7.13 g, 38.53 mmol) was submitted to Procedure 9 to yield the desired N-Boc-1-hydroxy-3-amino-cyclobutyl-carboxylic acid (MS m/e [M+H]$^+$ calcd 232.1, found 232.2.

N,N-diBoc-4(S)-amino-2(S)-methanol-pyrrolidine

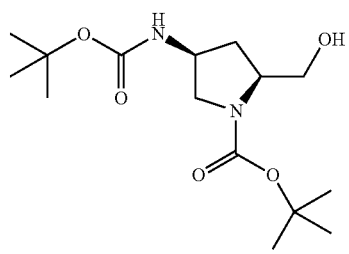 [SMILES: CC(C)(C)OC(=O)N[C@H]1C[C@@H](CO)N(C(=O)OC(C)(C)C)C1]

N,N-diBoc-4(S)-amino-pyrrolidine-2(S)-carboxylic acid (1.03 g, 3.12 mmol) was submitted to Procedure 12 to yield the corresponding N,N-diBoc-4(S)-amino-2(S)-methanol pyrrolidine (0.605 g, 1.91 mmol, 61.2% yield), which was carried through to the next step without further purification.

N,N-diBoc-4(S)-amino-pyrrolidine-2(S)-carbaldehyde

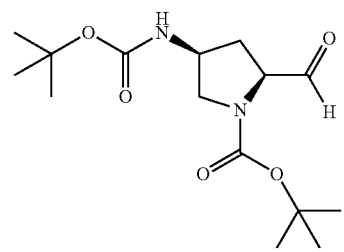 [SMILES: CC(C)(C)OC(=O)N[C@H]1C[C@@H](C=O)N(C(=O)OC(C)(C)C)C1]

N,N-diBoc-4(S)-amino-2(S)-methanol pyrrolidine (0.486 g, 1.53 mmol) was submitted to Procedure 11 for oxidation to the corresponding N,N-diBoc-4(S)-amino-pyrrolidine-2(S)-carbaldehyde, which was carried through to the next step without further purification.

N-Boc-1-aminomethyl-cyclopropyl-methanol

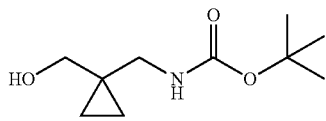

N-Boc-1-aminomethyl-cyclopropane carboxylic acid (1.0 g, 4.64 mmol) was submitted to Procedure 12 to yield the corresponding N-Boc-1-aminomethyl-cyclopropyl-methanol (0.99 g, MS m/e [M+H]+ calcd 202.1, found 202.1), which was carried through to the next step without further purification.

N-Boc-1-aminomethyl-cyclopropane carboxaldehyde

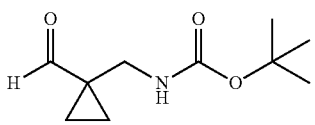

N-Boc-1-aminomethyl-cyclopropyl-methanol (0.87 g, 4.32 mmol) was submitted to Procedure 11 for oxidation to the corresponding N-Boc-1-aminomethyl-cyclopropane carboxaldehyde, which was carried through to the next step without further purification.

N-Boc-1-amino-cyclopropyl-methanol

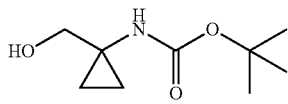

N-Boc-1-amino-cyclopropane carboxylic acid (0.25 g, 1.24 mmol) was submitted to Procedure 12 to yield the corresponding N-Boc-1-amino-cyclopropyl-methanol (0.051 g, 0.27 mmol, 21.8% yield), which was carried through to the next step without further purification.

N-Boc-1-amino-cyclopropane carboxaldehyde

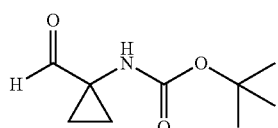

N-Boc-1-amino-cyclopropyl-methanol (0.051 g, 0.27 mmol) was submitted to Procedure 11 for oxidation to the corresponding N-Boc-1-amino-cyclopropane carboxaldehyde, which was carried through to the next step without further purification.

N-Boc-1(R)-amino-2(S)-tert-butyldimethylsilyloxy-cyclopentane-4(S)-carboxylic acid

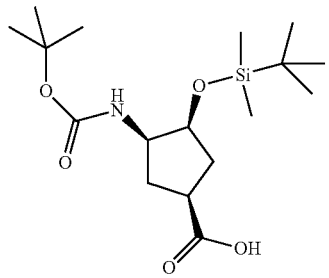 [SMILES: CC(C)(C)OC(=O)N[C@@H]1C[C@H](C(=O)O)C[C@@H]1O[Si](C)(C)C(C)(C)C]

To a stirring solution of N-Boc-1(R)-amino-2(S)-hydroxy-cyclopentane-4(S)-carboxylic acid methyl ester (0.622 g, 2.40 mmol) in DCM (1.9 mL) was added imidazole (0.164 g, 2.41 mmol), DMAP (0.047 g, 0.35 mmol) and TBSCl (0.363 g, 2.40 mmol) and the reaction was stirred at room temperature for 18 hours, followed by heating at 40° C. for 1 hour. The reaction mixture was cooled to room temperature, and was quenched with $H_2O$ (3 mL). The organic layer was separated and was concentrated to dryness to yield a residue, which was dissolved in isopropanol (6 mL) and 1M NaOH (2.9 mL), and the reaction was heated at 60° C. for 1 hour. The reaction was cooled to 0° C. and slowly acidified to pH 3 with 1M HCl (3 mL). After adding chloroform (18 mL), the organic layer was separated, dried over $Na_2SO_4$, and concentrated to dryness to yield the desired acid (0.75 g, 2.09 mmol, 87.1% yield).

N-Boc-1(R)-amino-2(S)-tert-butyldimethylsilyloxy-4(S)-hydroxymethyl-cyclopentane

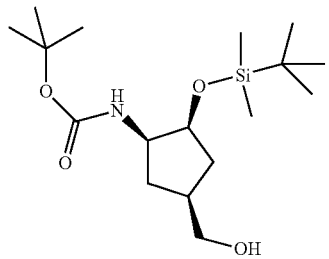 [SMILES: CC(C)(C)OC(=O)N[C@@H]1C[C@H](CO)C[C@@H]1O[Si](C)(C)C(C)(C)C]

N-Boc-1(R)-amino-2(S)-tert-butyldimethylsilyloxy-cyclopentane-4(S)-carboxylic acid (0.53 g, 1.47 mmol) was submitted to Procedure 12 for reduction to the corresponding N-Boc-1(R)-amino-2(S)-tert-butyldimethylsilyloxy-4(S)-hydroxymethyl-cyclopentane (0.44 g, 1.27 mmol, 86.4% yield): $^1$H NMR (250 MHz, $CDCl_3$) δ 4.69-4.79 (m, 1 H), 4.08-4.13 (m, 1 H), 3.88 (bs, 1 H), 3.52-3.61 (m, 2 H), 2.16-2.30 (m, 2 H), 1.96-2.14 (m, 2 H), 1.48-1.53 (m, 2 H), 1.47 (s, 9 H), 0.91 (s, 9 H), 0.09 (s, 6 H).

N-Boc-1(R)-amino-2(S)-tert-butyldimethylsilyloxy-cyclopentane-4(S)-carboxaldehyde

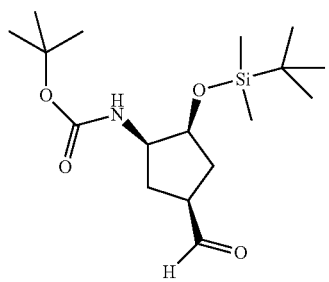 [SMILES: CC(C)(C)OC(=O)N[C@@H]1C[C@H](C=O)C[C@@H]1O[Si](C)(C)C(C)(C)C]

N-Boc-1(R)-amino-2(S)-tert-butyldimethylsilyloxy-4(S)-hydroxymethyl-cyclopentane (0.44 g, 1.27 mmol) was submitted to Procedure 11 for oxidation to the corresponding N-Boc-1(R)-amino-2(S)-tert-butyldimethylsilyloxy-cyclopentane-4(S)-carboxaldehyde (0.42 g, 1.22 mmol, 96.1% yield).

tert-Butyl-2-(N-Boc-3-hydroxy-azetidin-3-yl)acetate

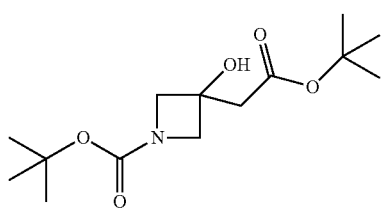 [SMILES: CC(C)(C)OC(=O)CC1(O)CN(C(=O)OC(C)(C)C)C1]

To a stirring solution of N-Boc-3-azetidinone (0.45 g, 2.64 mmol) in THF (5 mL) was slowly added a 0.5 M solution of 2-tert-butoxy-2-oxoethyl-zinc chloride in Et$_2$O (10 mL, 5.0 mmol), and the reaction mixture was stirred for 5 h. The reaction was then quenched with sat. aq. NH$_4$Cl (10 mL), and the aqueous layer was separated and extracted with ethyl acetate (2×30 mL). The combined organic layers were washed with 5% aq. NaHCO$_3$ (2×10 mL), brine (15 mL), dried over Na$_2$SO$_4$, filtered and concentrated to dryness to yield tert-butyl-2-(N-Boc-3-hydroxy-azetidin-3-yl)-acetate (MS m/e [M+H]$^+$ calcd 288.2, found 287.7).

2-(N-Boc-3-hydroxy-azetidin-3-yl)-acetic acid

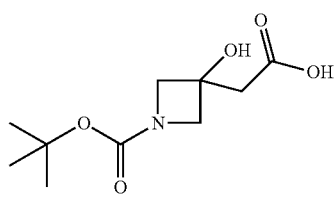 [SMILES: CC(C)(C)OC(=O)N1CC(O)(CC(=O)O)C1]

To a stirring solution of tert-butyl-2-(N-Boc-3-hydroxy-azetidin-3-yl)-acetate (0.86 g, 2.99 mmol) in dioxane (18 mL) was added 3 M HCl (5 mL), and the mixture was heated at 70° C. for 1 h. The reaction mixture was then cooled to 0° C. and it was basified with 2 M NaOH (8 mL), followed by addition of BOC$_2$O (1.0 g, 4.6 mmol). The reaction mixture was allowed to warm to room temperature for 2 h, and was then concentrated to half its total volume on the rotary evaporator. Isopropanol (3 mL) and chloroform (12 mL) were then added and the mixture was cooled to 0° C. and slowly acidified to pH 3 with 1M HCl. The organic layer was then separated, dried over Na$_2$SO$_4$, and concentrated to dryness to yield 2-(N-Boc-3-hydroxy-azetidin-3-yl)-acetic acid (0.65 g, 2.81 mmol, 94.0% yield).

N-Boc-3-(2-hydroxy-ethyl)-azetidin-3-ol

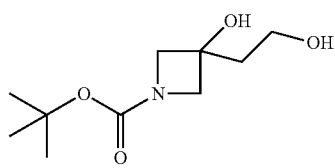

2-(N-Boc-3-hydroxy-azetidin-3-yl)-acetic acid (0.44 g, 1.90 mmol) was submitted to Procedure 12 for reduction to yield the corresponding N-Boc-3-(2-hydroxy-ethyl)-azetidin-3-ol (0.29 g, 1.33 mmol, 70.0% yield).

2-(N-Boc-3-hydroxy-azetidin-3-yl)-acetaldehyde

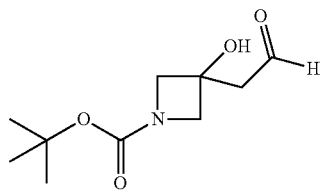

N-Boc-3-(2-hydroxy-ethyl)-azetidin-3-ol (0.29 g, 1.33 mmol) was submitted to Procedure 11 for oxidation to the corresponding 2-(N-Boc-3-hydroxy-azetidin-3-yl)-acetaldehyde, which was carried through to the next step without further purification.

N-Boc-3-hydroxymethyl-azetidine

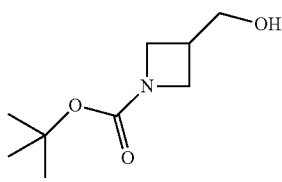

N-Boc-azetidine-3-carboxylic acid (1.94 g, 9.64 mmol) was submitted to Procedure 12 for reduction to the corresponding N-Boc-3-hydroxymethyl-azetidine, which was carried through to the next step without further purification.

N-Boc-azetidine-3-carboxaldehyde

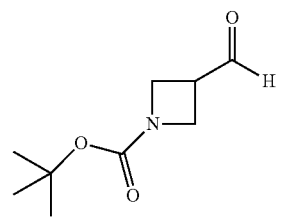

N-Boc-3-hydroxymethyl-azetidine (9.64 mmol) was submitted to Procedure 11 for oxidation to the desired N-Boc-azetidine-3-carboxaldehyde, which was carried through to the next step without further purification.

2-(N-Boc-azetidin-3-yl)-2-hydroxy-acetic acid

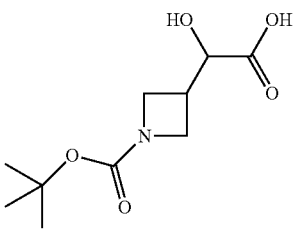 [SMILES: CC(C)(C)OC(=O)N1CC(C(O)C(=O)O)C1]

N-Boc-azetidine-3-carboxaldehyde (1.60 g, 8.64 mmol) was submitted to Procedure 9 to yield the desired 2-(N-Boc-azetidin-3-yl)-2-hydroxy-acetic acid (MS m/e [M+H]⁺ calcd 232.1, found 231.8).

Synthesis of (2R,3R)-4-azido-2-benzyloxy-3-fluorobutanoic acid (5)

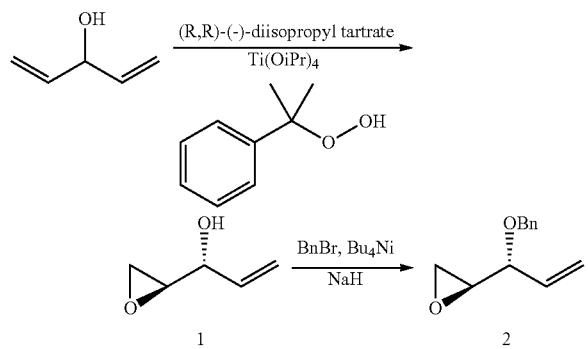

Molecular sieves (4 Å, 4 g) were added to a round bottom flask, and were activated by heating with a Bunsen burner under high vacuum. DCM (100 mL) was then added and the flask was cooled to −35° C. with a cryocooler. Titanium tetraisopropoxide (1.75 mL, 5.95 mmol) and (R,R)-(−)-diisopropyl tartrate (1.65 mL, 7.75 mmol) were added and the reaction was stirred for 30 min. Penta-1,4-dienol (5 g, 59.4 mmol) and excess cumene hydroperoxide (80%, 17.5 mL) were added in small portions, and stirring was continued at −35° C. for 48 hr. The reaction was quenched by addition of sat. aq. Na₂SO₄ (5 mL) immediately followed by Et₂O (50 mL) and the reaction was stirred for 2 hr with warming to rt. The reaction mixture was filtered through Celite, and washed with Et₂O. Solvent removal under vacuum without heating resulted in approximately 30 mL of a yellow solution. Excess cumene alcohol and hydroperoxide were removed by flash chromatography (silica gel, 40% Et₂O/hex). Finally solvent removal under vacuum without heating yielded a mixture of (2S,3R)-1,2-epoxy-4-penten-3-ol (1) (Rf=0.47, 1:1 EtOAc/hex) and diisopropyl tartrate (Rf=0.6), which was used in the next step without further purification.

To a stirring solution of epoxide (1) in THF (100 mL) under an argon atmosphere was added tetrabutylammonium iodide (2.2 g, 5.96 mmol), followed by benzyl bromide (8.6 mL, 71.9 mmol) and the reaction was cooled to −15° C. Sodium hydride (60% in mineral oil, 2.65 g, 66.1 mmol) was added in small portions and the reaction was stirred overnight with warming to rt. The reaction was quenched with MeOH, filtered through Celite, and washed with Et₂O, Solvent removal gave an oily residue which was purified by flash chromatography (silica gel, 5→10% Et₂O/hex) to yield (2S,3R)-1,2-epoxy-3-benzyloxy-4-pentene (2) as a clear non-volatile liquid (5.3 g, 47.6% yield): Rf=0.69 (1:4 EtOAc/hex); [α]_D=−36.7° (c 1.52, CHCl₃); HRMS (ESI) (M+H)⁺ calc. for C₁₂H₁₄O₂ 191.1067, obs. 191.1064; ¹H NMR (CDCl₃, 300 MHz) 7.38-7.33 (m, 5H), 5.92-5.78 (m, 1H), 5.41-5.39 (m, 1H), 5.37-5.33 (m, 1H), 4.66 (d, J=11.95 Hz, 1H), 4.49 (d, J=11.96 Hz, 1H), 3.83 (dd, J=7.34, 4.20 Hz, 1H), 3.10 (dt, J=4.07, 4.06, 2.70 Hz, 1H), 2.79 (dd, J=5.21, 4.00 Hz, 1H), 2.70 (dd, J=5.23, 2.64 Hz, 1H). ¹³C NMR (CDCl₃, 100 MHz) δ 138.32, 134.67, 128.56 (2C), 127.87 (2C), 127.82, 119.73, 79.54, 70.83, 53.41, 45.00.

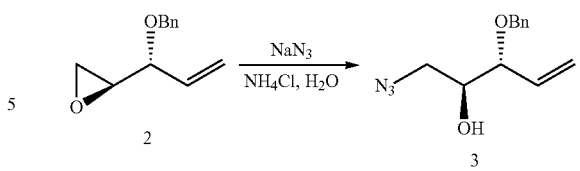

NaN₃ (3.38 g, 52 mmol) and NH₄Cl (2.78 g, 52 mmol) in H₂O (10 mL) were heated until a clear solution was obtained. This solution was then added dropwise to a solution of (2S,3R)-1,2-epoxy-3-benzyloxy-4-pentene (2) (3.3 g, 17.4 mmol) in MeOH (200 mL) and the reaction mixture was stirred for 4 days. The organic solvent Was removed under vacuum, and the aqueous layer was extracted with DCM (3×). The combined organic layers were dried over Na₂SO₄, filtered and reduced under vacuum to yield a crude, which was purified by flash chromatography (silica gel, 10→20% Et₂O/hex) to yield (2S,3R)-1-azido-3-benzyloxy-4-penten-2-ol (3) (2.66 g, 66% yield) as a non-volatile clear liquid: Rf=4.8 (1:4 EtOAc/hex); HRMS (ESI) (M+Na)⁺ calc. for C₁₂H₁₅N₃O₂ 256.1056, obs. 256.1057; [α]_D=−46.3° (c 1.50, CHCl₃); ¹H NMR (CDCl₃, 300 MHz) δ 7.42-7.28 (m, 5H), 5.91-5.76 (m, 1H), 5.46 (dd, J=17.16, 1.42 Hz, 1H), 5.42 (dd, J=24.00, 1.37 Hz, 1H), 4.65 (d, J=11.67 Hz, 1H), 4.39 (d, J=11.67 Hz, 1H), 3.88-3.80 (m, 2H), 3.44-3.40 (m, 2H), 2.22 (d, J=3.60 Hz, 1H); ¹³C NMR (CDCl₃, 100 MHz) δ 137.88, 134.60, 128.66 (2C), 128.08 (2C), 128.05, 121.40, 81.39, 72.61, 70.70, 53.0; FTIR (NaCl): 3435, 2870, 2102, 1642, 1454, 1070 cm⁻¹.

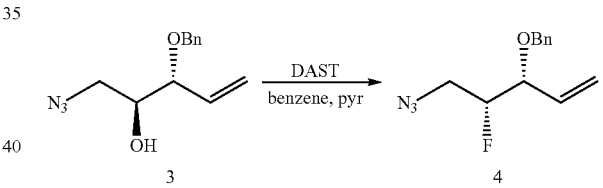

To a stirring solution of DAST (900 μL, 6.87 mmol) in benzene (3.2 mL) and pyridine (400 μL) in a plastic container at −10° C. was added (2S,3R)-1-azido-3-benzyloxy-4-penten-2-ol (3) (750 mg, 3.21 mmol) in small portions, and the reaction was stirred at this temperature for 48 hr followed by 6 hr at rt. The reaction mixture was slowly added to sat. aq. NaHCO₃ (20 mL) at 0° C. and was stirred for 10 min. The resulting aqueous mixture was extracted with DCM (3×) and the combined organic layers were washed with 2 N HCl, dried over MgSO₄, filtered and reduced under vacuum to yield a crude, which was purified by flash chromatography (silica gel, 1% Et₂O/hex) to yield (3R,4R)-5-azido-4-fluoro-3-benzyloxy-pent-1-ene (4) (128 mg, 16.9% yield) as a nonvolatile clear liquid: Rf=0.63 (1:9 EtOAC/Hex); [α]_D=−11.9° (c 1.50, CHCl₃); ¹H NMR (CDCl₃, 400 MHz) δ 7.44-7.29 (m, 5H), 4.63 (dddd, J=47.64, 7.07, 4.99, 3.32 Hz, 1H), 5.49-5.42 (m, 2H), 4.70 (d, J=11.95 Hz, 1H), 4.57 (ddd, J=7.07, 4.99, 3.32 Hz, 1H), 4.44 (d, J=11.90 Hz, 1H), 4.03 (ddd, J=16.87, 7.57, 5.04 Hz, 1H), 3.64-3.52 (m, 1H), 3.45 (ddd, J=27.45, 13.63, 3.27 Hz, 1H). ¹⁹F NMR (CDCl₃, 282 MHz)-196.66 (dddd, J=47.27, 27.08, 19.84, 16.89 Hz); ¹³C NMR (CDCl₃, 100 MHz) δ 137.80, 133.09 (d, J=5.30 Hz), 128.70 (2C), 128.09 (3C), 121.04, 93.33 (d, J=181.54 Hz), 79.08 (d, J=20.39 Hz), 70.92, 51.46 (d, J=22.25 Hz). FTIR (NaCl): 2930, 2104, 1643, 1454, 1281, 1115, 1069 cm⁻¹.

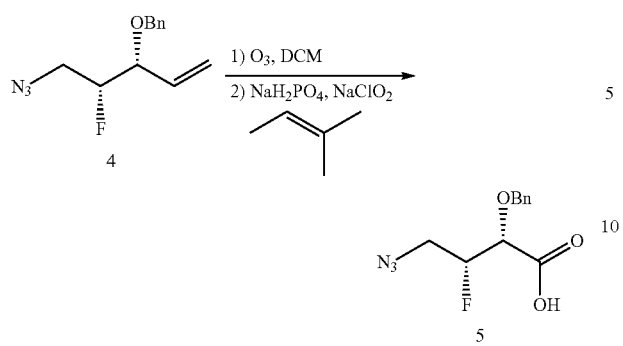

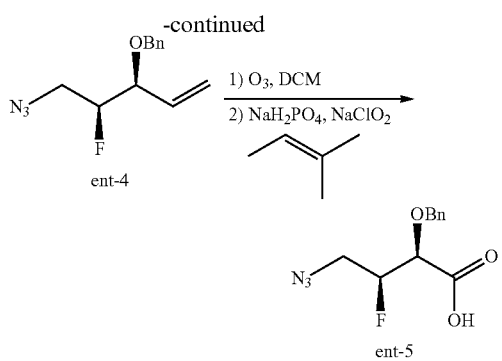

(3R,4R)-5-azido-4-fluoro-3-benzyloxy-pent-1-ene (4) (128 mg, 0.543 mmol) was submitted to Procedure 13, followed by recrystallization from hot hexanes (2×) to yield (2R,3R)-4-azido-2-benzyloxy-3-fluorobutanoic acid (5) (120 mg, 90%): [α]$_D$=−56.9° (c 0.68, CHCl$_3$); HRMS (ESI negative mode) (M−H) calc. for C$_{11}$H$_{12}$FN$_3$O$_3$ 252.0790, obs. 252.0782; $^1$H NMR (CDCl$_3$, 400 MHz) δ 10.55 (s, 1H), 7.46-7.34 (m, 5H), 4.98 (dddd, J=46.40, 7.57, 4.91, 2.92 Hz, 1H), 4.94 (d, J=11.47 Hz, 1H), 4.55 (d, J=11.51 Hz, 1H), 4.17 (dd, J=27.26, 2.86 Hz, 1H), 3.77 (dt, J=13.89, 13.66, 7.27 Hz, 1H), 3.42 (ddd, J=24.28, 13.20, 4.92 Hz, 1H); $^{19}$F NMR (CDCl$_3$, 376 MHz) δ −198.36 (dddd, J=46.28, 27.22, 24.46, 14.15 Hz); $^{13}$C NMR (CDCl$_3$, 100 MHz) δ 174.63 (d, J=4.21 Hz), 136.37, 129.15 (2C), 129.07, 128.98 (2C), 91.53 (d, J=182.59 Hz), 76.40 (d, J=19.90 Hz), 73.96 (s), 50.87 (d, J=25.13 Hz); FTIR (NaCl): 3151, 2098, 1753, 1407, 1283, 1112 cm$^{-1}$.

Synthesis of ent-5

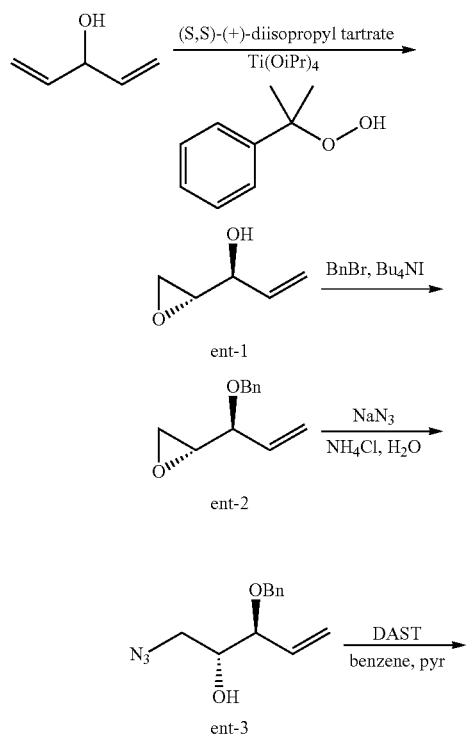

Starting from penta-1,4-dienol (5 g, 59.4 mmol) and using (S,S)-(+)-diisopropyl tartrate under the same reaction conditions as described above the enantiomer ent-2 was obtained (4.9 g, 43% yield): [α]$_D$=+35.7° (c 1.76, CHCl$_3$). (2R,3S)-1,2-Epoxy-3-benzyloxy-4-pentene (ent-2, 3.9 g, 20.5 mmol) was submitted to the same reaction conditions described above to yield the enantiomer (2R,3S)-1-azido-3-benzyloxy-4-penten-2-ol (ent-3, 2.75 g, 57% yield): [α]$_D$=+47.3° (c 1.30, CHCl$_3$). (2R,3S)-1-Azido-3-benzyloxy-4-penten-2-ol (ent-3) (500 mg, 2.14 mmol) was submitted to the same reaction conditions as described above to yield the enantiomer (3S,4S)-5-azido-4-fluoro-3-benzyloxy-pent-1-ene (ent-4, 75.5 mg, 0.32 mmol, 15% yield, [α]$_D$=+10.7°, c 1.50, CHCl$_3$), which was submitted to the same reaction conditions as described above to yield ent-5 (59 mg, 73% yield): [α]$_D$=+58.6° (c 0.73, CHCl$_3$).

Synthesis of (R)-4-Azido-3,3-difluoro-2-benzyloxy-butanoic acid (3)

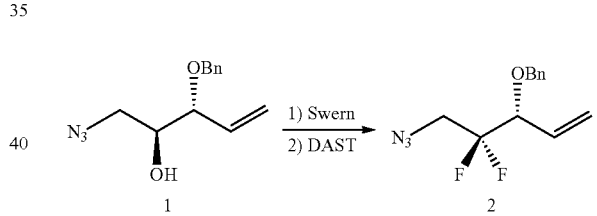

To a stirring solution of DMSO (690 μL, 9.65 mmol) in DCM (25 mL) at −78° C. was added oxalyl chloride (3.21 mL of a 2.0 M solution in DCM, 6.43 mmol) and the reaction was stirred for 1 hr. A solution of (2S,3R)-1-azido-3-benzyloxy-4-penten-2-ol (1) (750 mg, 3.21 mmol) in DCM (1 mL) was added dropwise and the reaction mixture was stirred for 1 hr at −78° C. N-Methyl morpholine (1.41 mL, 12.9 mmol) was added dropwise, and the reaction was stirred at −15° C. for 2 hr. The reaction was quenched with phosphate buffer (0.1 M, pH 6.0) and the aqueous layer was separated. The organic layer was washed with the phosphate buffer (3×), dried over Na$_2$SO$_4$, filtered and reduced under vacuum to give a brown residue. The residue was dissolved in Et$_2$O, dried over MgSO$_4$, filtered through a cotton plug, and reduced under vacuum to yield the crude ketone, which was dissolved in DCM (1 mL) and was added to a stirring solution of DAST (2 mL, 15.3 mmol) in DCM (3 mL) in a plastic vial at −25° C. The reaction was allowed to slowly warm to rt and was stirred for 48 hr. The reaction mixture was then slowly poured into stirring sat. aq. NaHCO$_3$ (20 mL) at 0° C., and was stirred for 10 min. The resulting aqueous mixture was extracted with DCM (3×), and the combined organic layers were dried over Na$_2$SO$_4$, filtered and reduced under vacuum to yield a crude, which was purified by flash chromatography (silica gel, 1% Et$_2$O/hex) followed by preparative TLC purification (silica gel, 0.5 mm, 5% Et₂O/hex) to yield (R)-5-azido-4,4-difluoro-3-benzyloxy-pent-1-ene (2, 193 mg, 0.76 mmol, 24% yield), as a non-volatile clear liquid: $R_f$=0.72 (1:4 EtOAc/hex); $[\alpha]_D$=−23.8° (c 1.52, CHCl₃); ¹H NMR (CDCl₃, 300 MHz) δ 7.44-7.31 (m, 5H), 5.89 (dddd, J=16.88, 10.61, 7.11, 0.62 Hz, 1H), 5.59-5.56 (m, 1H), 5.53 (d, J=10.74 Hz, 1H), 4.71 (d, J=11.67 Hz, 1H), 4.50 (d, J=11.66 Hz, 1H), 4.14 (td, J=14.25, 7.13, 7.13 Hz, 1H), 3.64 (tq, J=13.67, 13.67, 13.67, 11.19, 11.19 Hz, 2H); ¹⁹F NMR (CDCl₃, 282 MHz) δ −116.63 (dtd, J=257.62, 13.91, 13.90, 8.72 Hz), −111.27 (dtd, J=257.59, 16.18, 16.16, 7.04 Hz); ¹³C NMR (CDCl₃, 75 MHz) δ 137.14, 130.33 (t, J=3.06, 3.06 Hz), 128.71 (2C), 128.27, 128.20 (2C), 122.78, 120.69 (dd, J=249.89, 246.83 Hz), 78.87 (dd, J=30.35, 25.35 Hz), 71.48 (d, J=0.48 Hz), 51.47 (dd, J=30.26, 25.92 Hz); FTIR (NaCl): 2928, 2108, 1455, 1292, 1091 cm⁻¹.

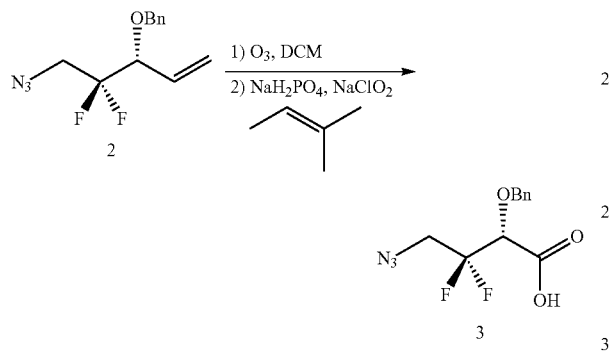

(R)-5-Azido-4,4-difluoro-3-benzyloxy-pent-1-ene (2, 193 mg, 0.76 mmol) was submitted to Procedure 13, followed by washing with cold hexanes (3×) at −20° C. to yield 3 (139 mg, 67.6% yield): $[\alpha]_D$=−32.4° (c 0.80, CHCl₃); HRMS (ESI negative mode) (M−H) for C₁₁H₁₁F₂N₃O₃ 270.0696, obs. 270.06924; ¹H NMR (CDCl₃, 400 MHz) δ 7.46-7.32 (m, 5H), 6.48 (s, 1H), 4.84 (d, J=11.30 Hz, 1H), 4.67 (d, J=11.30 Hz, 1H), 4.37 (dd, J=12.23, 9.78 Hz, 1H), 3.75 (dd, J=14.67, 12.35 Hz, 2H); ¹⁹F NMR (CDCl₃, 376 MHz) δ −112.61 (qd, J=260.95, 12.30, 12.29, 12.29 Hz), −109.68 (dtd, J=260.79, 14.75, 14.68, 9.94 Hz); ¹³C NMR (CDCl₃, 100 MHz) δ 170.84, 135.48, 129.01, 128.94 (2C), 128.78 (2C), 119.59 (t, J=251.58, 251.58 Hz), 76.56 (dd, J=29.86, 27.24 Hz), 74.34, 51.58 (dd, J=28.94, 26.76 Hz). FTIR (NaCl): 3337, 2929, 2112, 1738, 1455, 1292, 1210, 1119 cm⁻¹.

Synthesis of ent-3

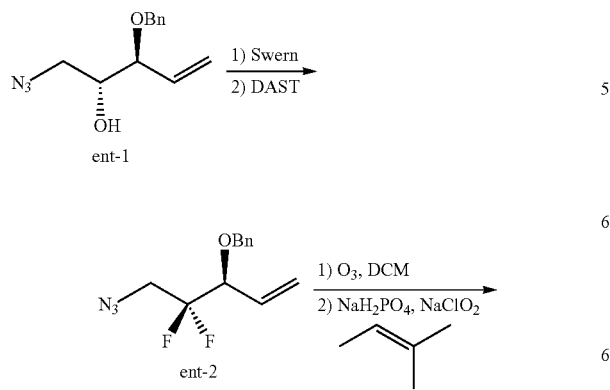

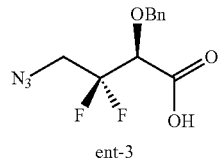

(2R,3S)-1-Azido-3-benzyloxy-4-penten-2-ol (ent-1, 500 mg, 2.14 mmol) was submitted to the same reaction conditions described above to yield (S)-5-azido-4,4-difluoro-3-benzyloxy-pent-1-ene (ent-2, 114 mg, 21% yield, $[\alpha]_D$=+27.9° (c 3.14, CHCl₃)). Ent-2 (75.5 mg, 0.32 mmol) was submitted to Procedure 13 to yield (S)-4-azido-2-benzyloxy-3,3-difluorobutanoic acid (ent-3, 34.8 mg, 43% yield, $[\alpha]_D$=+36.4° (c 0.80, CHCl₃).

Synthesis of (2S,3S)-4-azido-2,3-bis-benzyloxybutanoic acid (3)

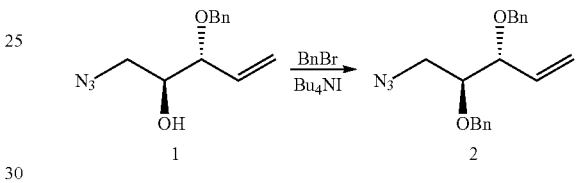

To a stirring solution of (2S,3R)-1-azido-3-benzyloxy-4-penten-2-ol (1) (250 μL, 1.07 mmol) in THF (50 mL) under argon was added tetrabutylammonium iodide (42 mg, 0.11 mmol) followed by benzyl bromide (155 μL, 1.27 mmol) and the reaction was cooled to 0° C. Sodium hydride (60% in mineral oil, 47 mg, 1.18 mmol) was added in small portions and the reaction was stirred overnight with warming to rt. The reaction was quenched with MeOH, filtered through Celite, and washed with Et₂O. The organic solvent was removed under vacuum to give an oily residue, which was purified by flash chromatography (silica gel, 2% Et₂O/hex) to yield (3R, 4S)-5-azido-3,4-bisbenzyloxy-pent-1-ene (2, 237 mg, 65% yield) as a clear non-volatile liquid: Rf=0.62 (1:4 EtOAc/hex); $[\alpha]_D$=−6.1° (c 1.50, CHCl₃); ¹H NMR (CDCl₃, 300 MHz) δ 7.35-7.24 (m, 10H), 5.81 (ddd, J=17.15, 10.58, 7.45 Hz, 1H), 5.37 (ddd, J=5.70, 1.65, 0.86 Hz, 1H), 5.33 (ddd, J=12.07, 1.44, 0.81 Hz, 1H), 4.63 (s, 2H), 4.61 (d, J=11.87 Hz, 1H), 4.35 (d, J=11.78 Hz, 1H), 3.90 (tdd, J=7.37, 5.65, 0.79, 0.79 Hz, 1H), 3.60 (ddd, J=6.39, 5.69, 3.64 Hz, 1H), 3.43 (dd, J=12.93, 6.42 Hz, 1H), 3.35 (dd, J=12.93, 3.60 Hz, 1H); ¹³C NMR (CDCl₃, 75 MHz) δ 138.25, 138.01, 135.43, 128.60 (4C), 128.29 (2C), 128.02, 127.99 (2C), 127.87, 119.97, 80.76, 80.23, 73.33, 70.79, 51.69; FTIR (NaCl): 2867, 2100, 1606, 1454, 1286, 1095, 1073.

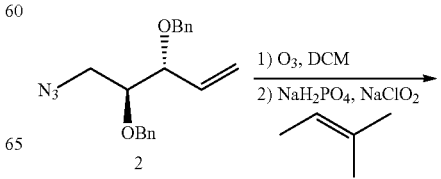

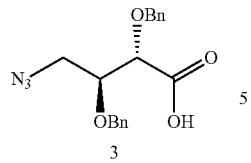

(3R,4S)-5-azido-3,4-bis-benzyloxy-pent-1-ene (2, 237 mg, 0.69 mmol) was submitted to Procedure 13 to yield (2S,3S)-4-azido-2,3-bis-benzyloxybutanoic acid (3, 187.7 mg, 75% yield): $[\alpha]_D=-15.1°$ (c 1.05, $CHCl_3$); HRMS (ESI negative mode) (M−H) calc. for $C_{18}H_{19}N_3O_4$ 340.1303, obs. 340.1296; $^1H$ NMR ($CDCl_3$, 300 MHz) δ 7.24 (s, 1H), 7.38-7.33 (m, 10H), 4.79 (d, J=11.61 Hz, 1H), 4.66 (s, 2H), 4.56 (d, J=11.61 Hz, 1H), 4.20 (d, J=4.24 Hz, 1H), 3.98 (td, J=6.56, 4.30, 4.30 Hz, 1H), 3.58 (dd, J=13.04, 6.62 Hz, 1H), 3.42 (dd, J=13.04, 4.31 Hz, 1H); $^{13}C$ NMR ($CDCl_3$, 75 MHz) δ 175.57, 137.92, 137.34, 129.44 (2C), 129.36 (2C), 129.15, 129.04 (2C), 128.98 (2C), 128.94, 79.71, 77.651, 74.04, 73.89, 51.65; FTIR (NaCl): 3000, 2918, 2103, 1722, 1455, 1284, 1110 $cm^{-1}$.

Synthesis of ent-3

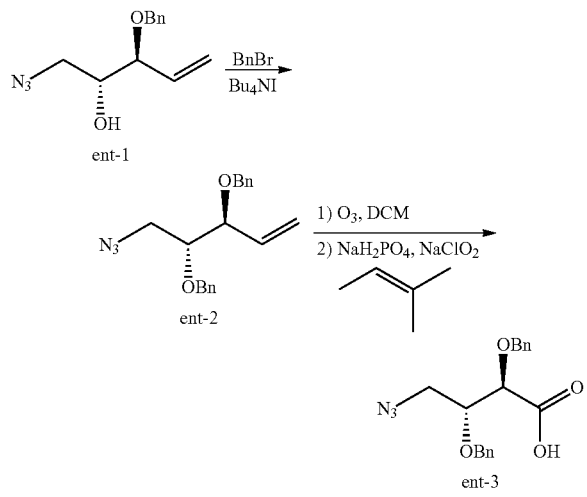

(2R,3S)-1-azido-3-benzyloxy-4-penten-2-ol (ent-1, 250 mg, 1.07 mmol) was submitted to the same reaction conditions as described above to yield (3S,4R)-5-azido-3,4-bis-benzyloxy-pent-1-ene (ent-2, 322 mg, 59% yield): $[\alpha]_D=+7.9°$ (c 1.50, $CHCl_3$). Ent-2 (178 mg, 0.55 mmol) was submitted to Procedure 13 to yield ent-3 (144 mg, 77% yield): $[\alpha]_D=+15.2°$ (c 0.81, $CHCl_3$).

Synthesis of Cyclopropyl Amino Acids

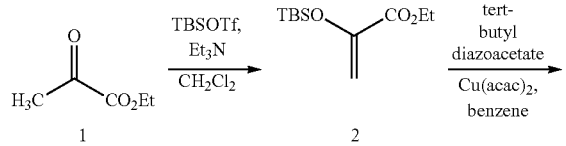

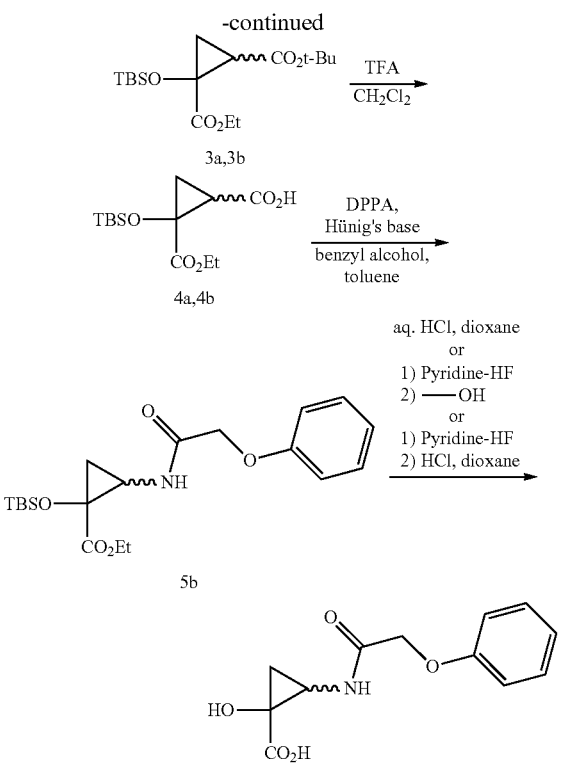

Ethyl-2-(tert-Butyldimethylsilyloxy)acrylate (2)

A solution of ester 1 (4.00 g, 34.4 mmol) and triethylamine (4.79 mL, 34.4 mmol) in anhydrous dichloromethane (170 mL) was cooled to 0° C. under nitrogen and tert-butyldimethylsilyltrifluoromethane sulfonate (8.31 mL, 36.2 mmol) was added dropwise. The resulting solution was stirred vigorously at reflux for 4 h. The solvent was then carefully evaporated, the residue was dissolved in $Et_2O$ (170 mL), and the organic phase was washed with water (3×50 mL). The organic phase was dried ($Na_2SO_4$), filtered, and concentrated. The residue was purified by silica gel chromatography eluting with 0-20% diethyl ether/hexanes to afford 2 (4.89 g, 62%) as a clear oil: $^1H$ NMR (500 MHz, $CDCl_3$) δ 5.50 (d, J=1.0 Hz, 1H), 4.85 (d, J=1.0 Hz, 1H), 4.21 (q, J=7.0 Hz, 2H), 1.31 (t, J=7.0 Hz, 3H), 0.95 (s, 9H), 0.16 (s, 6H).

2-tert-Butyl-1-Ethyl-1-(tert-butyldimethylsilyloxy) cyclopropane-1,2-dicarboxylate (3a and 3b)

A mixture of ethyl-2-(tert-butyldimethylsilyloxy)acrylate (2, 500 mg, 2.17 mmol) and $Cu(acac)_2$ (0.011 g, 0.043 mmol) was heated at 80° C. A solution of tert-butyl diazoacetate (463 mg, 3.25 mmol) in benzene (5 mL) was added to the reaction mixture over 2 h. After this time, the reaction mixture was cooled to room temperature and concentrated. The residue was purified by silica gel chromatography eluting with 0-10% diethyl ether/hexanes to afford both diastereomers 3a (0.119 g, 16%) and 3b (0.235 g, 31%) as clear oils. 3a: $^1H$ NMR (500 MHz, $CDCl_3$) δ 4.25-4.13 (m, 2H), 2.28 (dd, J=7.5, 2.0 Hz, 1H), 1.73 (dd, J=7.5, 2.0 Hz, 1H), 1.59 (dd, J=9.5, 4.0 Hz, 1H), 1.46 (s, 9H), 1.29 (t, J=7.5 Hz, 3H), 0.90 (s, 9H), 0.18 (s, 3H), 0.12 (s, 3H); ESI MS m/z 367 $[M+Na]^+$; 3b: $^1H$ NMR (500 MHz, $CDCl_3$) δ 4.23 (dq, J=11.0, 7.0 Hz, 1H), 4.13 (dq, J=11.0, 7.0 Hz, 1H), 2.11 (dd, J=10.0, 1.5 Hz, 1H), 1.85 (dd, J=5.5, 2.5 Hz, 1H), 1.43 (s, 9H), 1.54 (dd, J=10.0, 4.0 Hz, 1H), 1.28 (t, J=7.5 Hz, 3H), 0.86 (s, 9H), 0.19 (s, 3H), 0.18 (s, 3H); ESI MS m/z 367 [M+Na]+.

2-(tert-Butyldimethylsilyloxy)-2-(ethoxycarbonyl)cyclopropanecarboxylic Acid (4a and 4b)

A mixture of dicarboxylate 3a and 3b (0.385 g, 1.12 mmol, 1:2 ratio of 3a/3b), trifluoroacetic acid (0.43 mL), and dichloromethane (0.5 mL) was stirred overnight at room temperature. The solids were filtered, and the filtrate was concentrated. The residue was purified by silica gel chromatography eluting with 0-100% diethyl ether/hexanes to afford both diastereomers 4a (0.050 g, 15%) and 4b (0.078 g, 24%) as off-white solids. 4a: $^1$H NMR (500 MHz, CDCl$_3$) δ 4.25-4.17 (m, 2H), 2.38 (dd, J=7.5, 1.5 Hz, 1H), 1.81-1.76 (m, 2H), 1.30 (t, J=7.0 Hz, 3H), 0.90 (s, 9H), 0.21 (s, 3H), 0.13 (s, 3H); ESI MS m/z 289 [M+H]+; 4b: $^1$H NMR (500 MHz, CDCl$_3$) δ 4.22 (q, J=7.0 Hz, 1H), 2.21 (dd, J=10.0, 1.5 Hz, 1H), 1.93 (dd, J=8.0, 2.0 Hz, 1H), 1.52 (dd, J=6.0, 3.5 Hz, 1H), 1.28 (t, J=7.0 Hz, 3H), 0.87 (s, 9H), 0.19 (s, 3H), 0.17 (s, 3H); ESI MS m/z 287 [M−H]−.

Ethyl-2-(Benzyloxycarbonylamino)-1-(tert-butyldimethylsilyloxy)cyclopropanecarboxylate (5b)

A mixture of 2-(tert-butyldimethylsilyloxy)-2-(ethoxycarbonyl)cyclopropanecarboxylic acid (4b, 0.335 g, 1.16 mmol) in toluene (5 mL) under nitrogen was treated with Hünig's base (0.260 mL, 1.51 mmol) and the mixture was cooled to 0° C. After this time, DPPA (0.324 mL, 1.51 mmol) was added and the mixture was heated at 90° C. for 30 min, followed by the addition of benzyl alcohol (0.155 mL, 1.51 mmol). After 15 h, the mixture was cooled, diluted with ethyl acetate (75 mL), and washed sequentially with 10% citric acid (2×50 mL), water (50 mL), and saturated NaHCO$_3$ (50 mL). The organic phase was dried (MgSO$_4$), filtered, and concentrated. The residue was purified by silica gel chromatography eluting with 10% EtOAc/hexanes to 100% EtOAc to afford the title compound as a clear oil (0.146 g, 30%): $^1$H NMR (300 MHz, CDCl$_3$) δ 7.34-7.30 (m, 5H), 5.40-5.38 (m, 1H), 5.21-5.00 (m, 2H), 4.29-4.18 (m, 2H), 4.16-4.09 (m, 1H), 1.50-1.47 (m, 2H), 1.30 (t, J=7.2 Hz, 3H), 0.88 (s, 9H), 0.26-0.07 (m, 6H); Multimode (APCI+ESI) MS m/z 295 [M+H]+.

REPRESENTATIVE COMPOUNDS

Example 1

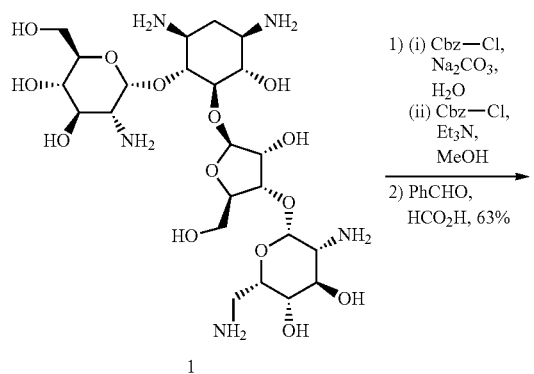

Sodium carbonate (55.0 g, 0.523 mol) and Cbz-Cl (20.00 mL, 0.139 mol) were added to paromomycin sulfate (30.00 g, 0.0271 mol) in water (500 mL). After 35 hours under vigorous stirring, the water was decanted and the white precipitate was washed with water twice. A solution of triethylamine (97.00 mL, 0.697 mol) in methanol (600 mL) was added, followed by Cbz-Cl (25.00 mL, 0.174 mol). After 24 hours, dimethylamine (100 mL of a 40% aqueous solution) was added to quench the remaining Cbz-Cl. The solvents were evaporated and the oil was washed with 3% methanol in ether twice and water. The resulting sticky solid was co-distilled with pyridine (200 mL) three times and at of the volume of the third co-distillation, toluene (200 mL) was added and the solvents were evaporated to dryness. Another co-distillation with toluene (300 mL) was done before heating the flask at 60° C. under 10 mm Hg vacuum for 12 hours. Freshly distilled benzaldehyde (400 mL) was added to the resulting white solid and sonication was used to form a solution. To the stirred mixture was added 4 angstrom molecular sieves (15 g) and formic acid (20.00 mL, 0.530 mol). After stirring for 12 hours at room temperature, the mixture was added dropwise to a stirred ice-cold solution of saturated aqueous Na$_2$CO$_3$, extracted with ethyl acetate (3×), and the organic layer was washed with water, brine and dried over Na$_2$SO$_4$. The solvent was evaporated to dryness and excess benzaldehyde was removed under vacuum to afford a crude solid, which was purified by flash column chromatography over silica gel (3% MeOH/CH$_2$Cl$_2$) to obtain pure 2 (23.89 g, 63%). The spectroscopic analysis of the resulting material was consistent with data reported in the literature for the identical material (Hanessian S., Takamoto T., Masse R., Patil G.; Aminoglycoside antibiotics: Chemical conversion of neomycin B, paromomycin, and lividomycin B into bioactive pseudosaccharides; *Can. J. Chem.*, 1978, 56, 1482).

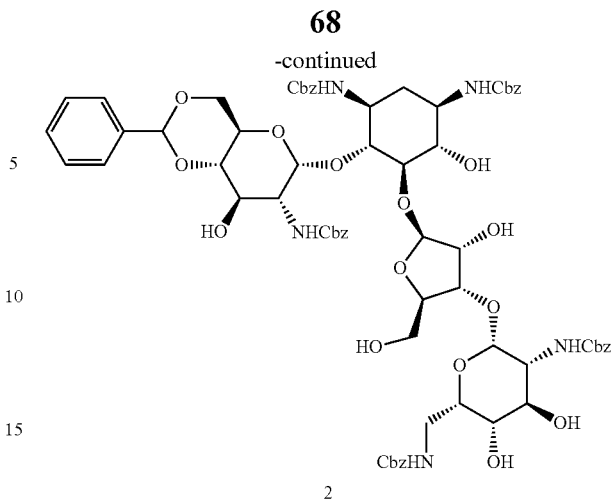

2 ⟶

-continued

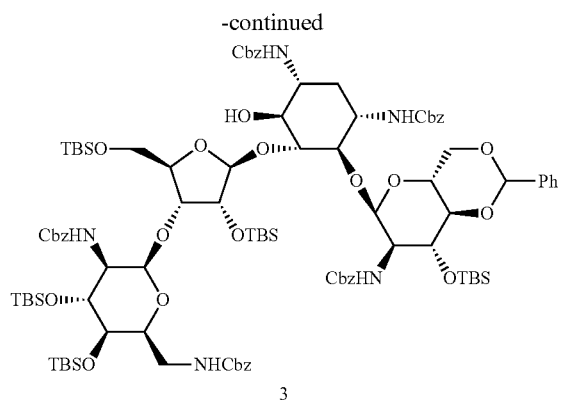

3

To a stirred solution of 2 (1.35 g, 0.98 mmol) in dry dichloromethane (20 mL) was added 2,4,6-collidine (1.07 g, 8.82 mmol) and TBSOTf (1.811 g, 6.86 mmol) at 0° C. The reaction mixture was slowly brought to room temperature and stirred for 12 hours. A few drops of water was added to quench the excess TBSOTf, followed by extraction with dichloromethane. The organic layer was washed with brine and dried over anhydrous $Na_2SO_4$, followed by concentration of the solvent to give the corresponding crude product. The crude product was purified by flash column chromatography to give 3 (1.048 g, 55%). $[\alpha]_D=+16°$ (c 0.6, $CHCl_3$). ESI/MS calcd for $C_{100}H_{149}N_5O_{24}Si_5$ (M+H$^+$) 1944.94, found 1946.

3 ⟶

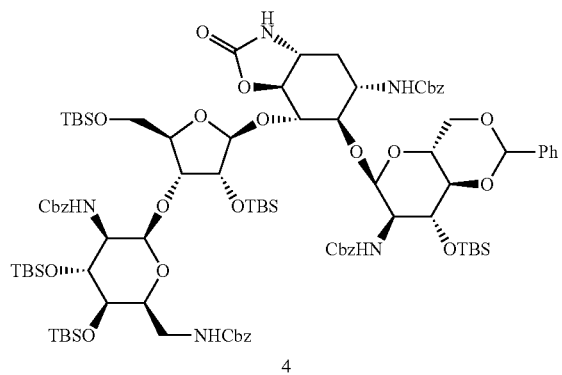

4

To a stirred solution of 3 (330 mg, 0.17 mmol) in dry DMF (6 mL) was added 60% NaH in mineral oil (8 mg) at 0° C. with stirring continued for an additional 6 hours at 0° C. A few drops of saturated ammonium chloride solution were added, followed by extraction with ethyl acetate. The organic layer was washed with brine and dried over anhydrous $Na_2SO_4$, followed by concentration of the solvent yielding the corresponding crude product. The crude product was purified by flash column chromatography to yield 4 (180 mg, 58%). $[\alpha]_D=+18°$ (c 0.5, $CHCl_3$). ESI/MS calcd for $C_{93}H_{141}N_5O_{23}Si_5$ (M+H$^+$) 1836.89, found 1837.6.

4 ⟶

-continued

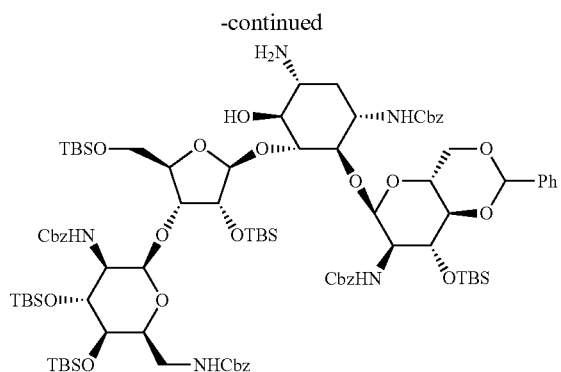

5

To a stirred solution of 4 (190 mg, 0.1 mmol) in DMF (7 mL) was added 0.7 mL of aqueous LiOH (9 mg, 0.21 mmol) with stirring continued for an additional 3 hours at room temperature. A few drops of saturated ammonium chloride solution was added, followed by extraction with ethyl acetate. The organic layer was washed with brine and dried over anhydrous $Na_2SO_4$, followed by concentration of the solvent yielding the corresponding crude product. The crude product was purified by flash column chromatography to yield 5 (100 mg, 53%). $[\alpha]_D=+13°$ (c 0.3, $CHCl_3$). ESI/MS calcd for $C_{92}H_{143}N_5O_{22}Si_5$ (M+H$^+$) 1810.91, found 1811.3.

5 ⟶

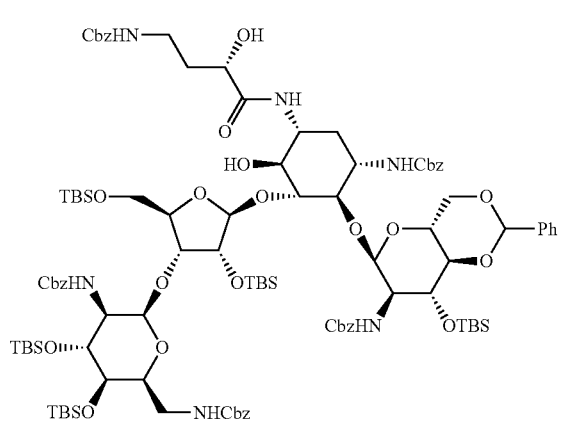

6

To a stirred solution of (S-4-(benzyloxycarbonylamino)-2-hydroxybutanoic acid (27 mg, 0.11 mmol) and N-hydroxysuccinimide (12 mg, 0.11 mmol) in dry THF (2 mL) was added DCC (22 mg, 0.11 mmol) with stirring continued for an additional 1 hour at room temperature. To this reaction mixture the free amine 5 (95 mg, 0.053 mmol) in dry THF (2 mL) and triethyl amine (15 µL, 0.11 mmol) was added with stirring for 12 hours at room temperature. Evaporation of the solvent followed by purification by flash column chromatography yielded 6 (80 mg, 74%). $[\alpha]_D=+19°$ (c 0.4, $CHCl_3$).

6 ⟶

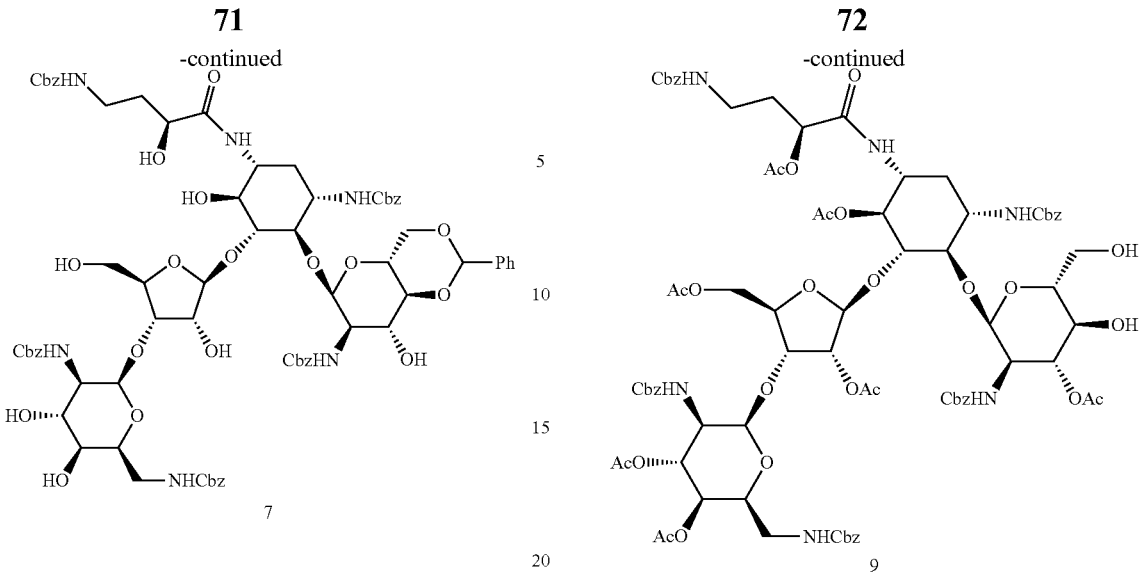

6 (90 mg, 0.044 mmol) was dissolved in dry pyridine (2 mL), HF.Py (2 mL) was added at 0° C., the reaction was slowly brought to room temperature and stirred for 2 days. Water was added and the reaction mixture was extracted with ethyl acetate followed by washing with brine. The organic layer was dried over $Na_2SO_4$ and evaporated to give the crude product. The crude product was purified by column chromatography to yield 7 (50 mg, 77%). $[\alpha]_D=+20°$ (c 0.6, $CHCl_3$). ESI/MS calcd for $C_{74}H_{86}N_6O_{26}$ $(M+H^+)$ 1475.56, found 1475.7.

7 ⟶

8 (300 mg, 0.17 mmol) was stirred in 20 mL of acetic acid/water mixture (4:1) at room temperature for 4 days. Water was added and the precipitated product was filtered. The aqueous layer was extracted with ethyl acetate, washed with water, brine and the organic layer was dried over anhydrous $Na_2SO_4$. The organic layer was combined with the precipitated product and evaporated to yield the crude material, which yielded 9 (280 mg, 98%) after column chromatography. $[\alpha]_D=+10.7°$ (c 0.3, $CHCl_3$). HRMS calcd for $C_{81}H_{97}N_6O_{33}$ $(M+H^+)$ 1681.60911, found 1681.60830.

9 ⟶

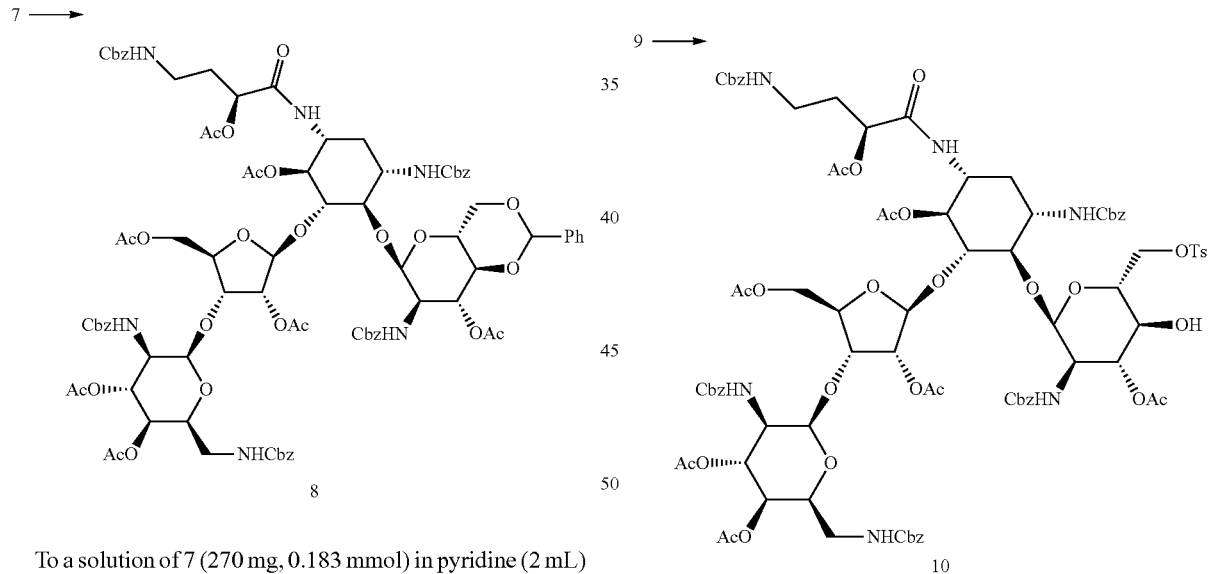

To a solution of 7 (270 mg, 0.183 mmol) in pyridine (2 mL) was added acetic anhydride (1 mL) with stirring maintained for 24 hours at room temperature. Water (10 mL) was added and the precipitated product was filtered. The aqueous layer was extracted with ethyl acetate, washed with saturated $CuSO_4$, brine and the organic layer was dried over anhydrous $Na_2SO_4$. The organic layer was combined with the precipitated product and evaporated to provide the crude material, which yielded 8 (300 mg, 93%) after column chromatography. $[\alpha]_D=+7.5°$ (c 0.2, $CHCl_3$). ESI/MS calcd for $C_{88}H_{100}N_6O_{33}$ $(M+H^+)$ 1768.63, found 1769.8.

8 ⟶

To a solution of 9 (290 mg, 0.17 mmol) in pyridine (2 mL) was added TsCl (36 mg, 0.19 mmol) and DMAP (5 mg, 0.041 mmol) with stirring maintained for 12 hours at room temperature. An additional 1.1 equivalent of TsCl (36 mg, 0.19 mmol) was added and the reaction was stirred for additional 8 hours at room temperature. Water was added and the precipitated product was filtered. The aqueous layer was extracted with ethyl acetate, washed with water, brine and the organic layer was dried over anhydrous $Na_2SO_4$. The organic layer was combined with the precipitated product and evaporated to yield the crude material. 10 (300 mg, 96%) was obtained after column chromatography. $[\alpha]_D=+14.8°$ (c 0.25, $CHCl_3$). HRMS calcd for $C_{88}H_{102}N_6O_{35}S$ $(M+H^+)$ 1835.61796, found 1835.61976.

10 →

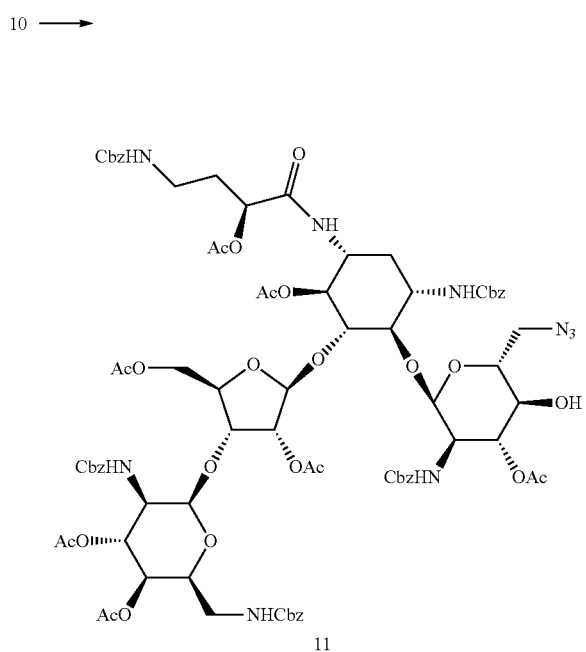

11

To a solution of 10 (320 mg, 0.175 mmol) in dry DMF (3 mL) was added NaN$_3$ (113 mg, 1.74 mmol) with stirring maintained for 24 hours at 70° C. Water was added and the resulting mixture was extracted with ethyl acetate followed by washing with water and then brine. The organic layer was dried over anhydrous Na$_2$SO$_4$ and evaporated under reduced pressure. 11 (252 mg, 84%) was obtained following column chromatography. $[\alpha]_D$=+11.3° (c 0.3, CHCl$_3$). ESUMS calcd for $C_{81}H_{95}N_9O_{32}$ (M+H$^+$) 1705.61, found 1707.0.

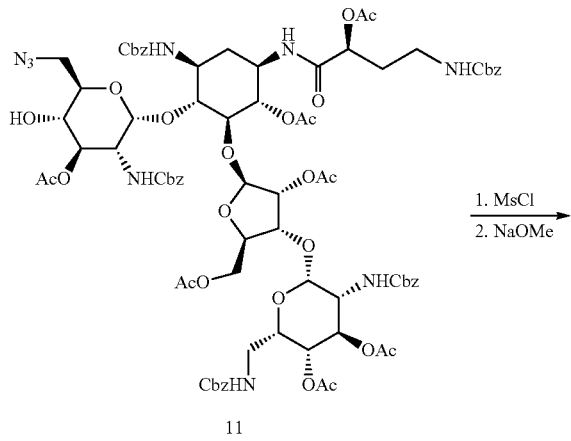

11

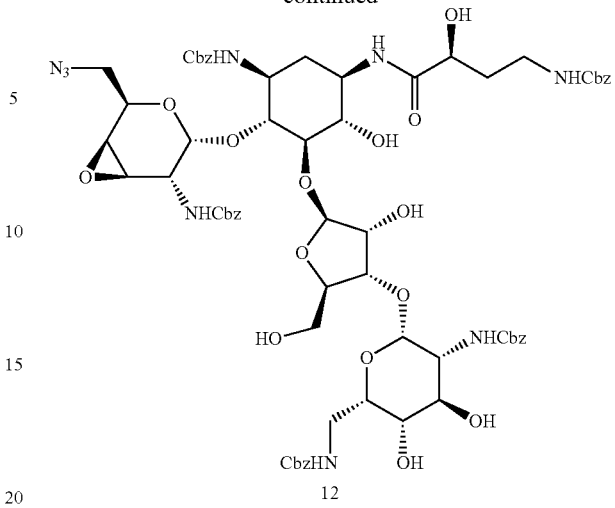

12

To a stirred solution of 11 (115 mg, 0.067 mmol) in pyridine (2 mL) was added 10 µL of MSCl (0.13 mmol) at 0° C. and the reaction mixture was slowly brought to room temperature and stirred for 3 hours. A few drops of water were added to quench the reaction and the reaction was extracted with ethyl acetate. The organic layer was washed with saturated CuSO$_4$, water, brine and dried over anhydrous Na$_2$SO$_4$, followed by concentration of the solvent yielding the corresponding crude product. The crude product was dissolved in pre-prepared NaOMe in methanol (pH=10-11) and stirred at room temperature for 12 hours. Dry ice was added to quench the reaction and extracted with ethyl acetate. The organic layer was washed with water, brine and dried over anhydrous Na$_2$SO$_4$, followed by concentration of the solvent yielding the corresponding crude product 12. ESUMS calcd for $C_{67}H_{79}N_9O_{24}$ (M+Na$^+$) 1416.5, found 1416.3.

$$12 \xrightarrow[\text{DIPEA, THF/H}_2\text{O, rt, 1 hr}]{\text{P(CH}_2\text{CH}_2\text{CO}_2\text{H)}_3 \cdot \text{HCl}}$$
100%

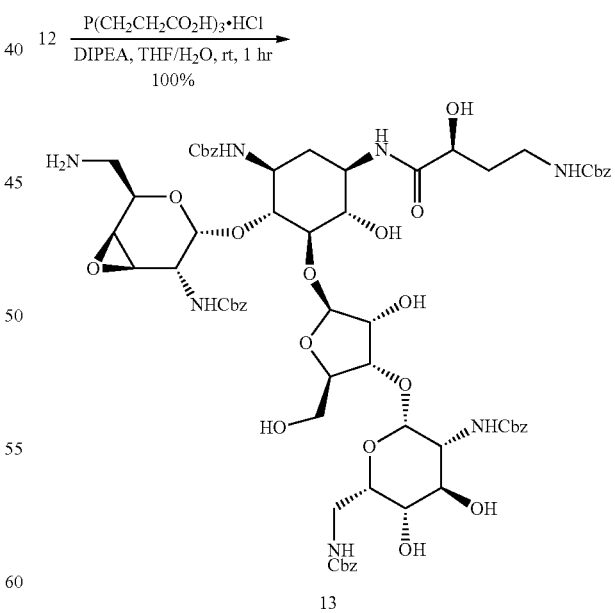

13

To a stirred solution of crude 12 (33.6 g, 23 mmol) in tetrahydrofuran (335 mL) were added water (33.5 mL), diisopropylethylamine (42 mL, 245 mmol) and tris(2-carboxyethyl)phosphine hydrochloride (20.8 g, 72.7 mmol). The reaction was warmed slightly and was placed in a 20° C. water bath. After 1 hr the reaction was partitioned between ethyl acetate (800 mL) and saturated sodium bicarbonate (400 mL). The aqueous layer was back extracted with ethyl acetate (200 mL) and the combined organic layers were washed with saturated sodium bicarbonate (400 mL), brine (350 mL), dried with magnesium sulfate, filtered and concentrated in vacuo to yield crude 13 (33.2 g). MS m/z calcd for $C_{67}H_{81}N_7O_{24}$ 1368.5 (M+H$^+$), found 1368.3.

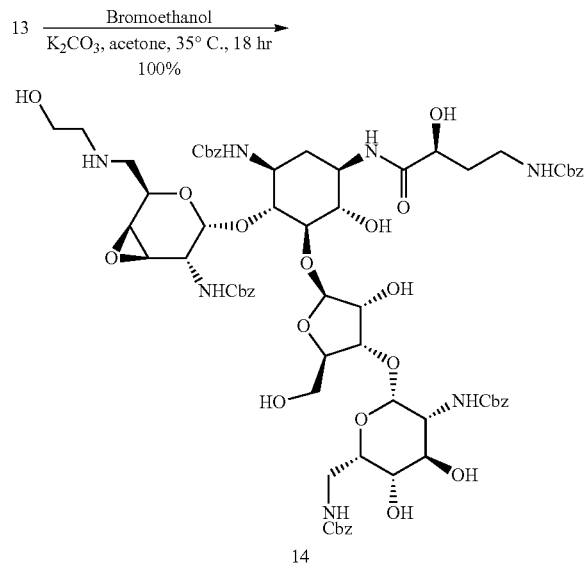

To a stirred solution of crude 13 (29.8 g, 22 mmol) in dry acetone were added potassium carbonate (12 g, 88 mmol) and bromoethanol (5.1 mL, 73 mmol). The reaction was heated in a 35° C. oil bath for 18 hr, then saturated ammonium chloride (1.0 L) was added and the product was extracted with ethyl acetate (600 mL, then 300 mL). The combined organic layers were washed with saturated sodium bicarbonate (500 mL, then 250 mL) and brine (350 mL), then dried with magnesium sulfate, filtered and concentrated in vacuo to yield crude 14 (32 g). MS m/z calcd for $C_{69}H_{85}N_7O_{25}$ 1412.6 (M+H$^+$), found 1412.3.

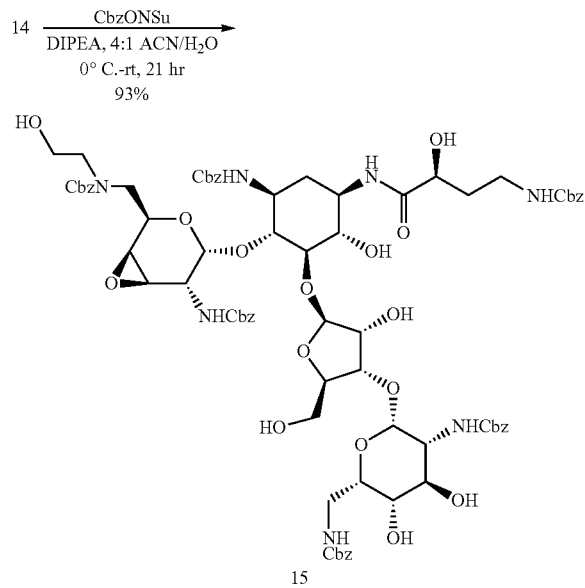 [SMILES: "Bromoethanol" ; O=C(NCC[C@H](O)C(=O)N[C@@H]1C[C@H](NC(=O)OCc2ccccc2)[C@@H](O[C@H]2O[C@H](CNCCO)[C@@H]3O[C@@H]3[C@H]2NC(=O)OCc2ccccc2)[C@H](O[C@@H]2O[C@H](CO)[C@@H](O[C@H]3O[C@@H](CNC(=O)OCc4ccccc4)[C@@H](O)[C@H](O)[C@H]3NC(=O)OCc3ccccc3)[C@H]2O)[C@H]1O)OCc1ccccc1]

To a stirred solution of crude 14 (33 g, 23 mmol) in acetonitrile (320 mL) and water (80 mL) was added diisopropylethylamine (8.1 mL, 47 mmol). The reaction was stirred in an ice bath for ten minutes, then N-(benzyloxycarbonyloxy)-succinimide (5.9 g, 24 mmol) was added. After stirring in the ice bath for 5 minutes, the reaction was stirred at room temperature for 21 hr. The reaction was then placed back in an ice bath for 10 min and 1 M citric acid was added (600 mL) followed by brine (240 mL). The product was extracted with EtOAc (800 mL, then 200 mL). The combined organic layers were washed with brine (400 mL), saturated sodium bicarbonate (600 mL) and brine (350 mL), then dried with magnesium sulfate, filtered and concentrated in vacuo to yield crude 15 (33 g). MS m/z calcd for $C_{77}H_{91}N_7O_{27}$ 1568.6 (M+Na$^+$), found 1568.5.

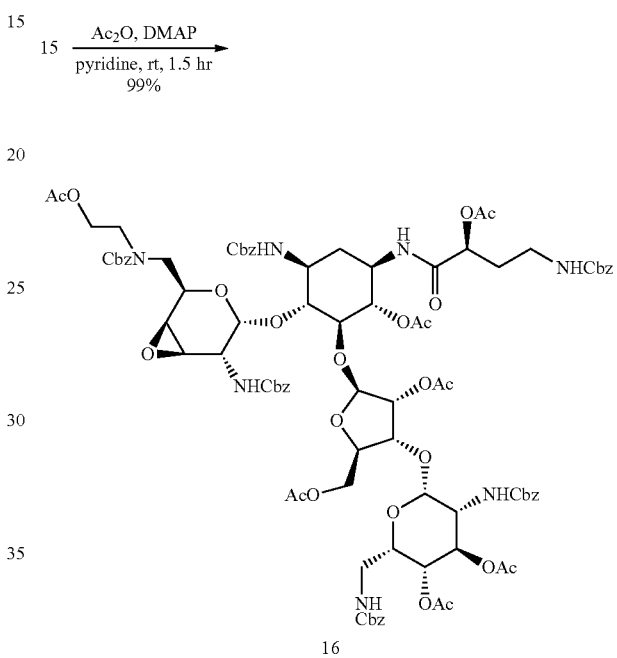

To a stirred solution of crude 15 (33 g, 22 mmol) in pyridine (330 mL) and acetic anhydride (330 mL) was added 4-dimethylaminopyridine (1.5 g, 13 mmol, 0.59 eq). After 1.5 hr the reaction was transferred to a 2 L 2-neck round bottom flask equipped with a dropping funnel and a thermometer to measure the internal temperature. The reaction was cooled to 5° C. in an ice bath and methanol (200 mL) was added dropwise over 2 hours, while the internal temperature was kept at 8-12° C. The reaction was diluted with water (800 mL) and brine (100 mL) and the product was extracted with EtOAc (1000 mL, then 200 mL). The combined organic layers were washed with 1 M citric acid (3×800 mL), brine (400 mL), saturated sodium bicarbonate (800 mL) and brine (400 mL), then dried with magnesium sulfate, filtered and concentrated in vacuo to yield crude 16 (39 g). MS m/z calcd for $C_{91}H_{105}N_7O_{34}$ 1862.7 (M+Na$^+$), found: 1862.6.

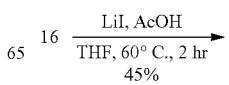

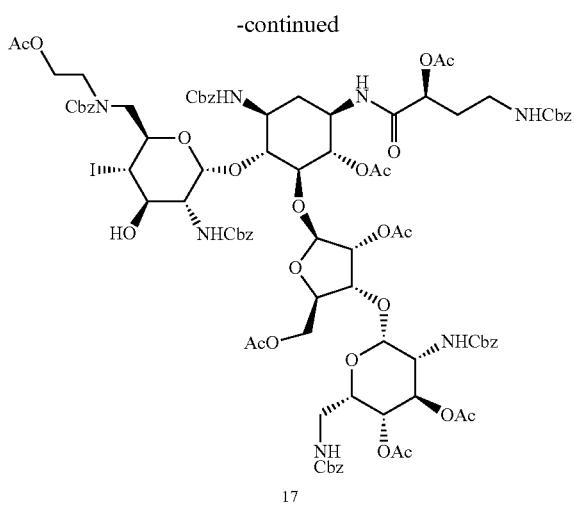

17

To tetrahydrofuran (200 mL), cooled in an ice bath, was added lithium iodide (17 g, 128 mmol, 6 eq) followed by acetic acid (3.7 mL, 64 mmol, 3.0 eq). This solution was added to a stirred solution of crude 16 (39 g, 21 mmol) in tetrahydrofuran (200 mL). The reaction was placed in a 60° C. oil bath for 2 hr, then allowed to cool to room temperature. Water (800 mL) and brine (200 mL) were added and the product was extracted with EtOAc (800 mL). The organic layer was washed with brine (400 mL), aqueous sodium sulfite (300 mL), saturated sodium bicarbonate (600 mL) and brine (400 mL), then dried with magnesium sulfate, filtered and concentrated in vacuo to yield of crude, which was purified on a 6-inch reverse phase HPLC to yield 17 (19 g). MS m/z calcd for $C_{91}H_{106}IN_7O_{34}$ 1990.6 (M+Na$^+$), found 1990.4.

17 $\xrightarrow{\text{1) MsCl, pyr, 0° C.-rt, 24 hr}}_{\text{2) LiI, 70° C., 75 min}}$
100%

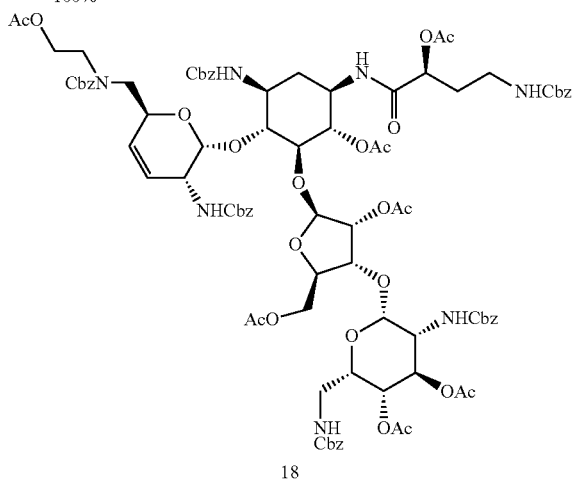

18

In a 2-neck 2-L round bottom flask equipped with a thermometer, a solution of 17 (19 g, 9.6 mmol) in pyridine (360 mL) was cooled to 5° C. in an ice bath. Methanesulfonyl chloride (5.4 mL, 69 mmol, 7.2 eq) was added slowly (1 min), then the reaction was removed from the ice bath and stirred at room temperature for 24 hr. The reaction was placed in an ice bath and cooled to 3° C., then methanol (36 mL) was added dropwise over 5 min. The reaction was removed from the ice bath, lithium iodide (8.6 g, 64 mmol, 6.7 eq) was added, and the reaction was placed in a 70° C. oil bath for 75 min. The reaction was allowed to cool and was placed in a water bath. Aqueous sodium sulfite (200 mL) was added and the reaction warmed from 25° C. to 30° C. Ice was added to the bath to cool the reaction back down to room temperature. Water (200 mL) and brine (100 mL) were added and the product was extracted with EtOAc (400 mL, then 200 mL). The combined organic layers were washed with 1 M citric acid (5×400 mL), brine (200 mL), saturated sodium bicarbonate (300 mL) and brine (200 mL), then dried with magnesium sulfate, filtered and concentrated in vacuo to yield crude 18 (18 g). MS m/z calcd for $C_{91}H_{105}N_7O_{33}$ 1846.7, found 1846.5.

18 $\xrightarrow[\text{rt, 24 hr}]{\text{MeNH}_2\text{, MeOH}}$
78%

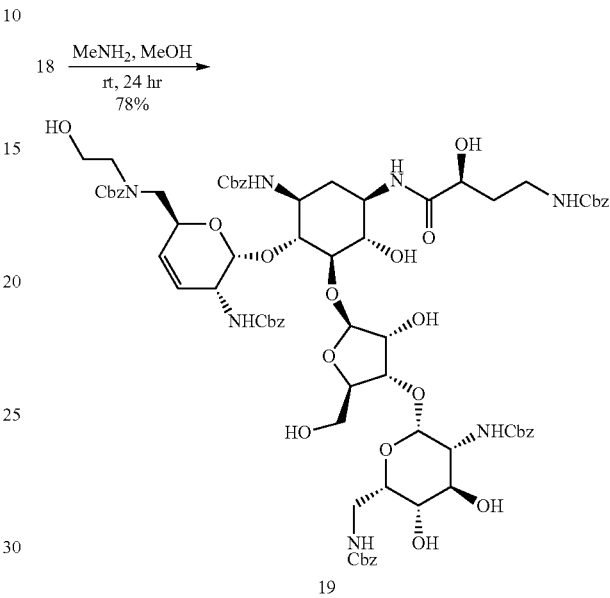

19

To a stirred solution of crude 18 (18 g, 9.6 mmol) in methanol (475 mL) was added methylamine (40% in water, 125 mL). The reaction was warmed slightly and was placed in an ice bath briefly (less than 5 min), then stirred at room temperature for 24 hr. The solution was concentrated to remove the methanol and most of the water. The crude reaction mixture was then purified on a 6-inch reverse phase HPLC column to yield 19 (11.5 g, 7.51 mmol, 78%). MS m/z calcd for $C_{77}H_{91}N_7O_{26}$ 1552.6 (M+Na$^+$), found 1552.6.

19 $\xrightarrow[\text{AcOH/H}_2\text{O, rt, 4 hr}]{\text{H}_2\text{, Pd/C}}$
74%

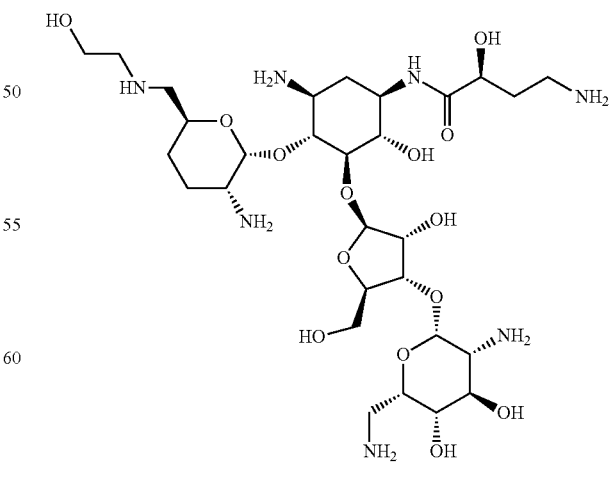

20

To a stirred solution of 19 (7.3 g, 4.8 mmol) in acetic acid (20 mL) and water (10 mL) was added 5% Pd/C (wet, 2.8 g). The reaction was placed under a hydrogen atmosphere for one hour, then more Pd/C (1.6 g) was added. After an additional hour, water (10 mL) and Pd/C (1.0 g) were added, followed by more water (10 mL) and Pd/C (1.0 g) one hour later. After stirring one additional hour under hydrogen, the reaction was filtered through a 0.45 μm PTFE filter and rinsed with water. The solution was diluted with water (500 mL), then lyophilized. The crude material was purified by preparative HPLC using a basic mobile phase (10 mM NH$_4$OH in water/ACN) to yield 20: MS Calc for $C_{29}H_{57}N_7O_{14}$: 728.4 (M+H$^+$), found 728.3; CLND method.

Example 2

Other Representative Compounds

The following representative compounds may be prepared according to the foregoing procedures.

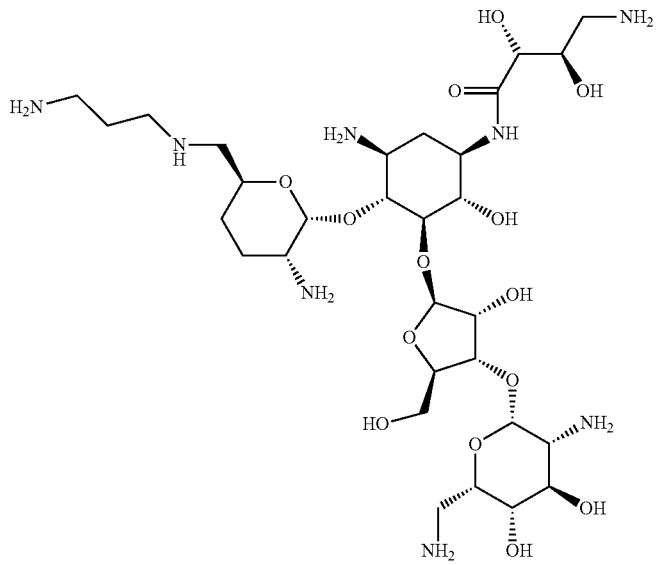

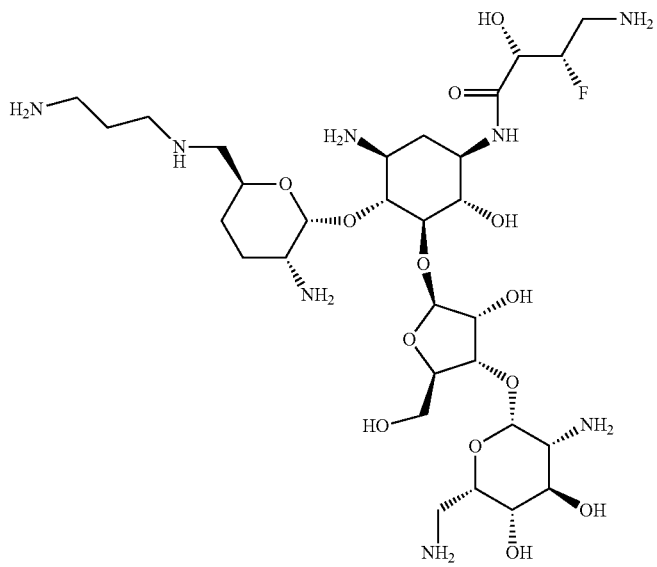

-continued
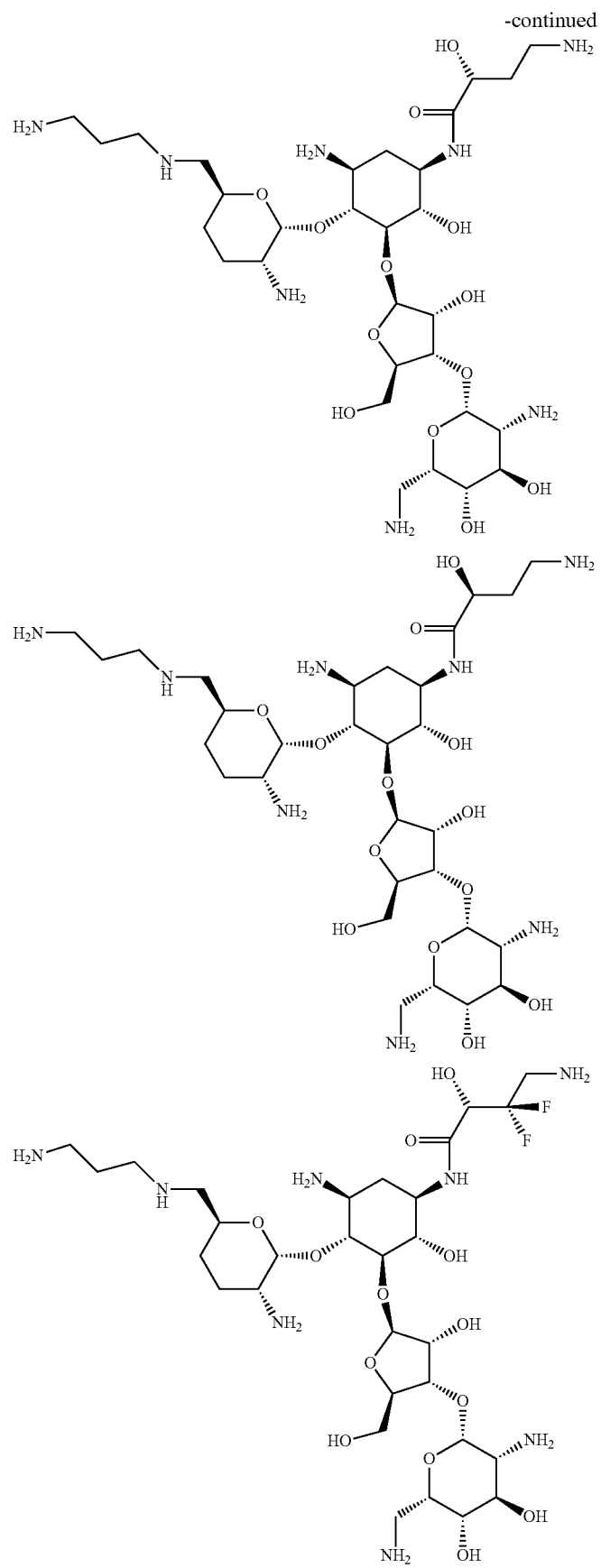

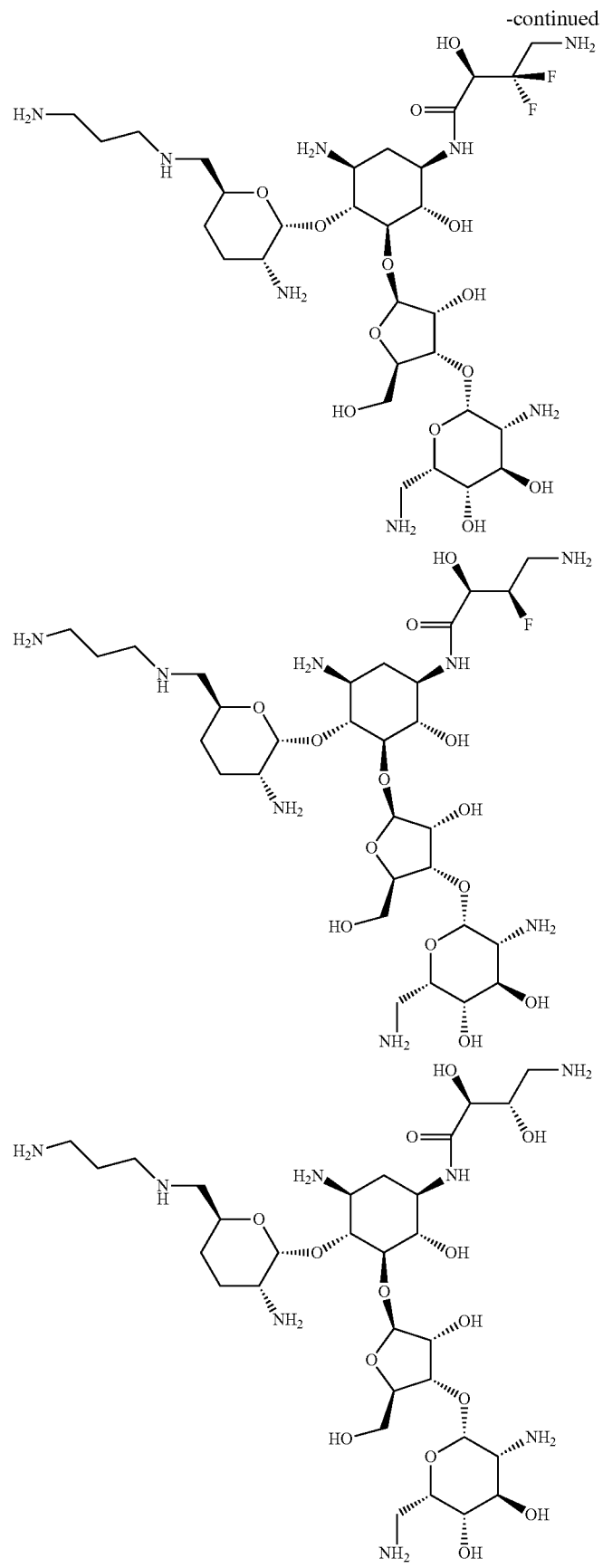

-continued
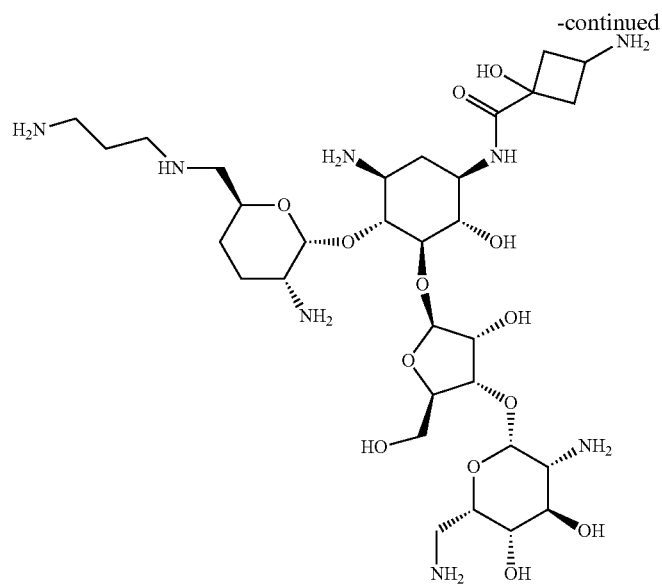
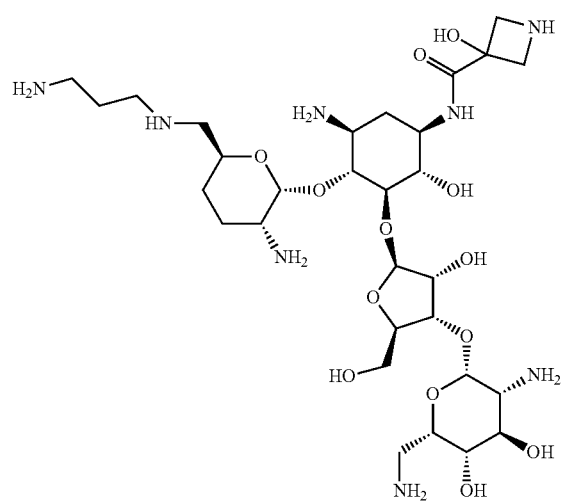
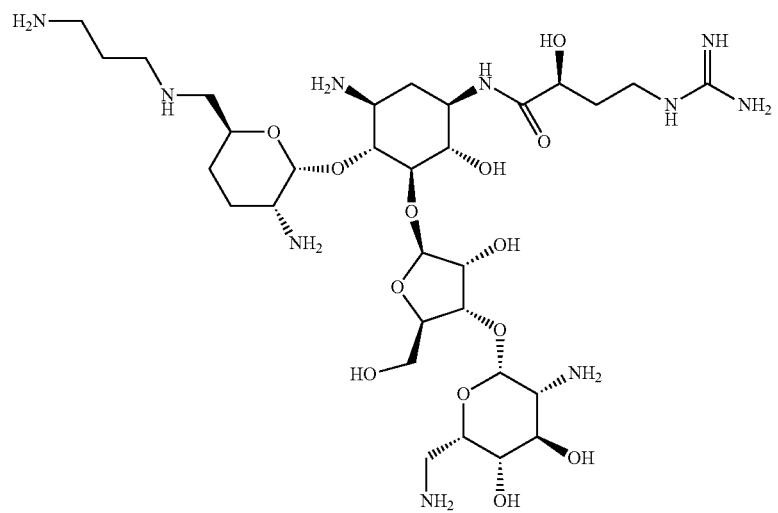

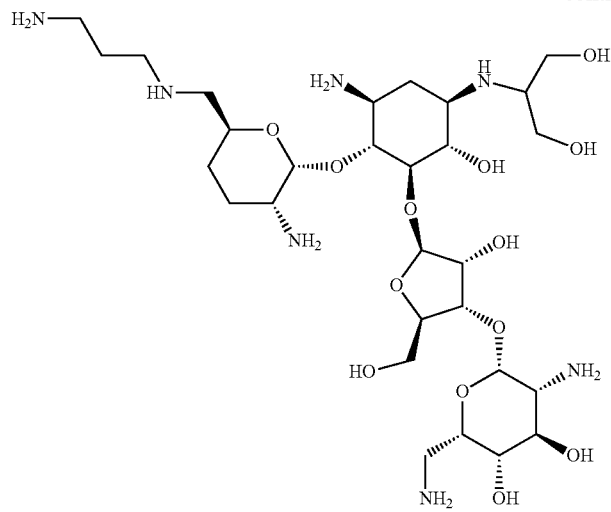
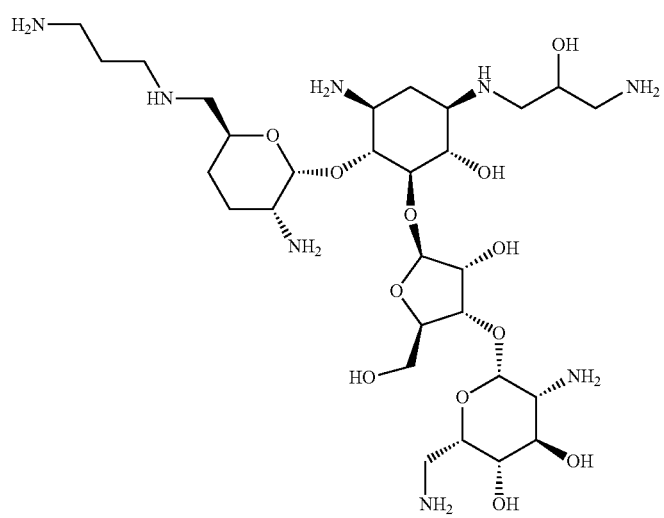
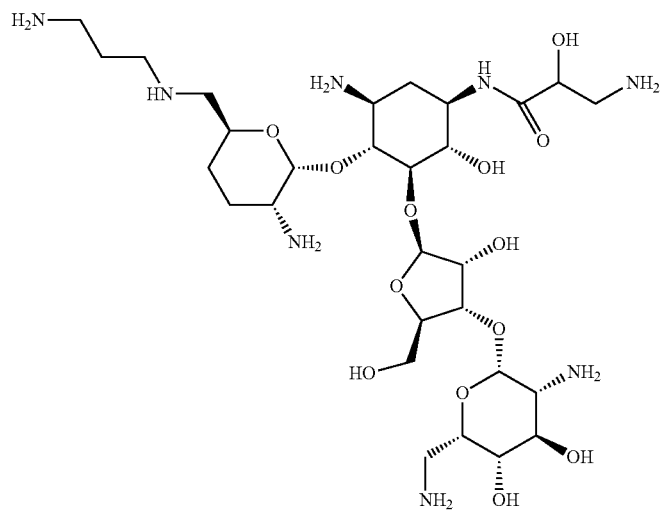

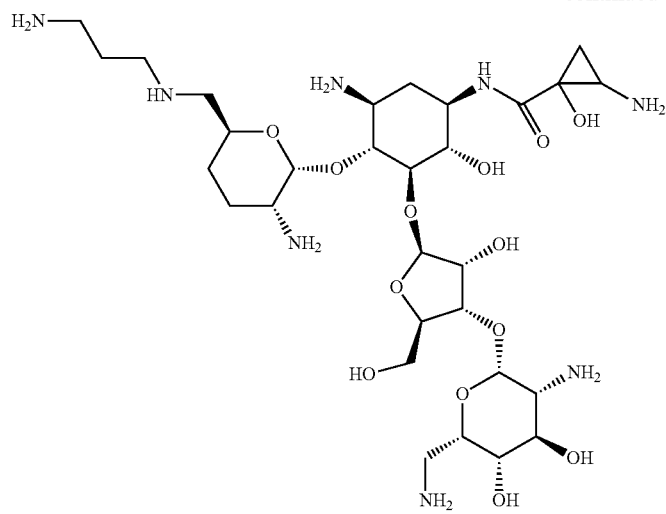
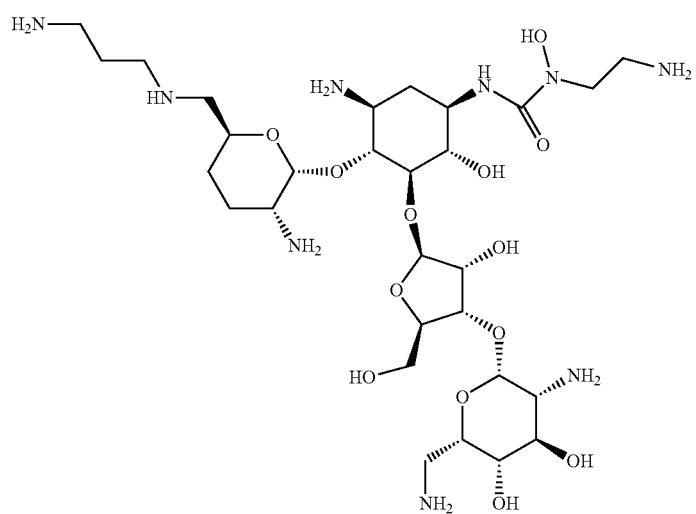
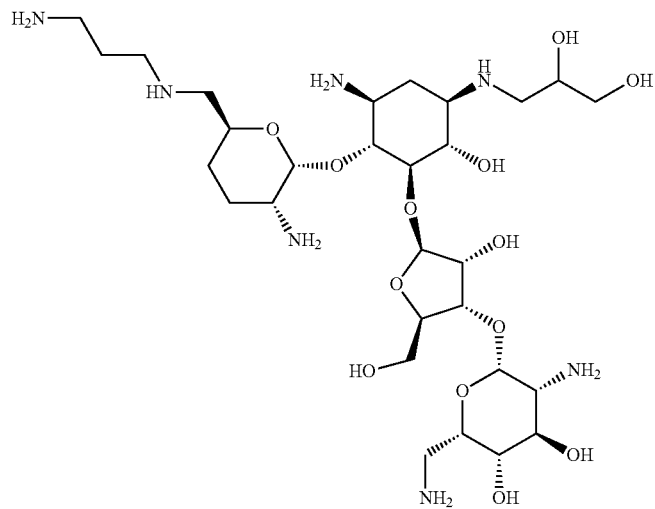

91
-continued
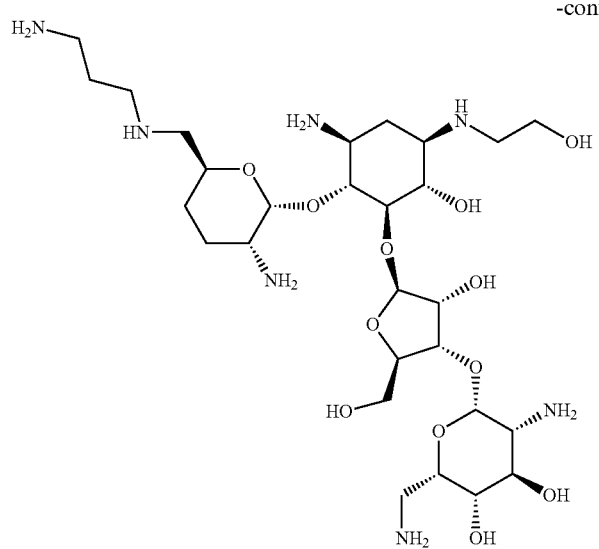
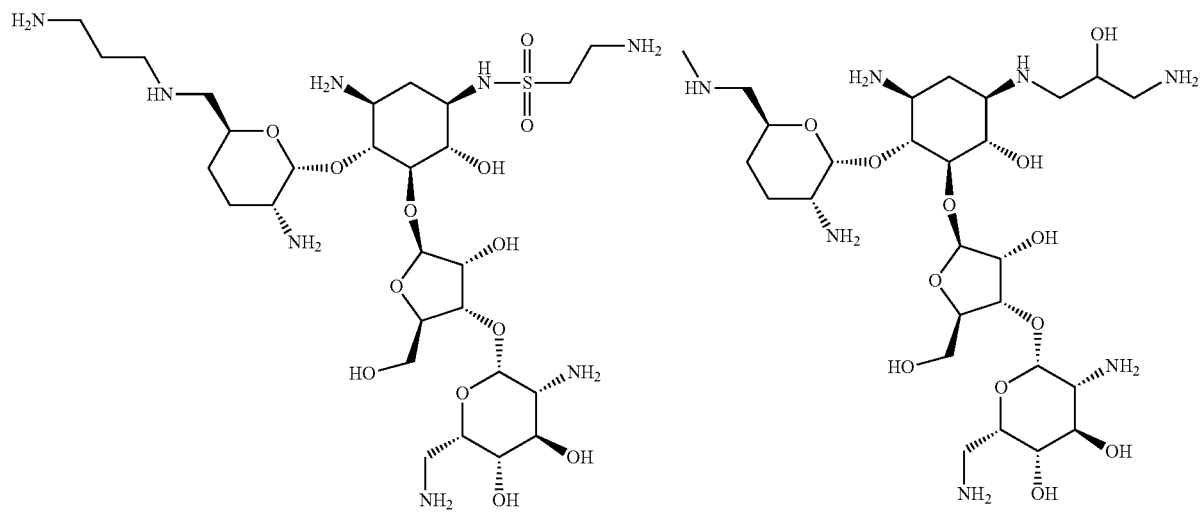
92
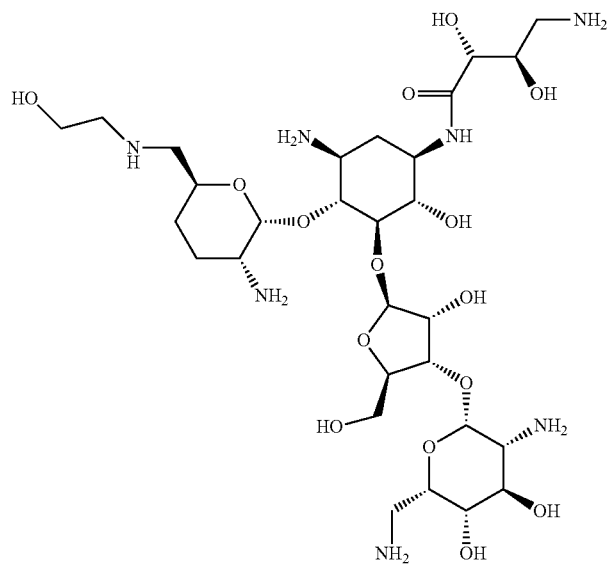

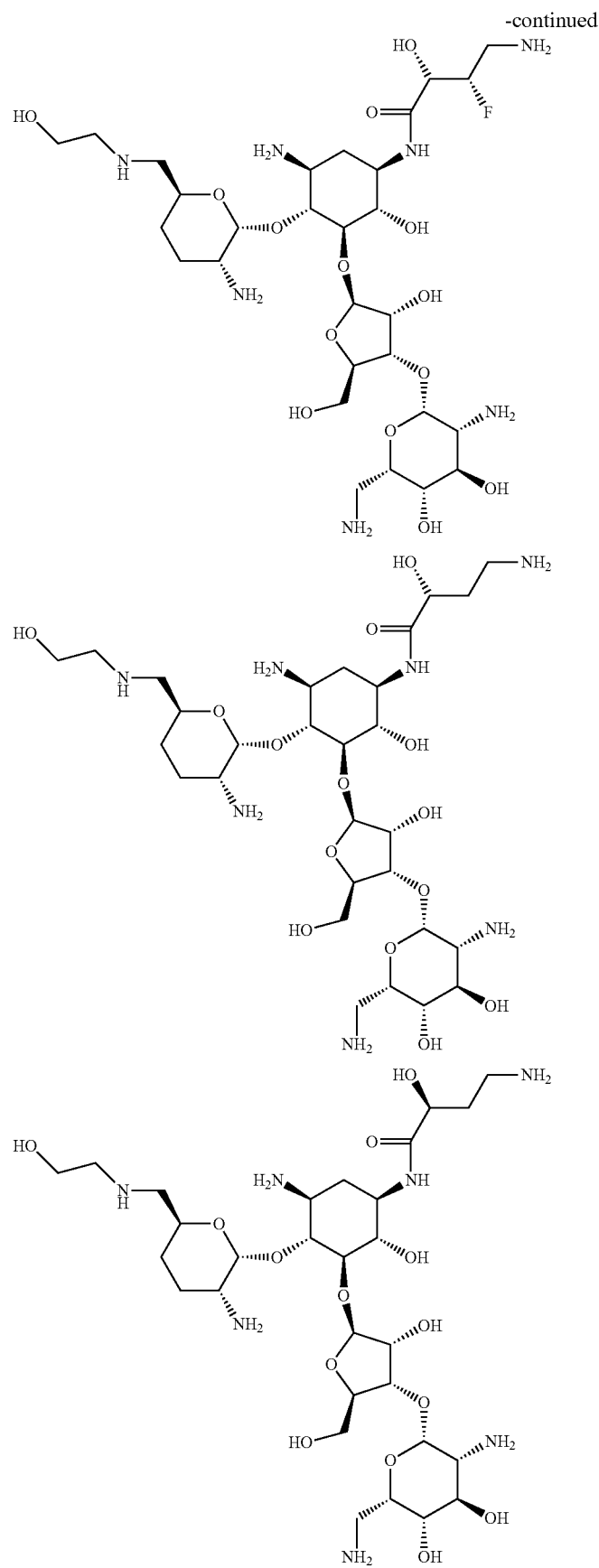

-continued
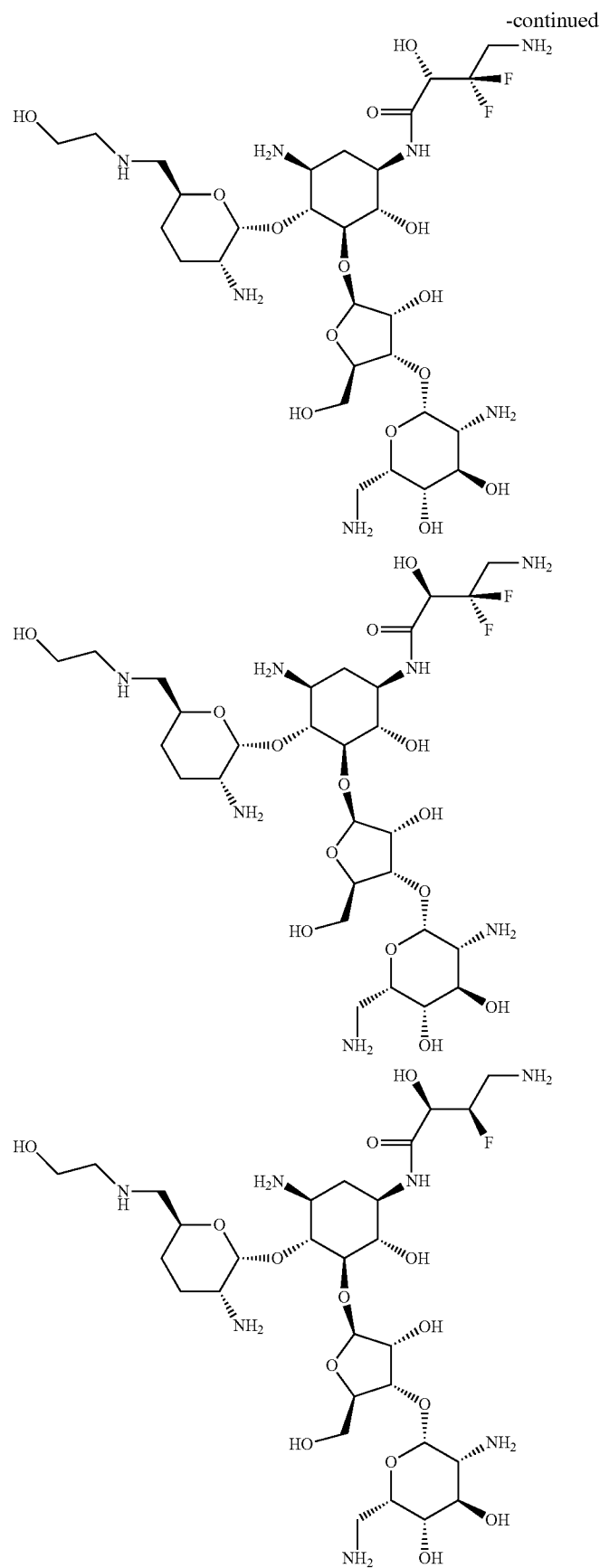

-continued
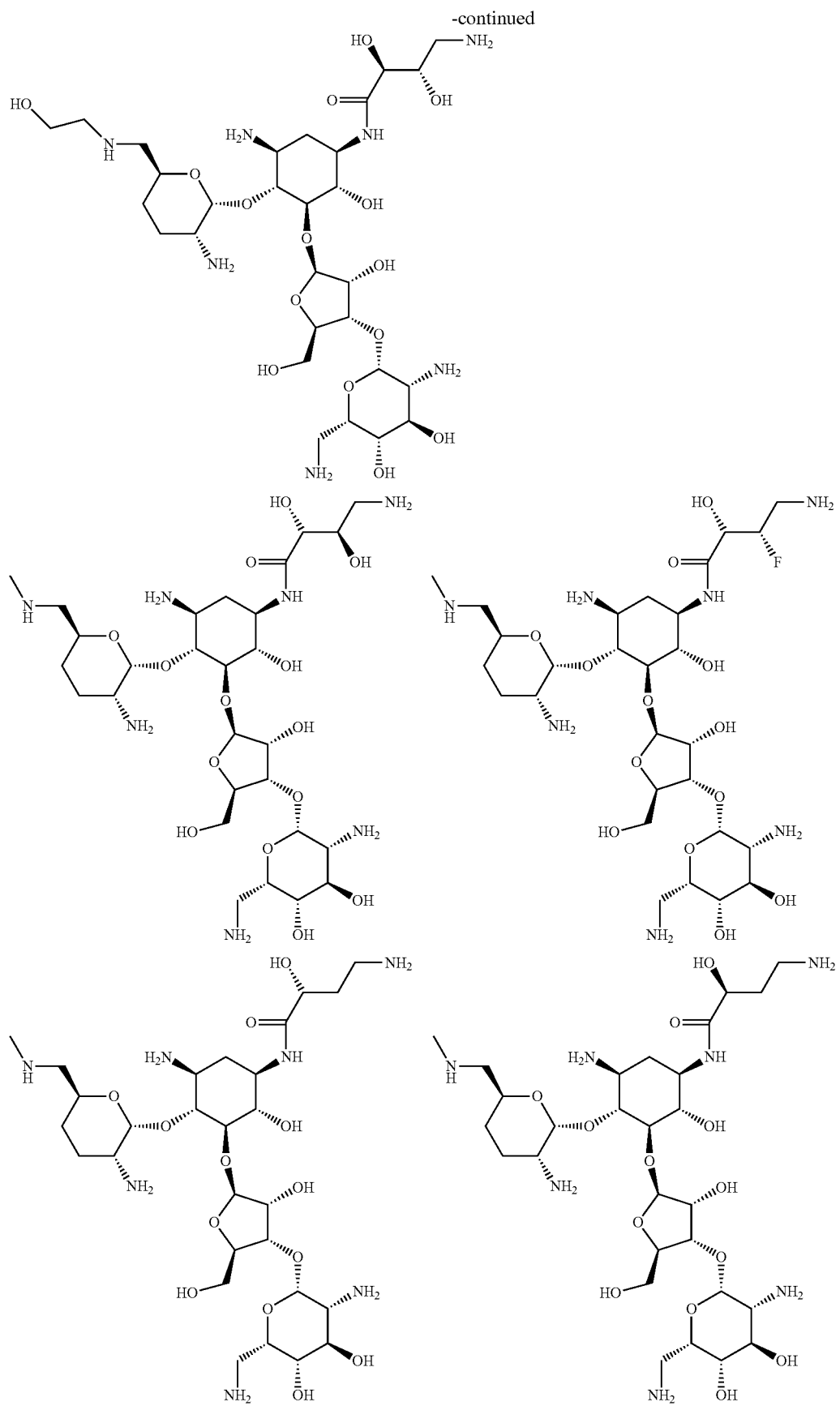

99 100
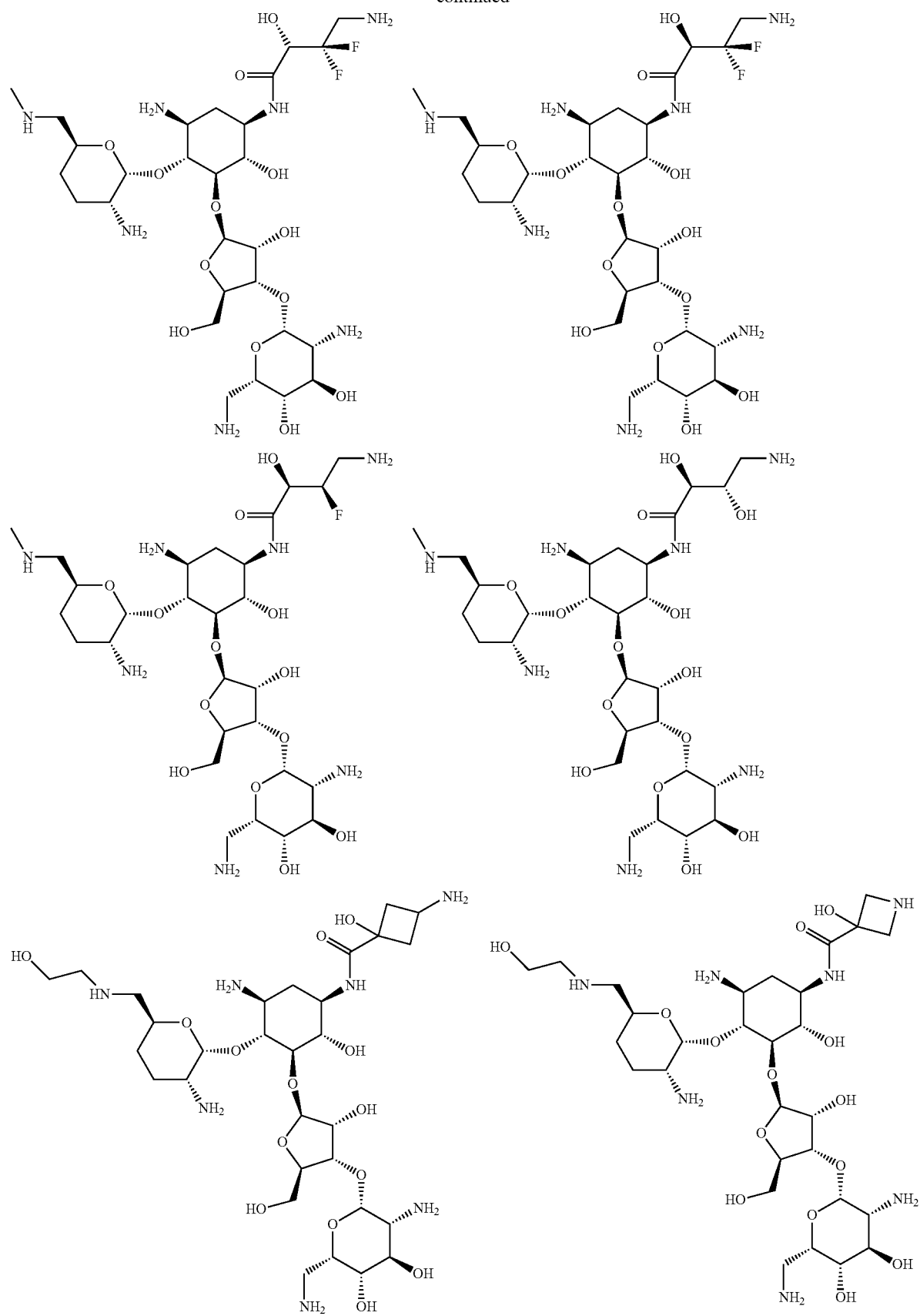
-continued

-continued
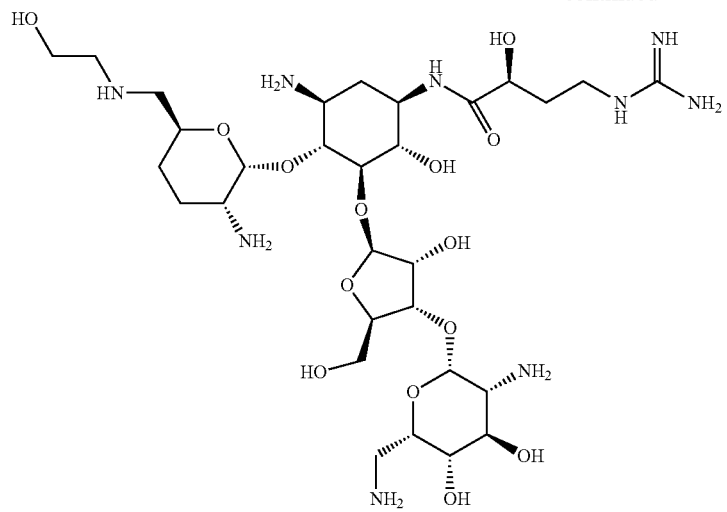
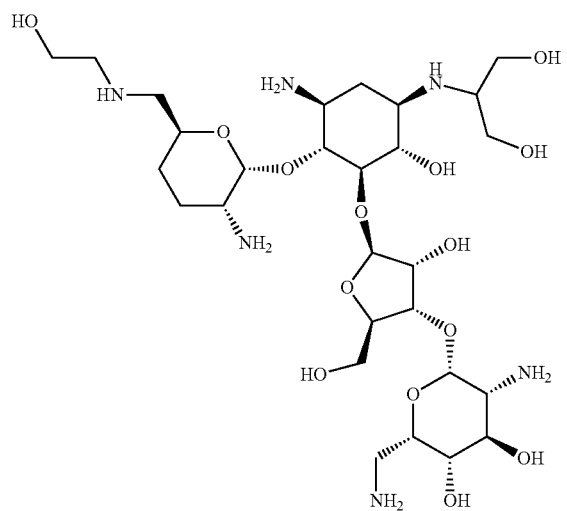
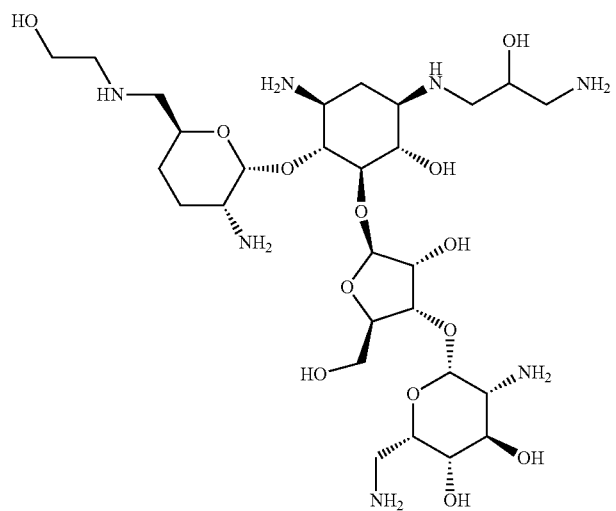

-continued
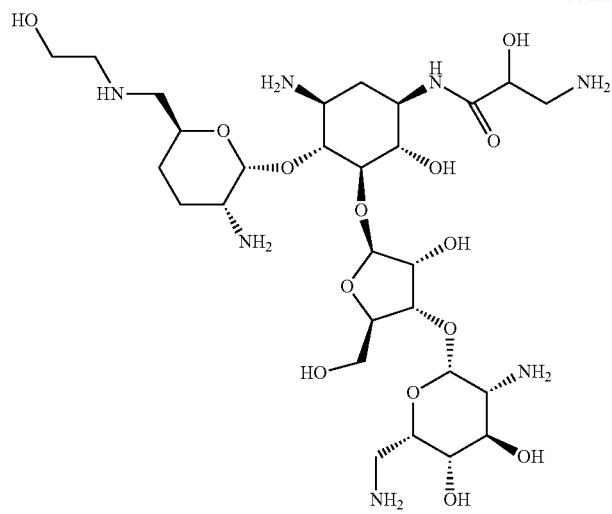
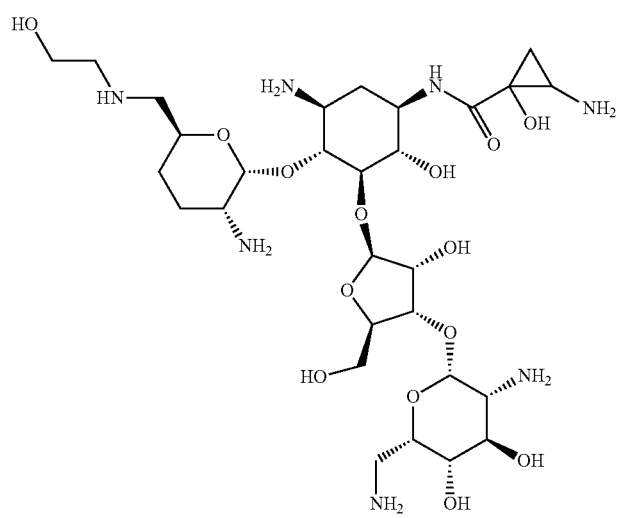
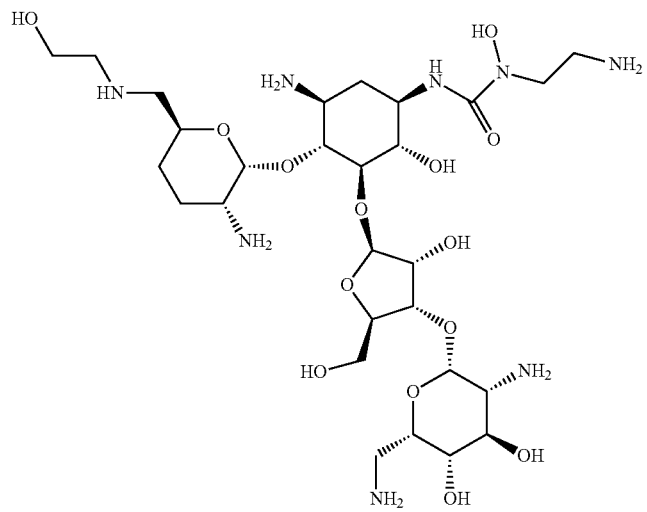

105
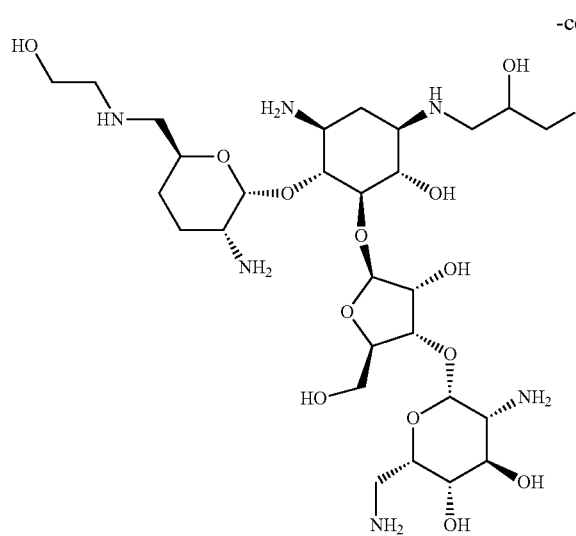
106
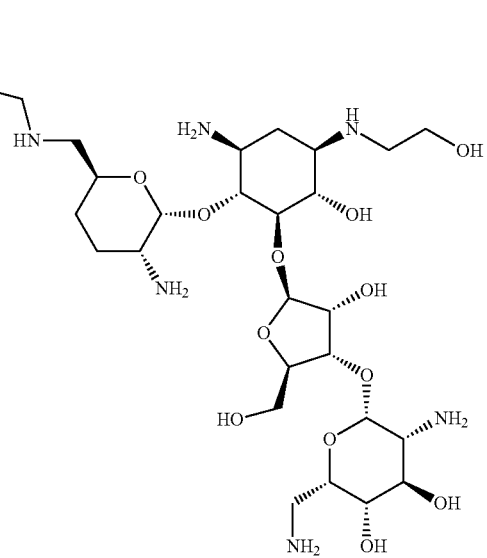
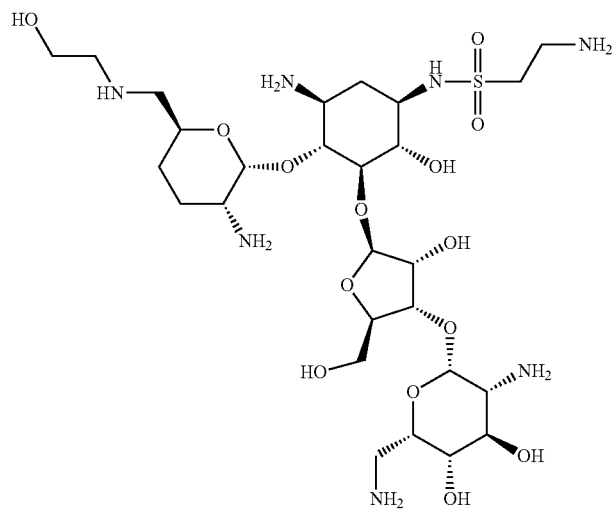
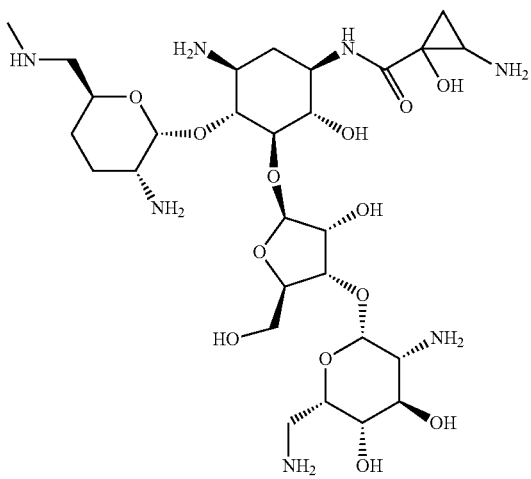
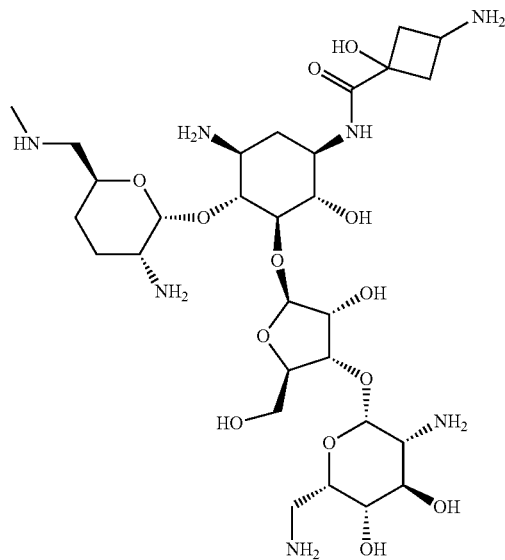
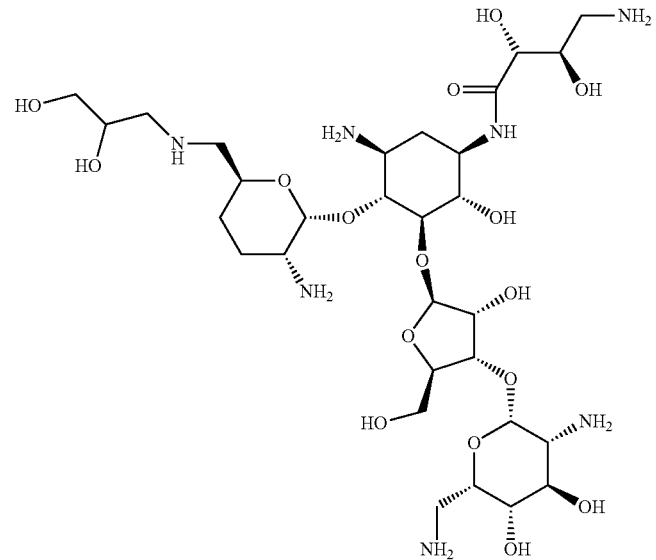

-continued
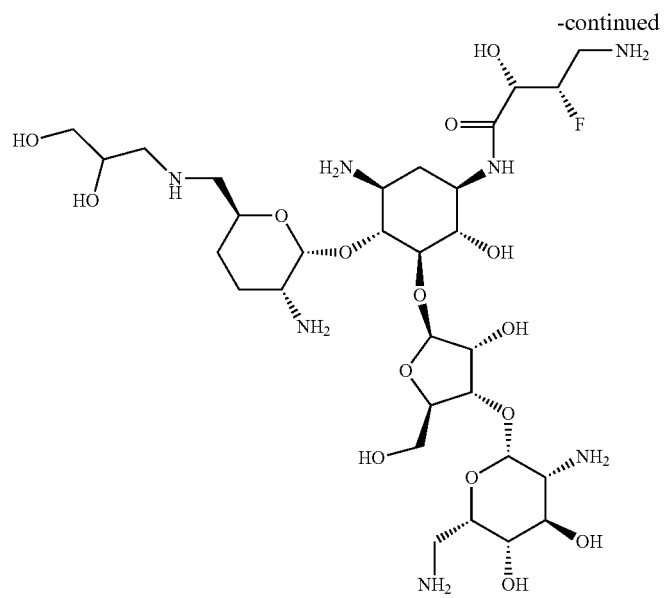
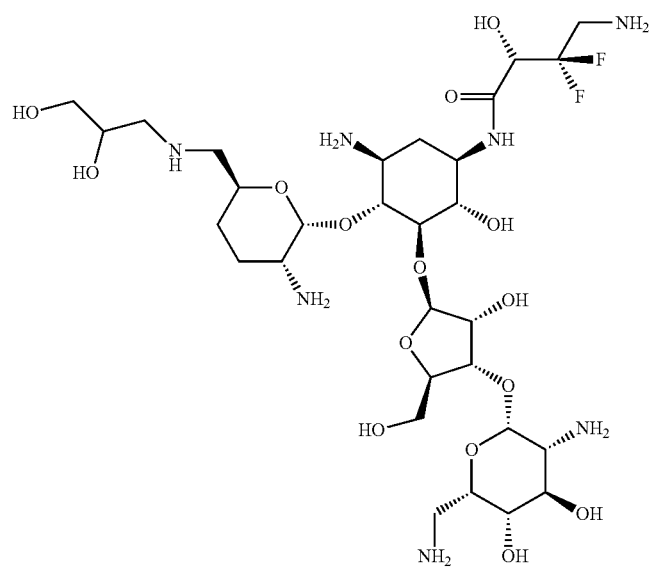
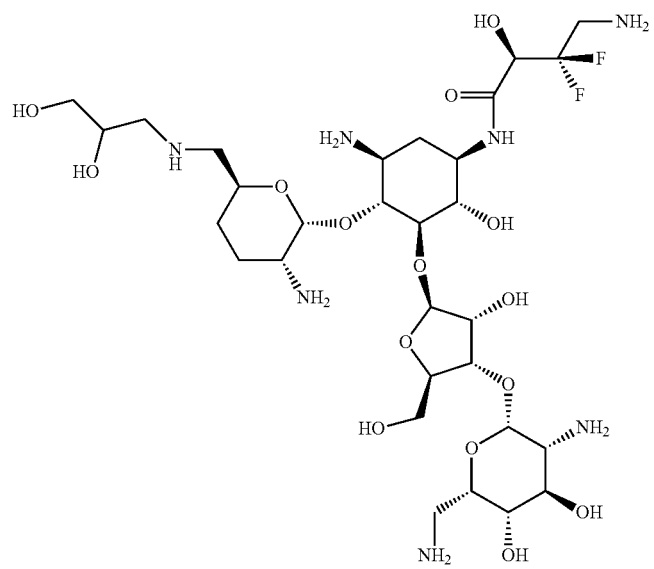

-continued
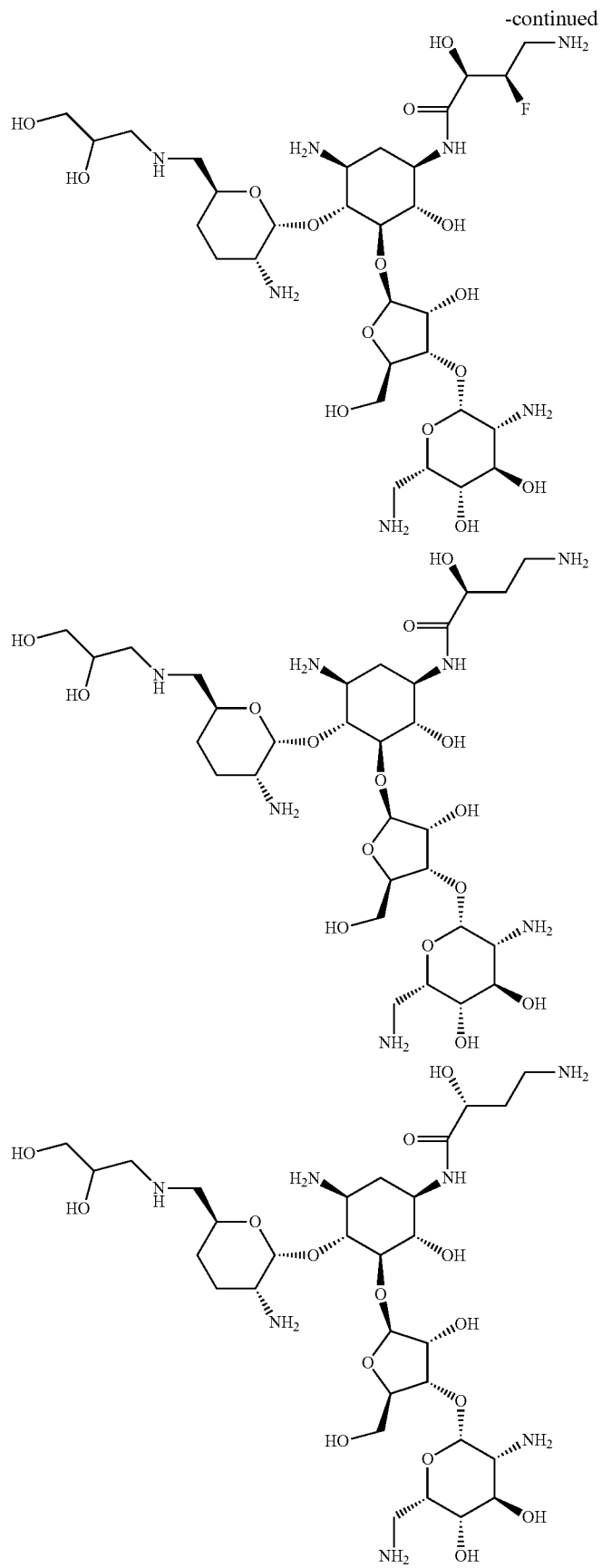

-continued
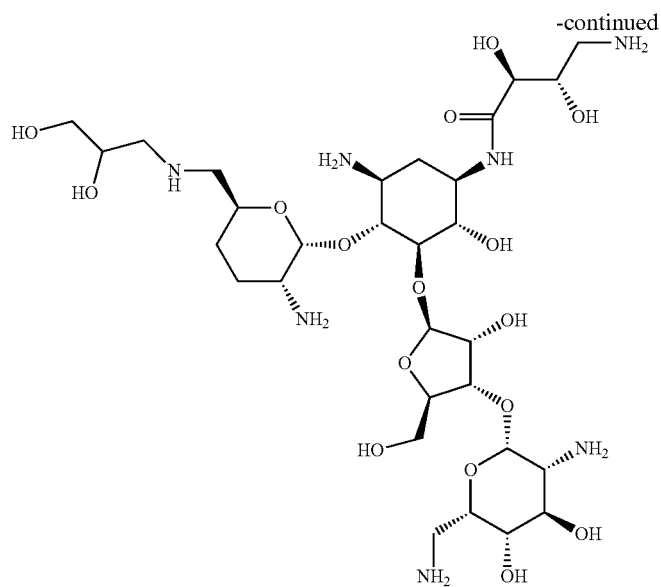
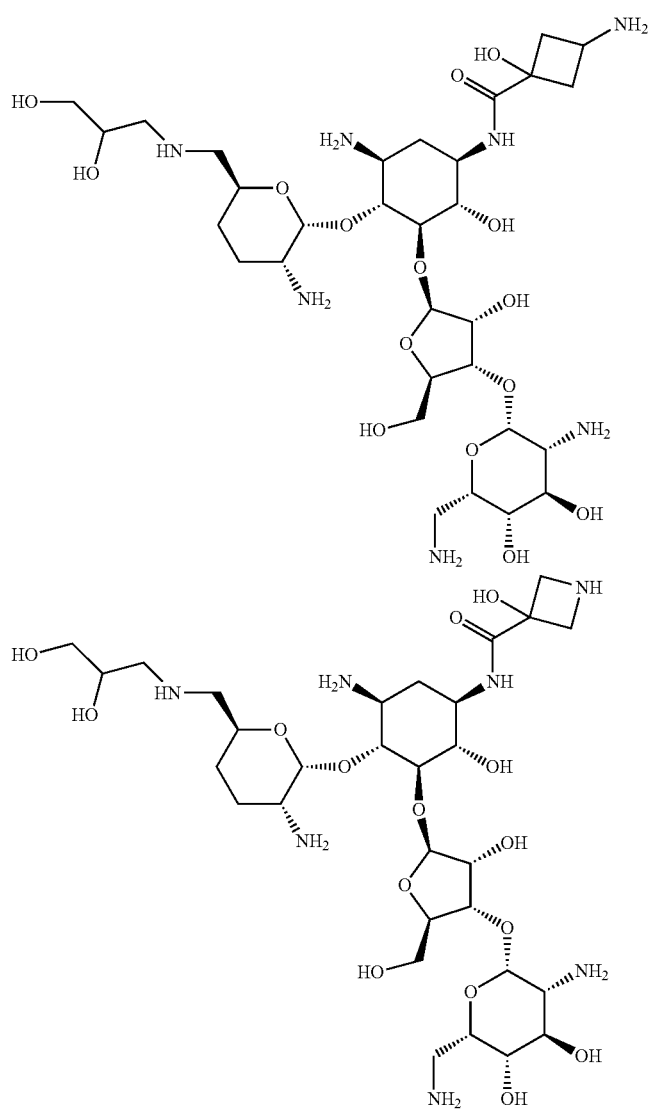

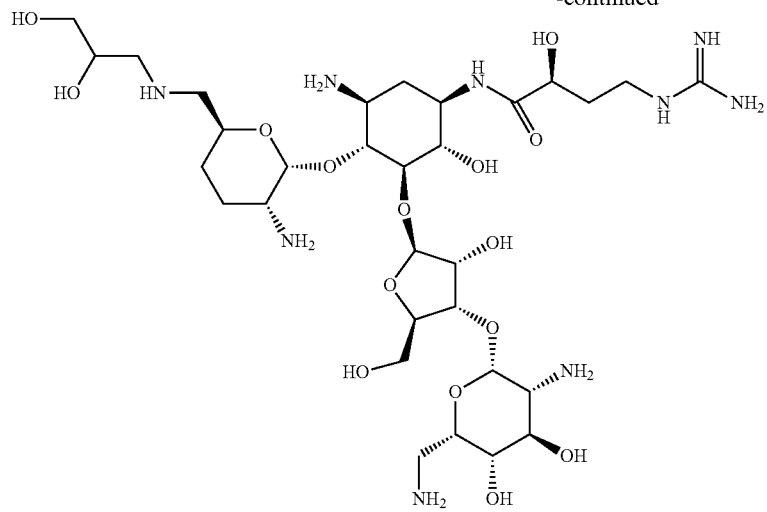
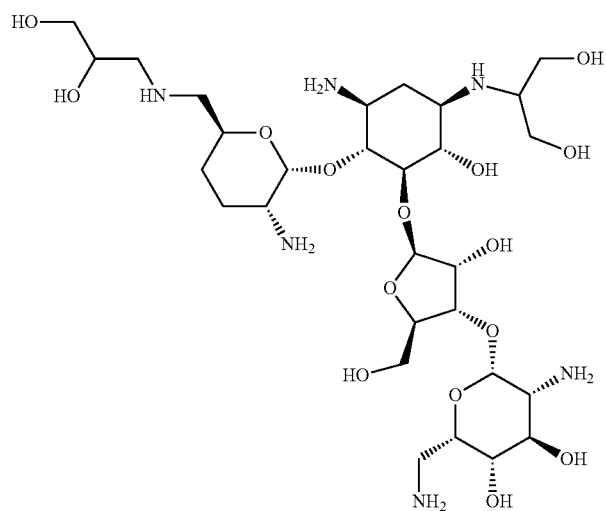
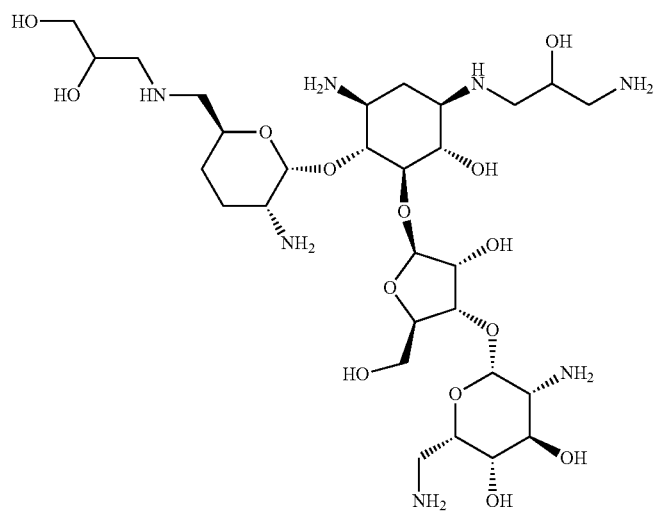

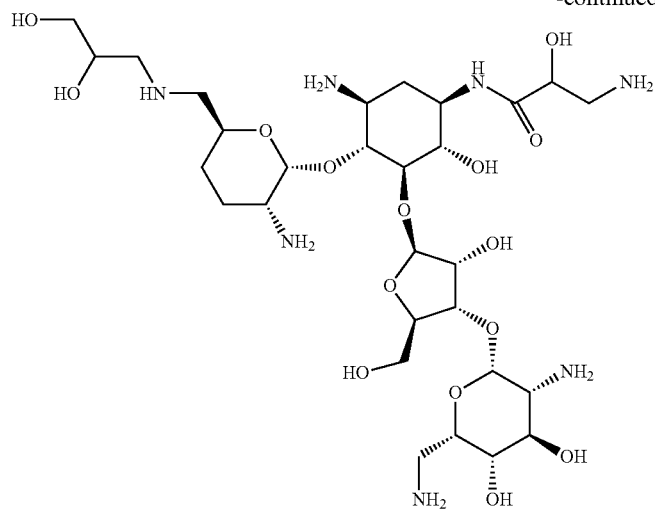
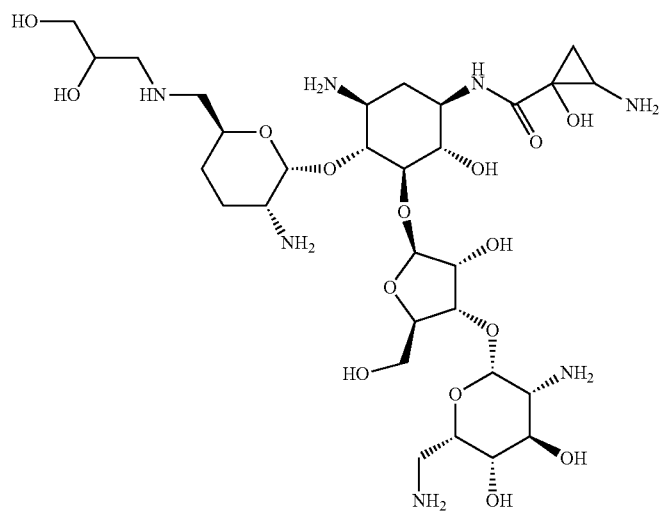
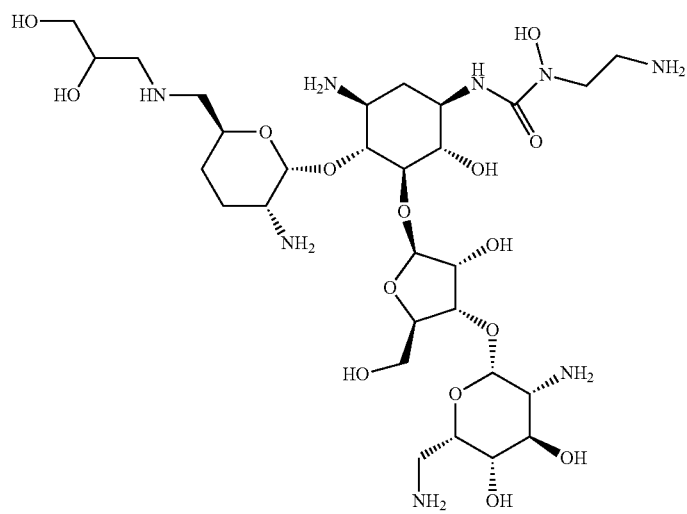

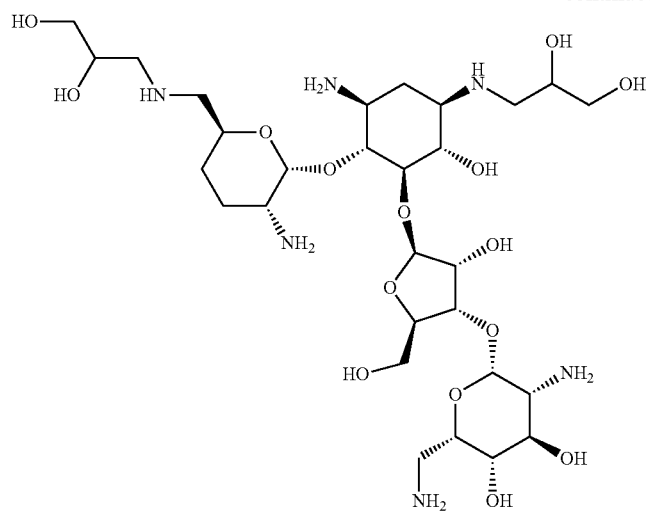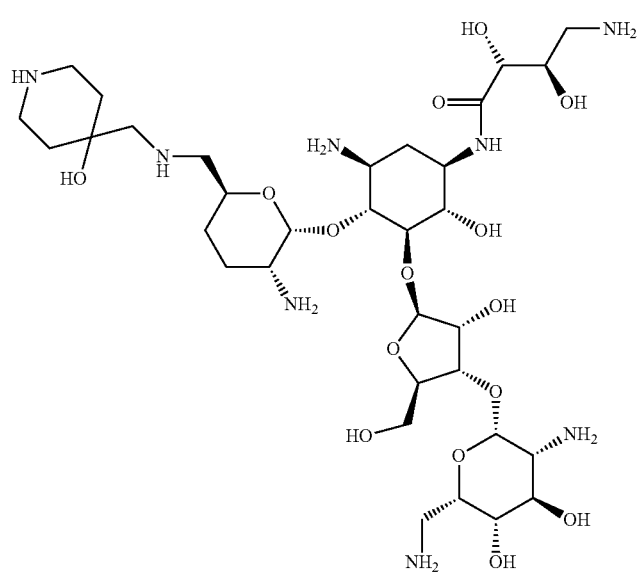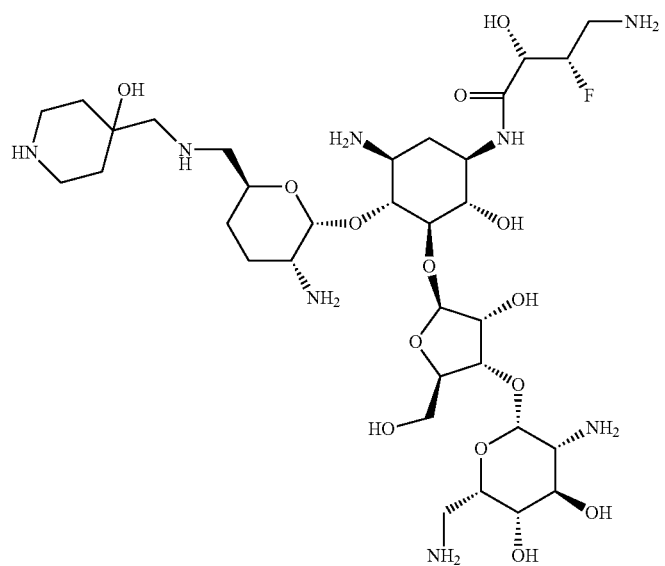

-continued
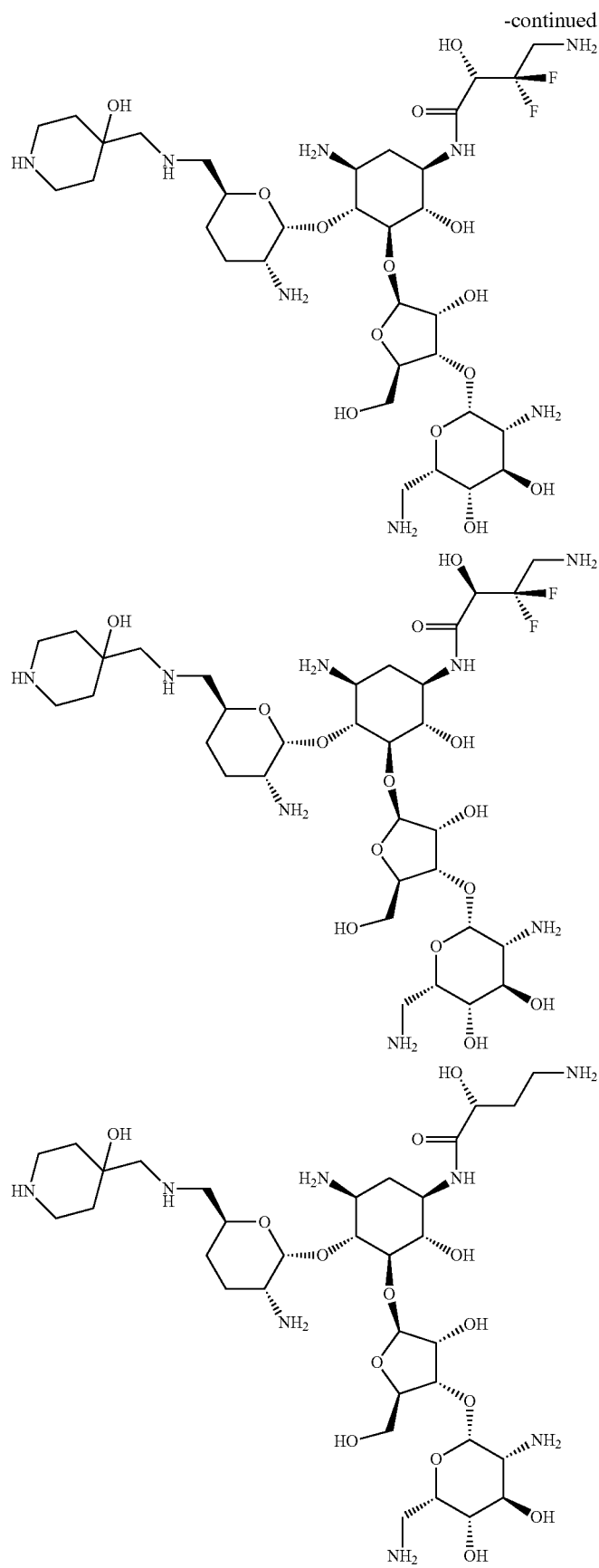

-continued
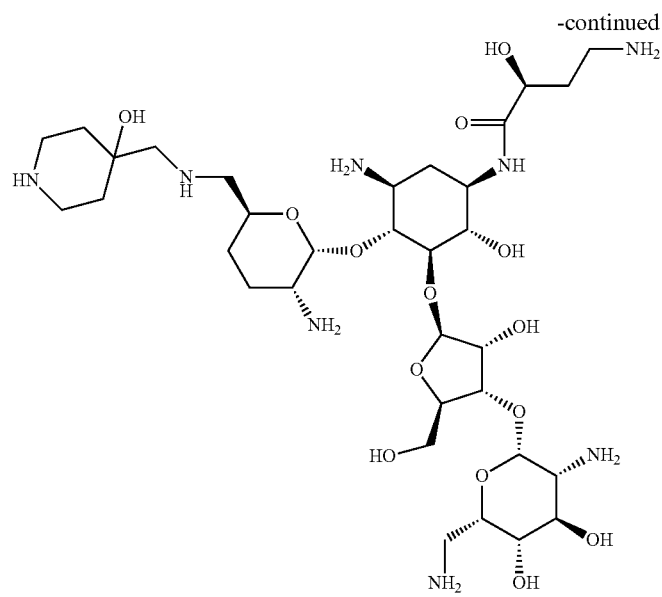
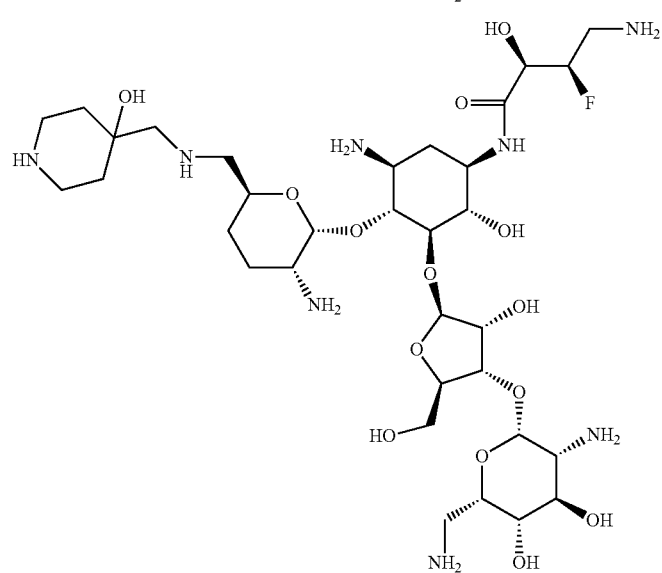
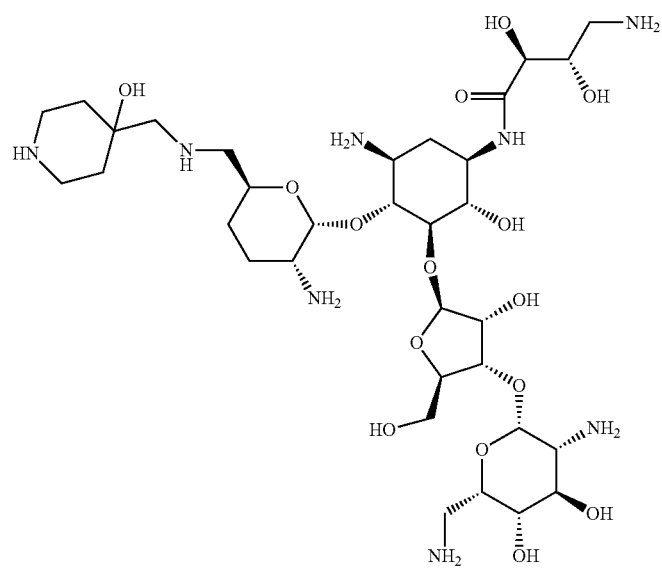

-continued
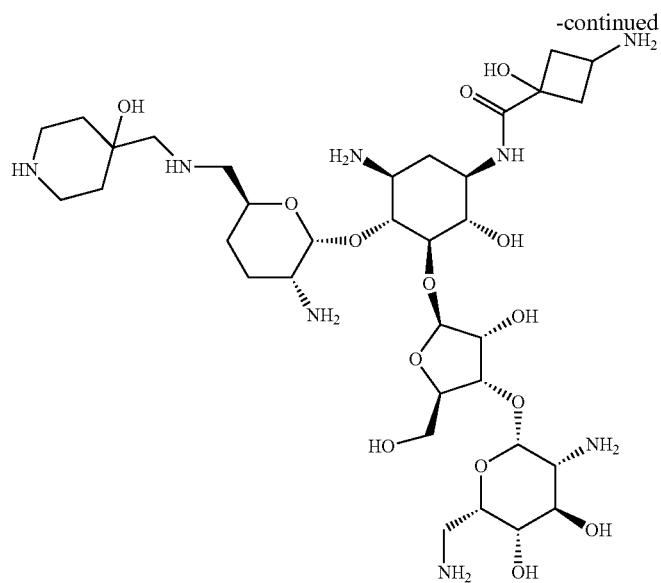
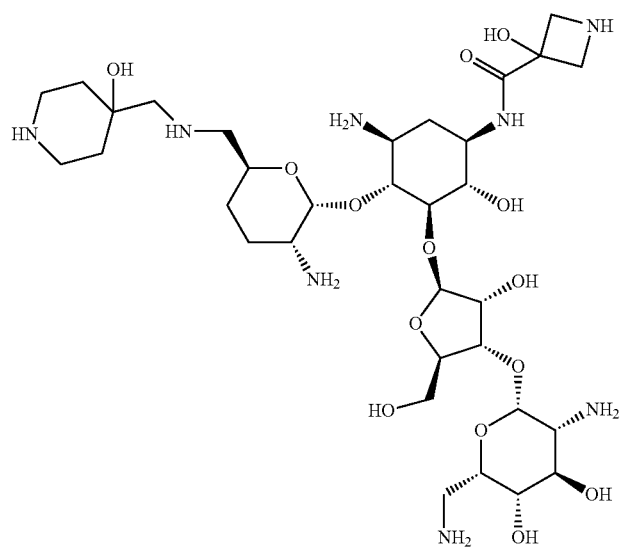
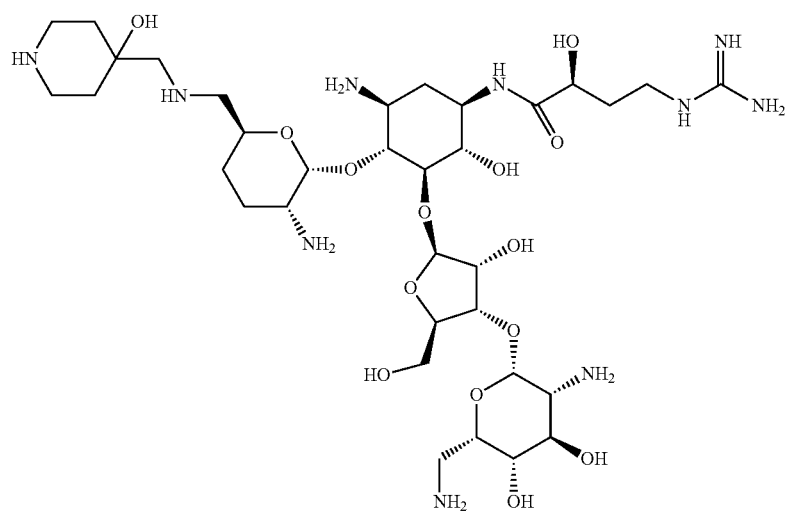

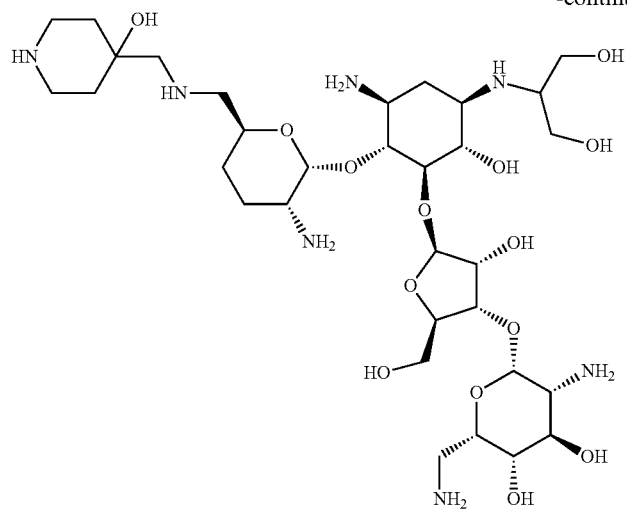
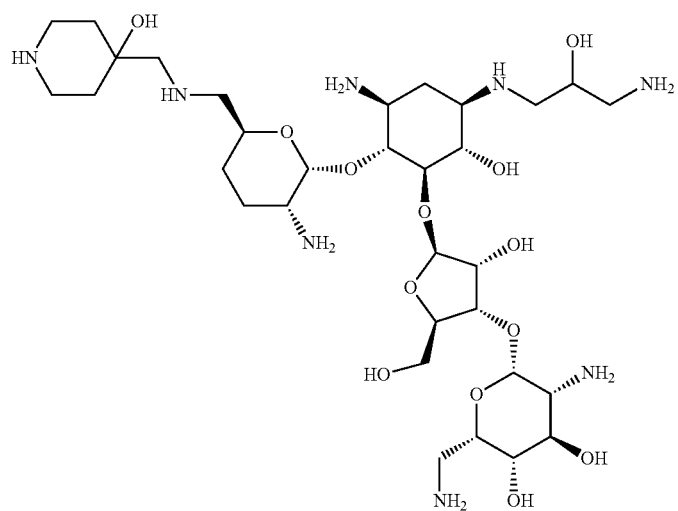
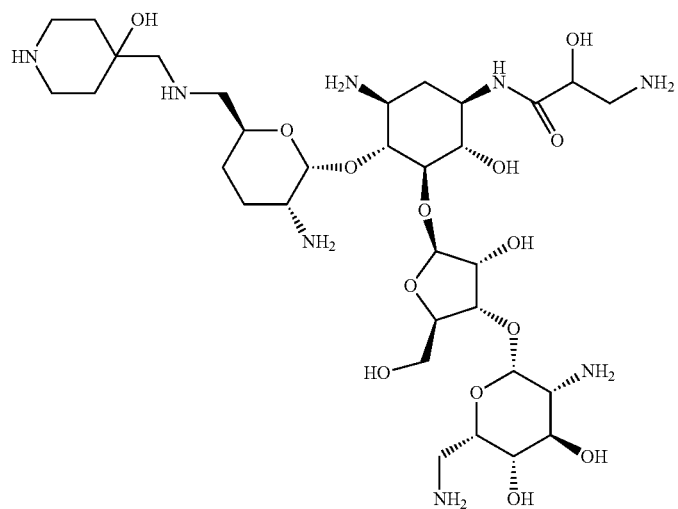

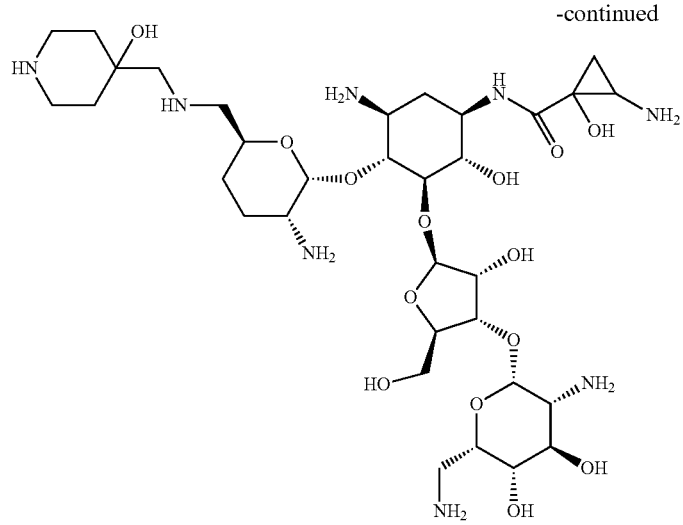
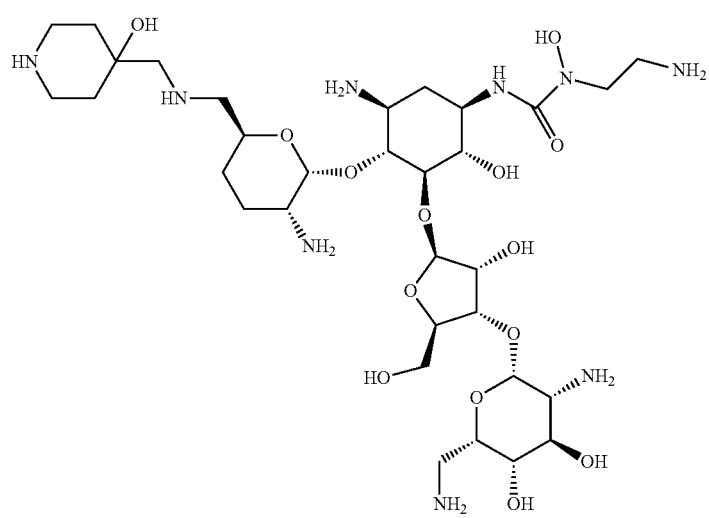
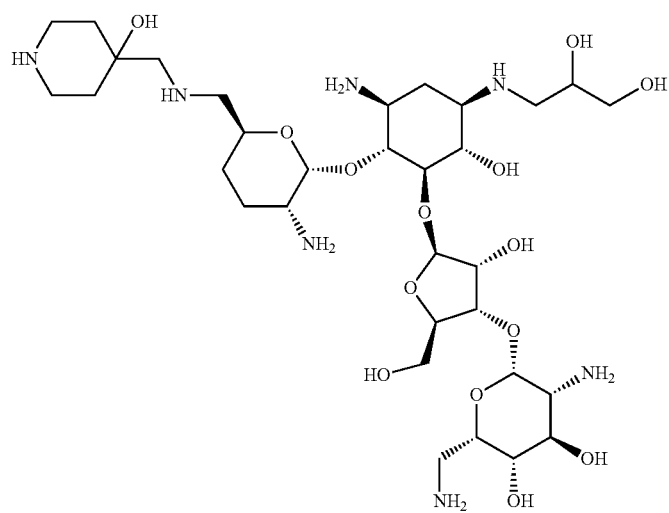

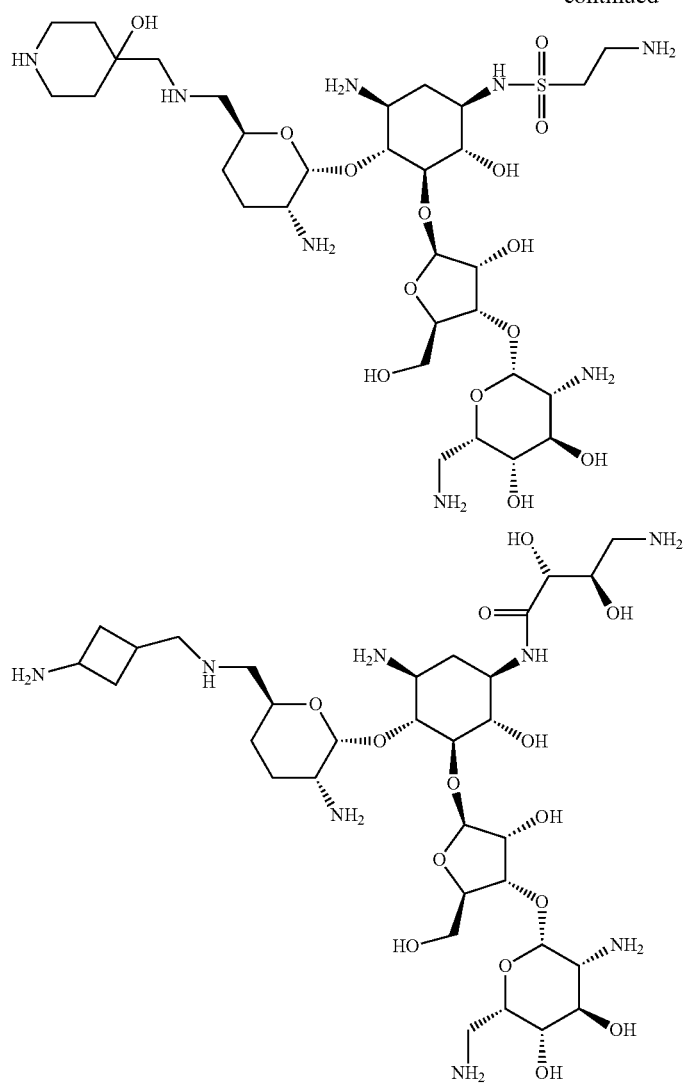
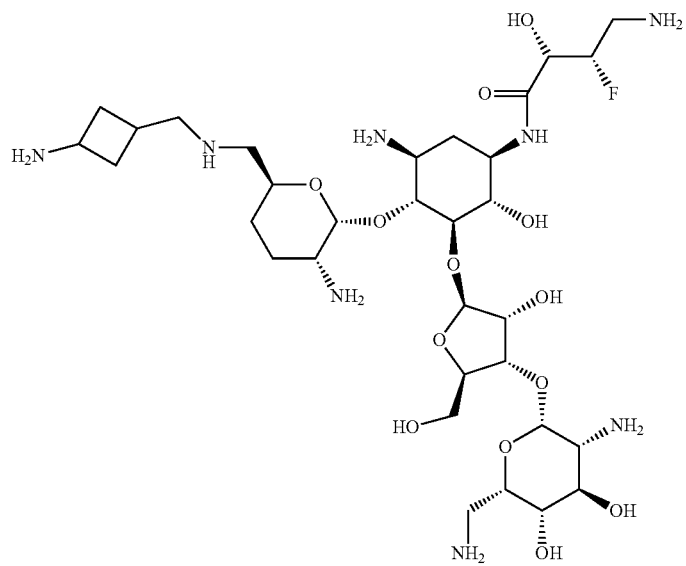

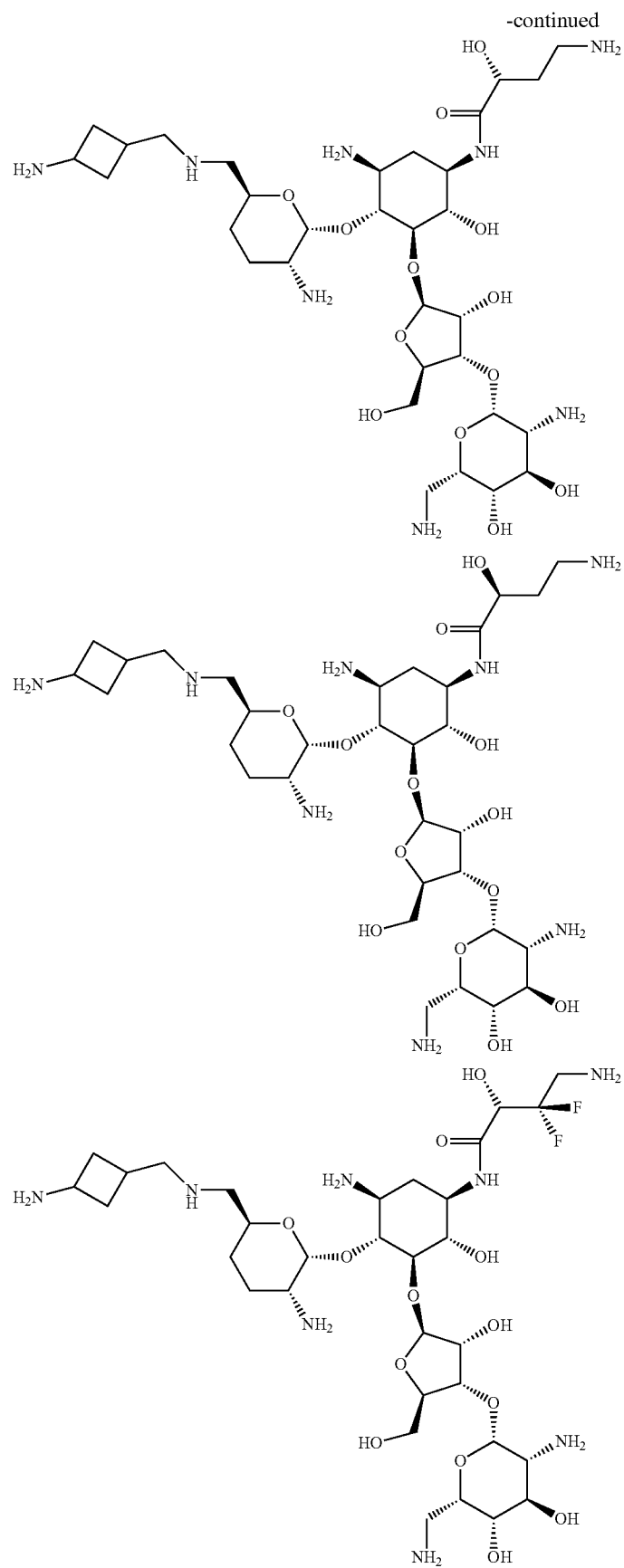

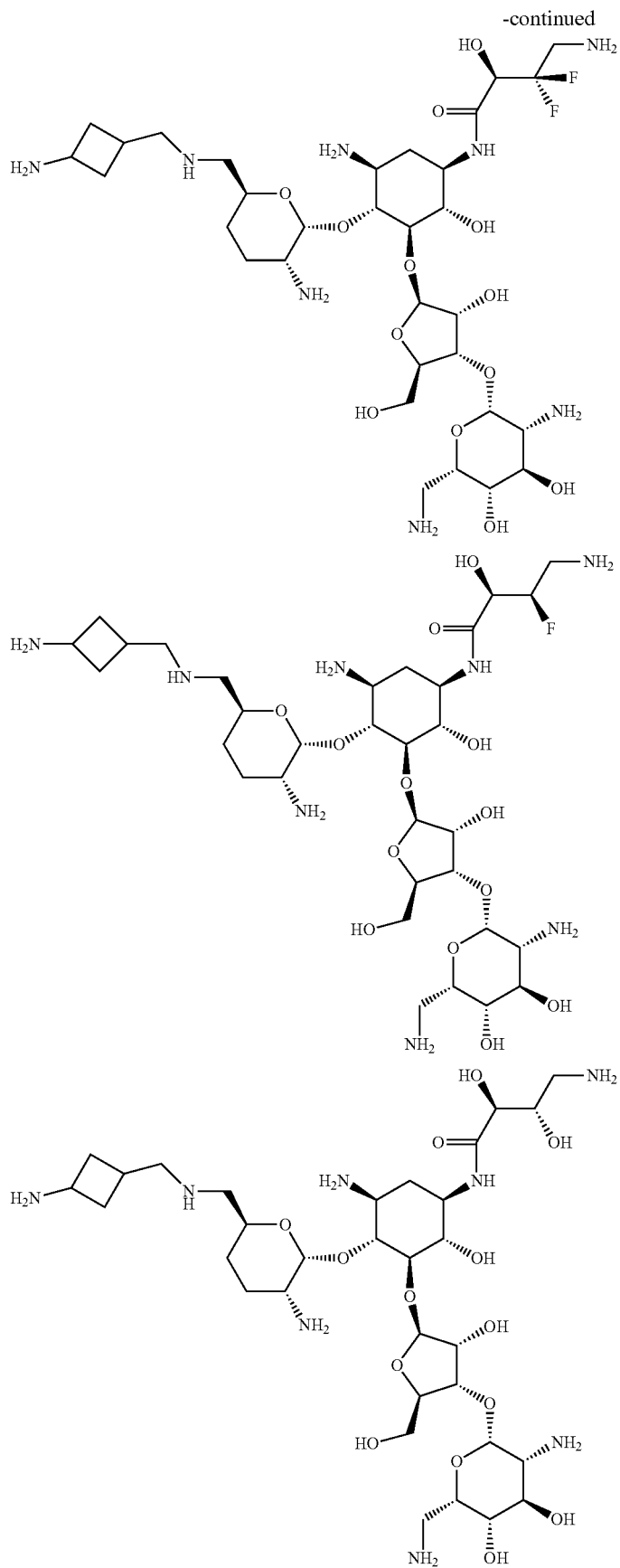

-continued
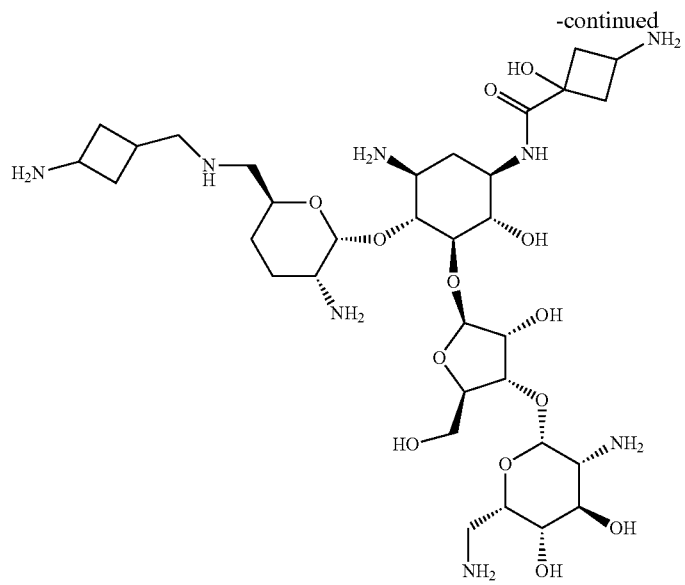
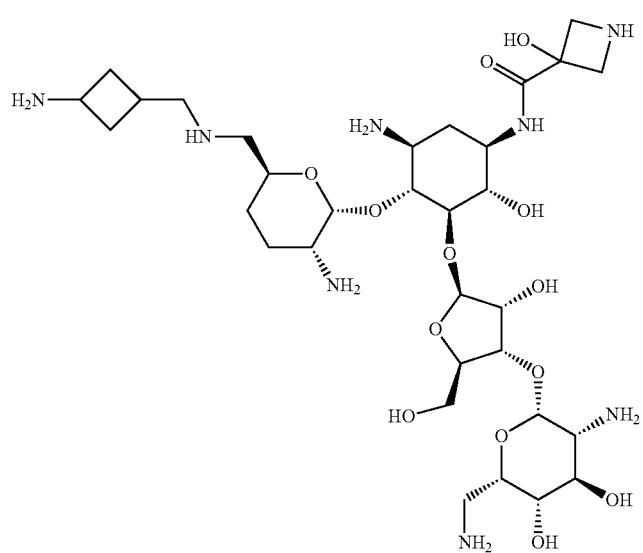
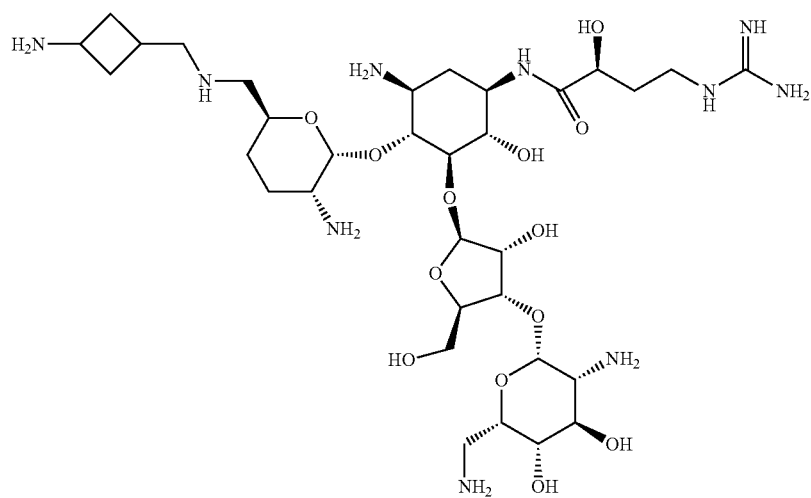

-continued
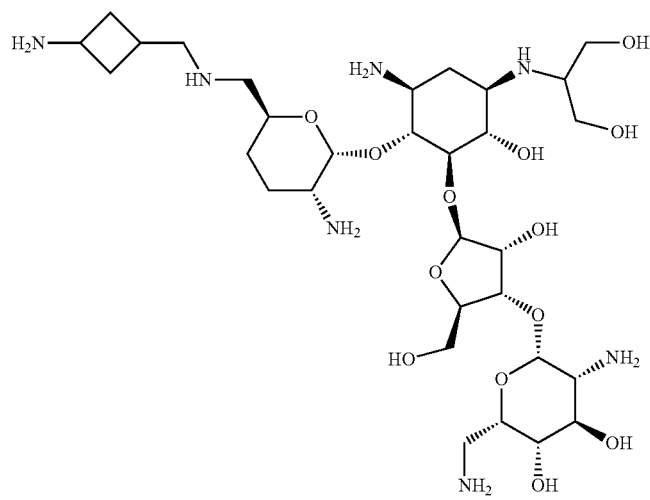
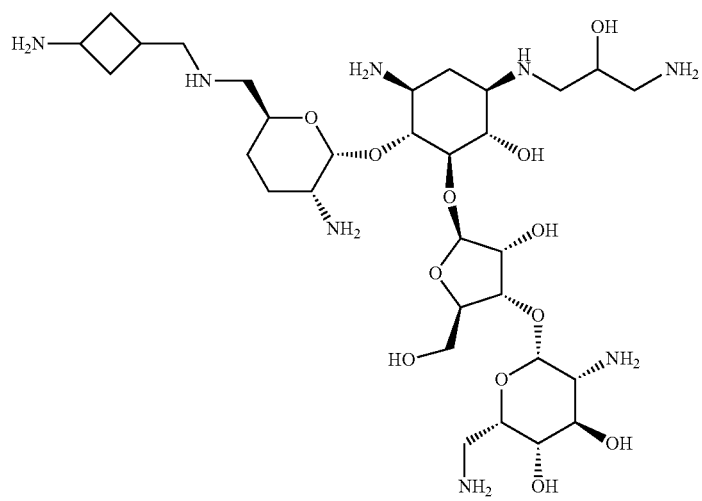
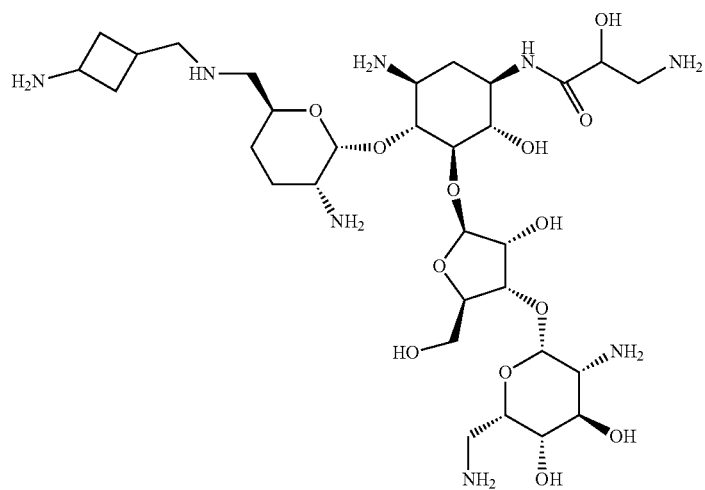

-continued
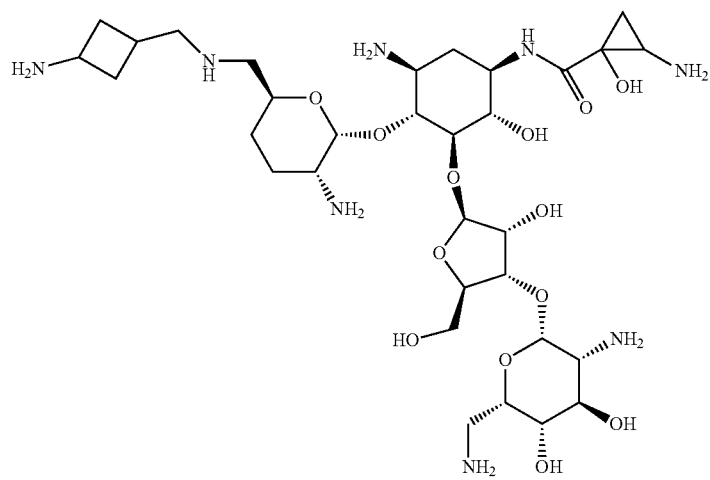
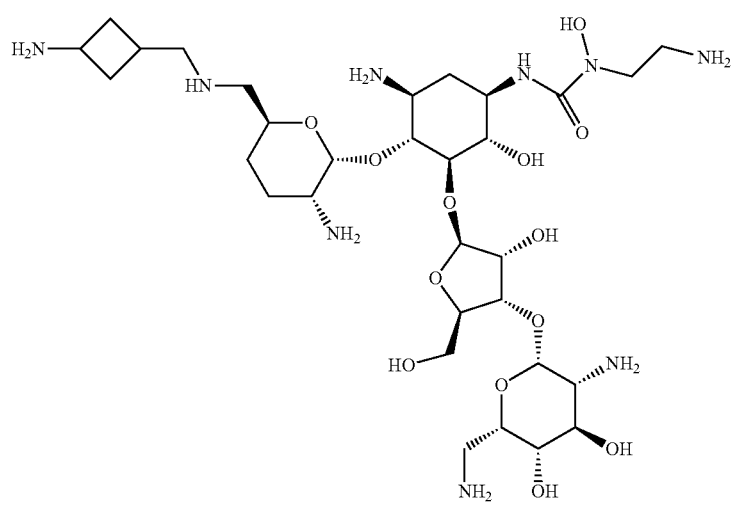
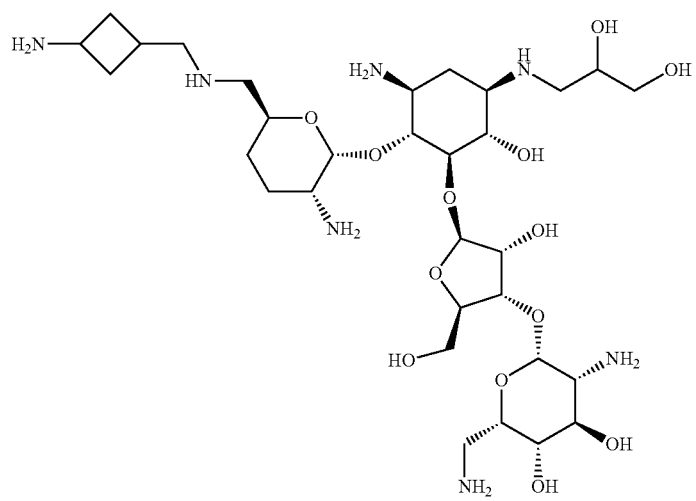

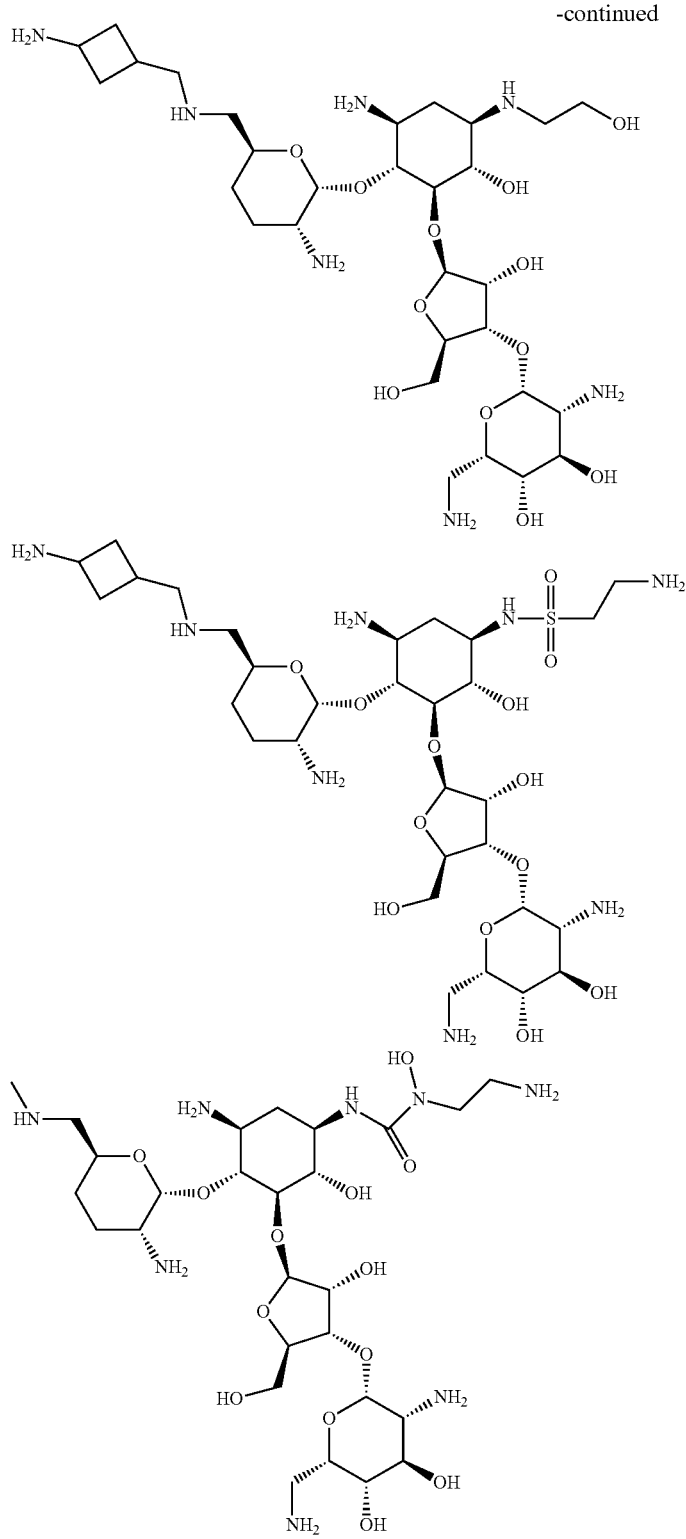

MIC ASSAY PROTOCOL

Minimum inhibitory concentrations (MIC) were determined by reference Clinical and Laboratory Standards Institute (CLSI) broth microdilution methods per M7-A7 [2006]. Quality control ranges utilizing *E. coli* ATCC 25922, *P. aeruginosa* ATCC 27853 and *S. aureus* ATCC 29213, and interpretive criteria for comparator agents were as published in CLSI M100-S17 [2007]. Briefly, serial two-fold dilutions of the test compounds were prepared at 2× concentration in Mueller Hinton Broth. The compound dilutions were mixed in 96-well assay plates in a 1:1 ratio with bacterial inoculum. The inoculum was prepared by suspension of a colony from an agar plate that was prepared the previous day. Bacteria were suspended in sterile saline and added to each assay plate to obtain a final concentration of 5×10⁵ CFU/mL. The plates were incubated at 35C for 20 hours in ambient air. The MIC was determined to be the lowest concentration of the test compound that resulted in no visible bacterial growth as compared to untreated control. Data for certain representative compounds is shown in Table 1 below.

TABLE 1

|  | Representative Compound | |
|---|---|---|
| Example #/Compound # | AEC0001 | APAE001 |
| 1/20 | A | A |

* AEC0001 is ATCC25922 and APAE001 is ATCC27853.
** MIC Key:
  MIC's of 1.0 µg/mL or less=A
  MIC's of greater than 1.0 µg/mL to 16.0 µg/mL=B
  MIC's of greater than 16.0 µg/mL=C All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following structure (I):

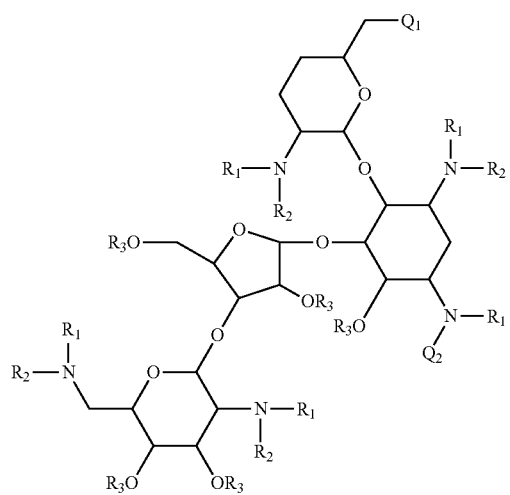

(I)

or a stereoisomer or pharmaceutically acceptable salt thereof, wherein:
$Q_1$ is —$NR_1R_{11}$ or —$NR_{11}R_{12}$;
$Q_2$ is optionally substituted alkyl,

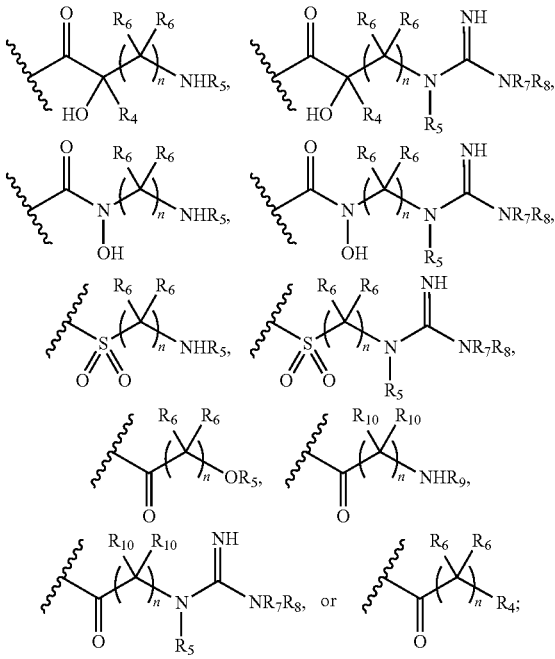

each $R_1$ and $R_2$ is, independently, hydrogen or an amino protecting group;
each $R_3$ is, independently, hydrogen or a hydroxyl protecting group;
each $R_4$, $R_5$, $R_7$ and $R_8$ is, independently, hydrogen or $C_1$-$C_6$ alkyl optionally substituted with one or more halogen, hydroxyl or amino;
each $R_6$ is, independently, hydrogen, halogen, hydroxyl, amino or $C_1$-$C_6$ alkyl;
or $R_4$ and $R_5$ together with the atoms to which they are attached can form a heterocyclic ring having from 4 to 6 ring atoms, or $R_5$ and one $R_6$ together with the atoms to which they are attached can form a heterocyclic ring having from 3 to 6 ring atoms, or $R_4$ and one $R_6$ together with the atoms to which they are attached can form a carbocyclic ring having from 3 to 6 ring atoms, or $R_7$ and $R_8$ together with the atom to which they are attached can form a heterocyclic ring having from 3 to 6 ring atoms;
each $R_9$ is, independently, hydrogen, hydroxyl, amino or $C_1$-$C_6$ alkyl optionally substituted with one or more halogen, hydroxyl or amino;
each $R_{10}$ is, independently, hydrogen, halogen, hydroxyl, amino or $C_1$-$C_6$ alkyl;
or $R_9$ and one $R_{10}$ together with the atoms to which they are attached can form a heterocyclic ring having from 3 to 6 ring atoms;
each $R_{11}$ and $R_{12}$ is, independently, $C_1$-$C_6$ alkyl or substituted $C_1$-$C_6$ alkyl; and
n is an integer from 0 to 4.

2. A compound of claim 1 wherein each $R_1$, $R_2$ and $R_3$ are hydrogen.
3. A compound of claim 1 wherein $Q_1$ is —$NHR_{11}$.
4. A compound of claim 3 wherein $R_{11}$ is substituted $C_1$-$C_6$ alkyl.
5. A compound of claim 4 wherein $R_{11}$ is —$(CH_2)_m OH$, wherein m is an integer from 1 to 6.

6. A compound of claim 5 wherein $R_{11}$ is —(CH$_2$)$_3$OH or —(CH$_2$)$_2$OH.

7. A compound of claim 1 wherein $Q_1$ is —NR$_{11}$R$_{12}$.

8. A compound of claim 1 wherein $Q_2$ is:

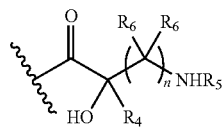

wherein:
$R_4$ is hydrogen;
$R_5$ is hydrogen; and
n is an integer from 1 to 4.

9. A compound of claim 8 wherein each $R_6$ is hydrogen.

10. A compound of claim 9 wherein $Q_2$ is:

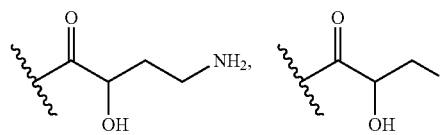 or

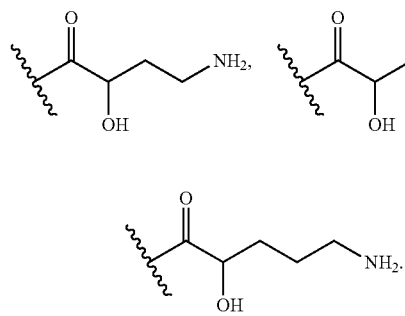

11. A compound of claim 1 wherein Q2 is:

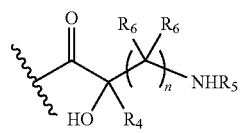

wherein:
$R_4$ is hydrogen;
$R_5$ and one $R_6$ together with the atoms to which they are attached form a heterocyclic ring having from 3 to 6 ring atoms; and
n is an integer from 1 to 4.

12. A compound of claim 1 wherein $Q_2$ is:

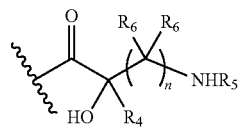

wherein:
$R_4$ and $R_5$ together with the atoms to which they are attached form a heterocyclic ring having from 4 to 6 ring atoms; and
n is an integer from 1 to 4.

13. A compound of claim 1 wherein $Q_2$ is:

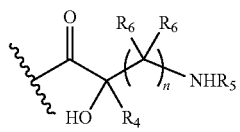

wherein:
$R_5$ is hydrogen;
$R_4$ and one $R_6$ together with the atoms to which they are attached form a carbocyclic ring having from 3 to 6 ring atoms; and
n is an integer from 1 to 4.

14. A compound of claim 1 wherein $Q_2$ is:

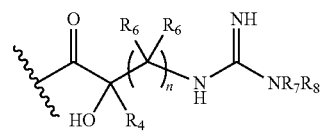

wherein:
$R_4$ is hydrogen;
$R_7$ is hydrogen;
$R_8$ is hydrogen; and
n is an integer from 1 to 4.

15. A compound of claim 1 wherein $Q_2$ is:

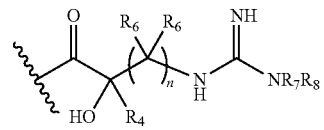

wherein:
$R_4$ and one $R_6$ together with the atoms to which they are attached form a carbocyclic ring having from 3 to 6 ring atoms;
$R_7$ is hydrogen;
$R_8$ is hydrogen; and
n is an integer from 1 to 4.

16. A compound of claim 1 wherein $Q_2$ is:

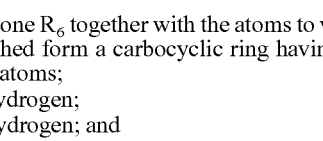

wherein $R_5$ is hydrogen.

17. A compound of claim 1 wherein $Q_2$ is:

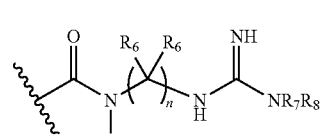

wherein:
$R_7$ is hydrogen; and
$R_8$ is hydrogen.

18. A compound of claim 1 wherein $Q_2$ is:

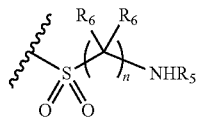

wherein $R_5$ is hydrogen.

19. A compound of claim 1 wherein $Q_2$ is:

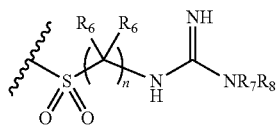

wherein:
   $R_7$ is hydrogen; and
   $R_8$ is hydrogen.

20. A compound of claim 1 wherein $Q_2$ is:

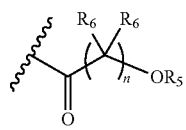

wherein $R_5$ is hydrogen.

21. A compound of claim 1 wherein $Q_2$ is:

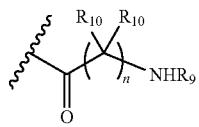

wherein $R_9$ is hydrogen.

22. A compound of claim 1 wherein $Q_2$ is:

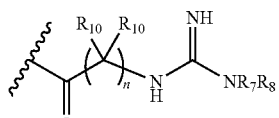

wherein:
   $R_7$ is hydrogen; and
   $R_8$ is hydrogen.

23. A compound of claim 1 wherein $Q_2$ is:

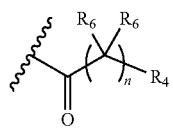

wherein $R_4$ is hydrogen.

24. A compound of claim 1 wherein $Q_2$ is optionally substituted alkyl.

25. A compound of claim 1 having the configuration:

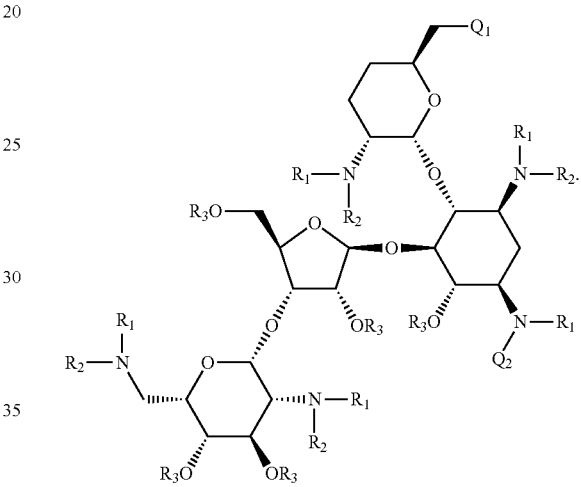

26. A pharmaceutical composition comprising a compound of claim 1, or a stereoisomer or pharmaceutically acceptable salt thereof, and a pharmaceutically acceptable carrier, diluent or excipient.

27. A method of treating a bacterial infection in a mammal comprising administering to the mammal an effective amount of a compound of claim 1 or a pharmaceutical composition of claim 26.

* * * * *